US010077289B2

(12) United States Patent
Pettit et al.

(10) Patent No.: US 10,077,289 B2
(45) Date of Patent: Sep. 18, 2018

(54) CYCLOSPORINS MODIFIED ON THE MEBMT SIDECHAIN BY HETEROCYCLIC RINGS

(71) Applicant: Allergan, Inc., Irvine, CA (US)

(72) Inventors: Simon N. Pettit, Colchester (GB); Andrew D. Jones, Saffron Walden (GB); Catherine Simone V. Frydrych, Sawbridgeworth (GB); Alex J. Thomas, London (GB); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 58 days.

(21) Appl. No.: 15/072,738

(22) Filed: Mar. 17, 2016

(65) Prior Publication Data

US 2016/0289271 A1  Oct. 6, 2016

Related U.S. Application Data

(60) Provisional application No. 62/140,685, filed on Mar. 31, 2015.

(51) Int. Cl.
*A61K 38/12* (2006.01)
*C07K 7/64* (2006.01)
*A61K 38/00* (2006.01)

(52) U.S. Cl.
CPC .............. *C07K 7/645* (2013.01); *A61K 38/00* (2013.01)

(58) Field of Classification Search
None
See application file for complete search history.

(56) References Cited

U.S. PATENT DOCUMENTS

| 4,826,833 | A | 5/1989 | Chen |
| 5,214,130 | A | 5/1993 | Patchett et al. |
| 5,474,979 | A | 12/1995 | Ding et al. |
| 7,538,084 | B2 * | 5/2009 | Molino ................ C07K 7/645 514/1.1 |
| 9,266,927 | B2 | 2/2016 | Pettit et al. |
| 2006/0069015 | A1 | 3/2006 | Molino et al. |
| 2010/0167996 | A1 | 7/2010 | Fliri et al. |
| 2016/0039880 | A1 | 2/2016 | Pettit et al. |

FOREIGN PATENT DOCUMENTS

| EP | 103264 | A2 | 3/1984 |
| EP | 1602645 | A1 | 12/2005 |
| WO | 2003-033010 | A1 | 4/2003 |
| WO | WO 2004/072108 | * | 8/2004 |
| WO | WO2004072108 | A1 | 8/2004 |
| WO | 2004-082629 | A2 | 9/2004 |
| WO | 2011-150156 | A3 | 12/2011 |
| WO | 2012-051194 | A1 | 4/2012 |
| WO | 2013-181339 | A2 | 12/2013 |
| WO | 2014-049540 | A2 | 4/2014 |
| WO | WO2016112321 | A1 | 7/2016 |

OTHER PUBLICATIONS

Lu, Bioconjugate Chem. 2001, 12, 129-133.*
Anderson et al, The Practice of Medicinal Chemistry, 1996, 32 Pages, 3rd Edition.
Berge, Stephen M., Pharmaceutical Salts, Journal of Pharmaceutical Sciences, Jan. 1977, 1-19, 66 (1), US.
Bingham, Ann et al, Over One Hundred Solvates of Sulfathiazole, Chem. Commun., 2001, 603-604.
Bron, Anthony et al, Methodologies to Diagnose and Monitor Dry Eye Disease:Report of the Diagnostic Methodology Subcommittee of the International Dry Eye WorkShop, Ocul. Surf., 2007, 108-152, 5(2).
Caira, Mino et al, Preparation and Crystal Characterization of a Polymorph, a Monohydrate, and an Ethyl Acetate Solvate of the Antifungal Fluconazole, Journal of Pharmaceutical Sciences, Mar. 2004, 601-611, 93(3).
Cresp, Terry M. et al., Synthesis of Piloquinone, a Phenanthrene-9, 10-quinone from Streptromyces pilosus, Dept. of Organic Chemistry, Univ of Western Australia, Nedlands, Western Australia 2009, Australia, 1974, pp. 11-12.
Cross, LC, Rules for the Nomenclature of Organic Chemistry Section E: Sterochemistry, Pure & Appl. Chem., 1976, 11-30, 45.
Eberle, M.K. et al, Modifications of the MeBmt Side Chain of Cyclosporin A, Bioorganic & Medicinal Chemistry Letters, Aug. 1995, 1725-1728, 5(15).
Elrod, John et al, Physiologic Functions of Cyclophilin D and the Mitochondrial Permeability Transition Pore, Circulation Journal, 2013, 12 Pages.
Fu, Jiping et al, Potent Nonimmunosuppressive Cyclophilin Inhibitors With Improved Pharmaceutical Properties and Decreased Transporter Inhibition, J Med Chem, 2014, 8503-8516, 57.
Gould, Philip, Salt Selection for Basic Drugs, International Journal of Pharmaceutics, 1986, 201-217, 33.
Greene, Theodora, Protective Groups in Organic Synthesis, 1991, 52 Pages, 3rd Edition.
Heinrich Stahl, Pharmaceutical Salts, Handbook of Pharmaceutical Salts, 2002, 329-345, International Union of Pure and Applied Chemistry, Verlag Helvetica Chemica Acta-Zürich.
Hubler, Francis et al, Synthetic routes to NetXaa4-cyclosporin A derivatives as potential anti-HIV 2 drugs, Tet. Lett., 2000, 7193-7196, 41.
Lee, Jinhwa et al, Current Implications of Cyclophilins in Human Cancers, Journal of Experimental & Clinical Cancer Research, 2010, 6 Pages, 29(97).
Lemp, Michael et al, The Definition and Classification of Dry Eye Disease: Report of the Definition and Classification Subcommittee of the International Dry Eye Workshop, Ocular Surface, Apr. 2007, 75-92, 5(2).

(Continued)

*Primary Examiner* — Satyanarayana R Gudibande
(74) *Attorney, Agent, or Firm* — Laura L. Wine

(57) ABSTRACT

The present invention relates to novel cyclosporin analogs, processes for preparing them, pharmaceutical compositions containing them, and methods for using these analogs and the compositions containing them for the treatment of medical conditions, including but not limited to ocular conditions such as dry eye.

7 Claims, No Drawings

(56) References Cited

OTHER PUBLICATIONS

Papagni, Antonio et al., Novel fluorinated amino-stilbenes and their solid-state photodimerization, New Journal of Chemistry, 2010, pp. 2612-2621, vol. 34.

Patent Cooperation Treaty, Notification of Transmittal of the International Search Report & the Written Opinion of the International Searching Authority, or the Declaration, PCT/US2016/022920, dated Aug. 12, 2016, pp. 17.

Perevalov, V.P. et al., Sytheses from 1,3- and 1,5-Dimethylpyrazoles, Journal of General Chemisry of the USSR, 1982, pp. 2297-2303, Plenum Publishing Corp.

Pflegfelder, Stephen C., Antiinflammatory Therapy for Dry Eye, American Journal of Ophthalmology, Feb. 2004, 337-342, 137 (2), US.

Piot, Christophe et al, Effect of Cyclosporine on Reperfusion Injury in Acute Myocardial Infarction, New England Journal of Medicine, Jul. 2008, 473-481, 359.

Rao, G. Venkateswara et al, Synthesis of 2-(N-disubstituted amino)ethyltriphenylphosphonium bromides, Tetrahedron Letters, 2008, 824-826, 49.

Riss, Bernard et al, Development of a Practical Process for the Opening of Macrocyclic Cyclosporin A and Amino Acid Deletion, Org Process Dev, 2014, 1763-1770, 18.

Seebach, Dieter, Modification of Cyclosporin A (CS): Generation of an Enolate at Thesarcosine Residue and Reactions with Electrophiles, Helvetica Chimica, 1993, 1564-1590, 76 (4).

Sweeney, Zachary et al, From Chemical Tools to Clinical Medicines: Nonimmunosuppressive Cyclophilin Inhibitors Derived from the Cyclosporin and Sanglifehrin Scaffolds, J Med Chem, 2014, 7145-7159, 57(17).

Traber, Rene et al, Cyclosporins—New Analogues by Precursor Directed Biosynthesis, The Journal of Antibiotics, Apr. 1989, 591-597.

Van Tonder, Elsa et al, Preparation and Physicochemical Characterization of 5 Niclosamide Solvates and 1 Hemisolvate, AAPS PharmSciTech, 2004, 1-10, 5(1).

Zhang, Jian-Xin et al., An Improved Preparation Method of Benzyl and Thenyl Triphenylphosphonium Salts, Synthetic Communications, 1996, pp. 3091-3095, vol. 26, No. 16.

* cited by examiner

CYCLOSPORINS MODIFIED ON THE MEBMT SIDECHAIN BY HETEROCYCLIC RINGS

CROSS-REFERENCE TO RELATED APPLICATIONS

This application claims the benefit of U.S. Provisional Patent Application No. 62/140,685, filed on Mar. 31, 2015, the entire contents of which is incorporated herein by reference in its entirety.

FIELD OF THE INVENTION

The present invention relates to novel cyclosporin analogs, processes for preparing them, pharmaceutical compositions containing them, and methods for using these analogs and compositions containing them for the treatment of medical conditions, including but not limited to ocular conditions such as dry eye.

BACKGROUND OF THE INVENTION

Cyclosporin A (CAS Registry Number: 59865-13-3) is a widely recognized immunosuppressive agent and naturally occurring fungal metabolite. Cyclosporin A is the first identified member of the cyclosporin family of poly-N-methylated cyclic undecapeptides having the following structure:

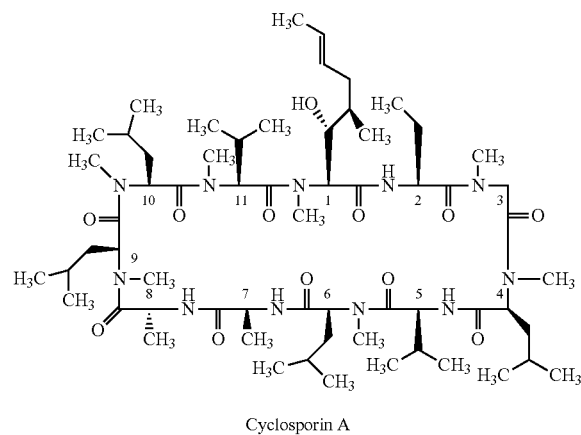 [SMILES: C/C=C/C[C@@H](C)[C@@H](O)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

Cyclosporin A

As shown by the structure above, Cyclosporin A consists of 11 amino acids and can be further represented as follows:

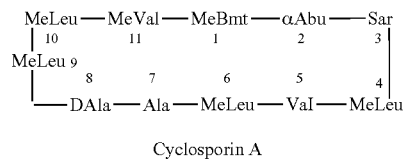

Cyclosporin A wherein:
MeBmt is (4R)-4-[(E)-2-butenyl]-4-methyl-L-threonine;
αAbu is L-α-aminobutyric acid;
Sar is sarcosine;
MeLeu is N-methyl-L-leucine;
Val is L-valine;
Ala is L-alanine;
DAla is D-alanine; and
MeVal is N-methyl-L-valine.

The numbers 1-11 are used to designate each of the eleven amino acids. Thus, for example, MeBmt is the amino acid at position 1; sarcosine, the amino acid at position 3. In certain instances, the description herein may refer to the amino acid side chain at any one of positions 1-11. The carbon to which the amino acid side chain is attached is referred to as the alpha (α) carbon.

Cyclosporin B is identical to Cyclosporin A except that αAbu is replaced by L-alanine. Cyclosporin C is identical to Cyclosporin A except that αAbu is replaced by L-threonine. Cyclosporin D is identical to Cyclosporin A except that αAbu is replaced by L-valine. Cyclosporin G is identical to Cyclosporin A except that αAbu is replaced by (S)-2-aminopentanoic acid.

Cyclosporin A is best known for its immunosuppressive properties and is commonly prescribed for use in patients that have undergone bone marrow or organ transplantation.

The intracellular receptor targets of Cyclosporin A are the cyclophilins. Cyclophilin proteins exhibit peptidyl-prolyl cis-trans isomerase (PPIase) activity, which catalyzes cis-trans isomerization of peptide bonds preceding proline, and play functional roles in chaperoning and protein folding. The immunosuppressive activity for which Cyclosporin A is so well known does not directly result from inhibiting cyclophilin activity. Rather, a Cyclosporin A-cyclophilin A complex inhibits the $Ca^{2+}$/calmodulin-dependent phosphatase calcineurin, thereby suppressing T-cell proliferation by interfering with downstream signal transduction. (See J. Lee and S. S. Kim, Journal of Experimental & Clinical Cancer Research, 2010, 29:97; J. W. Elrod and J. D. Molkentin, Circulation Journal, 2013, 77:1111; C. Piot, et al., New England Journal of Medicine, 2008, 359:473.)

The present invention relates to the surprising discovery of water-soluble, non-immunosuppressive analogs of Cyclosporin A that are potent inhibitors of cyclophilin A.

SUMMARY OF THE INVENTION

Accordingly, the present invention describes compounds of Formula I:

Formula I

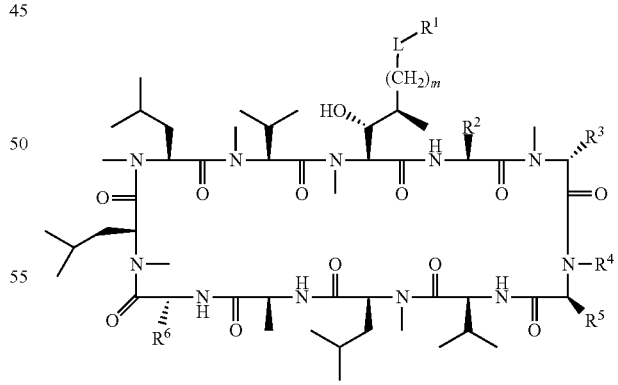

wherein:
$R^1$ is $Het^1$,
wherein $Het^1$ is a heterocyclyl optionally substituted with one or more $R^a$;
wherein each $R^a$ is independently selected from the group consisting of halogen, —$C_{1-6}$ alkyl, —$OC_{1-6}$ alkyl and —$(CH_2)_n R^b$;

wherein each $R^b$ is independently selected from $Het^2$, —$C_{1-6}$ haloalkyl, —OH, —$NH_2$, —NH($C_{1-6}$ alkyl), —N($C_{1-6}$ alkyl)$_2$ wherein each $C_{1-6}$ alkyl is the same or different, and wherein $Het^2$ is a heterocyclyl optionally substituted with one or more halogen, —$C_{1-6}$ alkyl, —$C_{1-6}$ haloalkyl, —$OC_{1-6}$alkyl, —$(CH_2)_{1-6}$OH, —$(CH_2)_{1-6}$NH$_2$, —$(CH_2)_{1-6}$NH($C_{1-6}$ alkyl) or —$(CH_2)_{1-6}$N($C_{1-6}$ alkyl)$_2$ wherein each $C_{1-6}$ alkyl is the same or different;

$R^2$ is —$CH_3$, —$CH_2CH_3$, —$CH(CH_3)_2$, —$CH_2CH_2CH_3$ or —$CH(CH_3)(OH)$;

$R^3$ is —H, —$C_{1-6}$alkyl, —$OC_{1-6}$alkyl, —$SC_{1-6}$alkyl, —$CH_2OH$, —$CH_2OCH_3$,

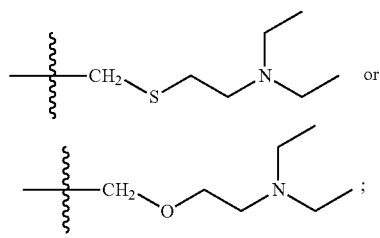

$R^4$ is —$CH_3$ or —$CH_2CH_3$;

$R^5$ is —$CH(CH_3)_2$, —$CH_2CH(CH_3)_2$, —$CH_2C(CH_3)_2$ (OH), —$CH(CH_3)(CH_2CH_3)$ or —$CH_2CH(R^c)(CH_2CH_3)$, wherein $R^c$ is $OC_{1-6}$ alkyl;

$R^6$ is —$CH_3$ or —$CH_2OH$;

L is absent or —O—$(CH_2)_p$—, wherein the oxygen atom is directly joined to the carbon atom of the $(CH_2)_m$;

m is 1, 2, 3 or 4;

n is 1, 2 or 3; and p is 0 or 1;

or a pharmaceutically acceptable salt thereof.

In another aspect, the present invention provides a pharmaceutical composition comprising a compound of Formula I and a pharmaceutically acceptable excipient, which may be an ophthalmically acceptable excipient.

In other aspects, the invention provides for a pharmaceutical composition comprising a compound of Formula I for use in treating a disease or condition, such as an inflammatory disease or condition. In some aspects, the disease or condition is dry eye.

The present invention further encompasses a method of treating a medical condition in a patient in need thereof, the method comprising administering to the patient a therapeutically effective amount of a compound of Formula I, or a pharmaceutically acceptable salt thereof, thereby treating the condition. In some forms of this method, the medical condition is selected from dry eye, dry eye disease, ocular surface inflammation, blepharitis, meibomian gland disease, allergic conjunctivitis, pterygia, ocular symptoms of graft-versus-host disease, ocular allergy, atopic keratoconjunctivitis, vernal keratoconjunctivitis, uveitis, anterior uveitis, Behcet's disease, Stevens Johnson syndrome, ocular cicatricial pemphigoid, chronic ocular surface inflammation caused by viral infection, herpes simplex keratitis, adenoviral keratoconjunctivitis, ocular rosacea and pinguecula.

In other aspects, the invention provides for a method of reducing corneal transplant rejection in a patient in need thereof, the method comprising administering to the patient a therapeutically effective amount of a compound of Formula I, or a pharmaceutically acceptable salt thereof.

In other aspects, the invention provides for a method of reducing inflammation of the eye caused by an ocular surgery, the method comprising administering to the eye(s) of a patient who has received ocular surgery a therapeutically effective amount of a compound of Formula I, or a pharmaceutically acceptable salt thereof. In other aspects, the method comprises administering a compound of Formula I or pharmaceutical composition comprising a therapeutically effective amount of the compound to the eye of the patient before, during, or after ocular surgery to reduce and/or prevent inflammation of the eye or ocular surface caused by the surgery.

In other aspects, the invention provides for a method of treating dry eye in a patient in need thereof, the method comprising administering to the eye(s) of the patient a therapeutically effective amount of a compound of Formula I, or a pharmaceutically acceptable salt thereof.

In other aspects, the invention provides for a method of increasing tear production in a patient whose tear production is suppressed or presumed to be suppressed due to ocular inflammation associated with keratoconjunctivitis sicca (dry eye disease), the method comprising administering to the eye(s) of the patient a therapeutically effective amount of a compound of Formula I, or a pharmaceutically acceptable salt thereof.

In other aspects, the invention provides for a compound of Formula I in the form of a pharmaceutical composition, which may be administered topically, orally, systemically, or by other suitable routes.

These and other aspects and advantages of the present invention may be more readily understood and appreciated with reference to the following detailed description.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulations.

It should also be noted that any carbon as well as heteroatom with unsatisfied valences in the text, Schemes, Examples and Tables herein is assumed to have the sufficient number of hydrogen atom(s) to satisfy the valences, and that any one or more of these hydrogen atoms can be deuterium.

Each and every feature described herein, and each and every combination of two or more of such features, is included within the scope of the present invention provided that the features included in such a combination are not mutually inconsistent.

As used throughout this disclosure, the following terms, unless otherwise indicated, shall be understood to have the following meanings:

The term "alkyl", as used herein, refers to saturated monovalent or divalent hydrocarbon moieties having linear or branched moieties or combinations thereof and containing 1 to 6 carbon atoms (i.e., $C_{1-6}$ alkyl). One methylene ($CH_2$) group of the alkyl can be replaced by oxygen, NH, sulfur, sulfoxide, carbonyl, carboxyl, sulfonyl, amide, sulfonamide, by a divalent $C_{3-6}$ cycloalkyl, by a divalent heterocycle, or by a divalent aryl group. One methine (CH) group of the alkyl can be replaced by nitrogen. Alkyl groups can be independently substituted by halogen, hydroxyl, cycloalkyl, amine groups, heterocyclic groups, carboxylic acid groups, phosphonic acid groups, sulphonic acid groups, phosphoric acid groups, nitro groups, amide groups and/or sulfonamide groups. Non-limiting examples of suitable alkyl groups as defined above include a $C_{1-3}$alkyl, which includes methyl (—$CH_3$), ethyl (—$CH_2CH_3$), n-propyl (—$CH_2CH_2CH_3$) and isopropyl (—$CH(CH_3)_2$).

An "alkylene" is a divalent alkyl. Non-limiting examples of an alkylene include methylene (—$CH_2$—), ethylene (—$CH_2CH_2$—) and n-propylene (—$CH_2CH_2CH_2$—).

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, —$C_{3-8}$ cycloalkyl groups, carboxylic acid groups, ester groups, ketone groups, aldehyde groups, amide groups, amine groups, sulfonamide groups and/or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups and/or hydroxyl groups.

The term "halogen", as used herein, refers to an atom of chlorine, bromine, fluorine and/or iodine.

The term "haloalkyl" refers to an alkyl in which one or more hydrogen atoms on the alkyl have been replaced with a halogen atom. Non-limiting examples of a haloalkyl include fluoroalkyls such as —$CF_3$ and —$CH_2CH_2CF_3$.

The term "heterocycle" as used herein, refers to a 3 to 10 membered ring, which can be aromatic or non-aromatic, saturated or unsaturated, containing at least one heteroatom selected from oxygen, nitrogen, sulfur, or combinations of at least two thereof, interrupting the carbocyclic ring structure. The heterocyclic ring can be interrupted by one or more C═O; the S and N heteroatoms can be oxidized. Heterocycles can be monocyclic or polycyclic. For example, a heterocycle can be bicyclic. The rings in a bicyclic or polycyclic heterocycle can be fused or non-fused. A "heterocyclyl" group is derived from a heterocycle by removal of one hydrogen. Non-limiting examples of heterocycles of the invention are substituted or unsubstituted imidazolyl, oxazolinyl, thiazolyl, pyrazolyl, pyridinyl, pyrazinyl, pyridazinyl, pyrimidinyl, benzimidazolyl, imidazo[1,2-a]pyridin-2-yl, morpholinyl, pyridinyl and pyrrolidinyl, such as substituted or unsubstituted 1H-imidazole-4-yl, 1H-imidazole-2-yl, pyrazol-4-yl, 1H-benzimidazol-2-yl, pyridin-2-yl, pyridin-4-yl, pyridin-3-yl, thiazol-4-yl, pyrimidin-2-yl, pyrazin-2-yl, 5,6,7,8-tetraimidazol[1,2-a]pyridin-2-yl, pyrazin-3-yl, pyrazol-3-yl, oxazol-2-yl, N-morpholinyl, pyridin-2-yl, pyridin-3-yl and N-pyrrolidinyl. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, sulfonamide groups, alkylamino groups, amino groups, aryl groups, $C_{3-8}$ cycloalkyl groups, hydroxyl groups and/or —$(CH_2)_nR^b$, wherein n is 1, 2 or 3 and each $R^b$ is independently selected from —OH, alkyl)$_2$ (wherein each $C_{1-6}$ alkyl is the same or different), —$C_{1-6}$ haloalkyl and unsubstituted heterocyclyl groups.

The term "alkenyl", as used herein, refers to a monovalent or divalent hydrocarbon radical having 2 to 6 carbon atoms, derived from a saturated alkyl, having at least one double bond. A $C_{2-6}$ alkenyl can be in the E or Z configuration. Alkenyl groups can be substituted by $C_{1-3}$ alkyl, as defined above, or by halogen.

The term "alkynyl", as used herein, refers to a monovalent or divalent hydrocarbon radical having 2 to 6 carbon atoms, derived from a saturated alkyl, and having at least one triple bond. Alkynyl groups can be substituted by $C_{1-3}$ alkyl, as defined above, or by halogen.

The term "aryl" as used herein, refers to an organic moiety derived from an aromatic hydrocarbon consisting of a ring containing 6 to 10 carbon atoms by removal of one hydrogen, which can be substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, carboxylic acid groups, ester groups, ketone groups, aldehyde groups, amide groups, amine groups, sulfonamide groups, $C_{3-8}$ cycloalkyl groups or hydroxyl groups. A non-limiting example of an aryl is phenyl.

The term "ketone" as used herein, represents an organic compound having a carbonyl group linked to a carbon atom such as —(CO)$R^x$, wherein $R^x$ can be alkyl, aryl, cycloalkyl, cycloalkenyl or heterocyclyl, as defined herein.

The term "aldehyde" as used herein, represents a group of formula —C(O)H.

The term "ester" as used herein, represents a group of formula —C(O)$OR^x$, wherein $R^x$ can be alkyl, aryl, cycloalkyl, cycloalkenyl or heterocyclyl, as defined herein.

The term "hydroxyl" as used herein, represents a group of formula —OH.

The term "carbonyl" as used herein, represents a group of formula —C(O)—, which may also be represented as and is equivalent to —(C═O)—.

The term "carboxyl" as used herein, represents a group of formula —C(O)O—.

The term "sulfonyl" as used herein, represents a group of formula —$SO_2$—.

The term "sulfate" as used herein, represents a group of formula —OS(O)$_2O^-$.

The term "carboxylic acid" as used herein, represents a group of formula —C(O)OH.

The term "nitro" as used herein, represents a group of formula —$NO_2$.

The term "cyano" as used herein, represents a group of formula —CN.

The term "phosphonic acid" as used herein, represents a group of formula —P(O)(OH)$_2$.

The term "phosphoric acid" as used herein, represents a group of formula —OP(O)(OH)$_2$.

The term "amide" as used herein, represents a group of formula —C(O)NR$^x$R$^y$, wherein R$^x$ and R$^y$ can be the same or independently H, alkyl, aryl, cycloalkyl, cycloalkenyl or heterocyclyl, as defined above.

The term "amine" as used herein, represents a group of formula —NR$^x$R$^y$, wherein R$^x$ and R$^y$ can be the same or independently H, alkyl, aryl, cycloalkyl, cycloalkenyl, or heterocyclyl, as defined above.

The term "sulfonamide" as used herein, represents a group of formula —S(O)$_2$NR$^x$R$^y$, wherein R$^x$ and R$^y$ can be the same or independently H, alkyl, aryl, cycloalkyl, cycloalkenyl or heterocycle, as defined above.

The term "sulfoxide" as used herein, represents a group of formula —S(O)—.

The term "sulphonic acid" as used herein, represents a group of formula —S(O)$_2$OH.

The term "substituted" means that one or more hydrogens on the designated atom is replaced with a selection from the indicated group, provided that the designated atom's normal valency under the existing circumstances is not exceeded, and that the substitution results in a stable compound.

The term "optionally substituted" means that the group can be unsubstituted or can be substituted with the specified groups, radicals or moieties.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

The term "pharmaceutically acceptable salts" refers to salts or complexes that retain the desired biological activity of the compound of Formula I and exhibit minimal or no undesired toxicological effects to the patient, animal, or cell system to which they are administered. The "pharmaceutically acceptable salts" according to the invention include therapeutically active non-toxic base or acid salt forms of Formula I.

"Solvate" refers to a physical association of a compound of this invention with one or more solvent molecules. This physical association involves varying degrees of ionic and covalent bonding, including hydrogen bonding. In certain instances the solvate will be capable of being isolated, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

"Hydrate" is a solvate wherein the solvent molecule is H$_2$O.

As used herein, the term "composition" is intended to encompass a product comprising the specified ingredients in the specified amounts, as well as any product which results, directly or indirectly, from combination of the specified ingredients in the specified amounts.

"Patient" or "subject" includes both humans and animals.

"Mammal" means humans and other mammalian animals. Non-limiting examples of a non-human mammal include a horse, pig, monkey, dog, rabbit, guinea pig, rat, or mouse.

A "patient in need of treatment" or "patient in need thereof" refers to a human or non-human mammal afflicted with a medical condition, as specified in context.

"Effective amount" or "therapeutically effective amount" is meant to describe an amount of compound or a composition sufficient to produce the desired therapeutic, ameliorative, inhibitory or preventative effect, for example, the amount sufficient to reduce the severity of one or more symptoms associated with, accompanying, or resulting from a medical condition affecting a subject.

"Treating" and "to treat" refers to relieving or reducing at least one symptom associated with or accompanying a medical condition. For example, treatment of dry eye and relief of inflammation of the ocular surface, as may occur in an individual suffering from dry eye, may be observed or experienced as an improvement in vision, and/or as a reduction in swelling, pain, redness, dryness, scratchiness, grittiness, foreign body sensation, stinging, burning, or itching. Treating an inflammation of the ocular surface or ocular surface adnexa may improve the visual performance and the optical quality of the eye. Improvement in visual performance may include improved optical quality, improved tear film production, secretion, quality, and/or stability, reduced blurring, improved central and/or peripheral field vision, improved visual performance, acuity, or perception, and/or reduced blinking frequency. The symptom(s) positively affected by the treatment, will depend on the particular condition.

The term "inflammation" refers to the biological response of the living body to injury or other harmful insults. Symptoms of "an inflammation at the ocular surface" can include redness, swelling, heat, pain, and/or loss of function of glands or tissue in the ocular surface or ocular surface adnexa. Other symptoms may include sensations of (and lead a patient to complain of) dryness, burning, itching, or scratchiness. A subject may report a feeling of dust, dirt, sand, or gravel in the eye.

A "medical condition" refers to a deviation from or interruption of the normal structure or function of any body part, tissue, organ, or system and that is characterized by an identifiable group of signs or symptoms whose etiology, pathology, and prognosis may be known or unknown. A medical condition of a body part, tissue, organ, or system of a human or non-human mammal may result from various causes, including but not limited to injury, surgical trauma, infection, nutritional deficiency, genetic defect, exposure to toxins or radiation, and environmental stress. Medical conditions include ocular conditions such as, for example, inflammation of the ocular surface, and dry eye; and dermatological conditions such as an inflammation of the skin.

An "ocular condition" is a disease, ailment or condition which affects or involves the eye or one or more parts or regions of the eye.

The term "ocular surface" refers to the cornea, the corneal epithelium, the conjunctiva (palpebral, bulbar, and forniceal), the conjunctival blood vessels, Tenon's capsule, the sclera, and the limbus.

"Ocular surface condition" refers to a medical condition that affects or involves one or more parts, regions, or tissues of the ocular surface. An ocular surface condition can be an inflammation of an ocular surface tissue, and includes an acute, chronic, and surgically-induced inflammation of an ocular surface tissue.

The term "ocular surface adnexa" refers to structures in close proximity to the ocular surface, including the lacrimal gland, the eye lids, eyelashes, and eyebrows, the orbital wall, the periocular or extraocular muscles, and the meibomian glands.

The "eye" is the sense organ for sight, and includes the eyeball, or globe, the orbital sense organ that receives light and transmits visual information to the central nervous system. Broadly speaking the eye includes the eyeball and the tissues and fluids which constitute the eyeball, the periocular muscles (such as the oblique and rectus muscles) and the portion of the optic nerve which is within or adjacent to the eyeball.

The "eye lids" are the structures covering the front of the eye that protect it, limit the amount of light entering the pupil, and help distribute tear film over the exposed corneal surface.

The term "biocompatible" means compatible with living tissue or a living system by not being toxic, injurious, or physiologically reactive and by causing minimal or no immunological reaction.

The present invention includes the compound of Formula I in all its isolated forms. Thus, for example, the compound of Formula I is intended to encompass all forms of the compound such as, for example, any solvates, hydrates, stereoisomers, tautomers, etc. The present invention further includes pharmaceutically acceptable salts of any compound having Formula I.

The present invention further includes the compound of Formula I in its purified form. A compound of Formula I can be in a purified form. In one embodiment, the purified form is the form obtained from medium pressure liquid chromatography (MPLC).

One or more compounds of the invention may exist in unsolvated as well as solvated forms with pharmaceutically acceptable solvents such as water, ethanol, and the like, and it is intended that the invention embrace both solvated and unsolvated forms.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example, infrared spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, or formic acid and the like (Handbook of Pharmaceutical Salts, P. Heinrich Stahl & Camille G. Wermuth (Eds), Verlag Helvetica Chimica Acta, Zürich, 2002, 329-345).

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use (2002) Zurich: Wiley-VCH; S. Berge et al, Journal of Pharmaceutical Sciences (1977) 66(1), 1-19; P. Gould, International J. of Pharmaceutics (1986) 33, 201-217; Anderson et al, The Practice of Medicinal Chemistry (1996), Academic Press, New York; and in The Orange Book (Food & Drug Administration, Washington, D.C. on their website).

The base addition salt form of a compound of Formula I that occurs in its free form as an acid can be obtained by treating the acid with an appropriate base such as an inorganic base, for example, sodium hydroxide, magnesium hydroxide, potassium hydroxide, calcium hydroxide, ammonia and the like; or an organic base such as for example, L-arginine, ethanolamine, betaine, benzathine, morpholine and the like. (Handbook of Pharmaceutical Salts, P. Heinrich Stahal & Camille G. Wermuth (Eds), Verlag Helvetica Chemica Acta, Zürich, 2002, 329-345).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

It is also possible that the compound of Formula I may exist in different tautomeric forms, and all such forms are embraced within the scope of the invention. Also, for example, all keto-enol, amide or imino ether, and imine-enamine forms of the compounds are included in the invention.

The compounds of Formula I and some of their intermediates have at least one asymmetric center in their structure. This asymmetric center (or chiral center) may be present in an R or S configuration, said R and S notation is used in correspondence with the rules described in Pure Appl. Chem. (1976), 45, 11-13. Thus, the compounds of Formula I may exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures thereof, are embraced within the scope of the invention.

Diastereomeric mixtures can be separated into their individual diastereomers on the basis of their physico-chemical property differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column. Also, some of the compounds of the invention may be atropisomers (e.g., substituted biaryls) and are considered as part of this invention.

In particular, a skilled person will realize that even if the absolute stereochemistry of a particular stereoisomer (e.g., an enantiomer or diastereomer) of a molecule is not known, that particular stereoisomer can be distinguished from the other stereoisomers by use of other techniques (e.g., polarimetry, nuclear magnetic resonance spectroscopy, chromatography, and others identifiable to a skilled person). In particular, one exemplary method of distinguishing stereoisomers when the absolute stereochemistry of each stereoisomer is not known is chromatography, such as flash chromatography, medium pressure chromatography, or high pressure liquid chromatography (HPLC). In particular, two or more stereoisomers such as diastereomers can be separated and characterized by their retention times, which would be expected to be replicable by using the same chromatographic conditions (e.g., flow rate, column material, solvent systems/gradient profiles, and/or others identifiable to a skilled person). In particular, a skilled person will realize that even when the exact relative retention times of one or more stereoisomers is not replicated (e.g., due to slight variations in the chromatographic parameters and/or chromatographic equipment), a stereoisomer with a shorter retention time can be said to be "faster eluting," "earlier eluting" or having a "high Rf," and a stereoisomer with a longer retention time can be said to be "slower eluting," "later eluting or having a "low Rf." A skilled person will realize that once two or more stereoisomers are distinguished by a technique such as chromatography, the absolute stereochemistry of the stereoisomers can be determined by techniques or combinations of techniques identifiable to a skilled person (e.g., X-ray crystallography, vibrational circular dichroism, nuclear magnetic resonance, total synthesis, and others identifiable to a skilled person).

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The use of the terms "salt", "solvate", and the like, is intended to equally apply to the salt and solvate of enantiomers, stereoisomers, rotamers, tautomers, positional isomers, or racemates of the inventive compounds.

Pharmaceutical Compositions

The present invention further concerns the use of a compound of Formula I, or a pharmaceutically acceptable salt thereof, for the manufacture of a pharmaceutical composition.

The present invention includes pharmaceutical compositions comprising, consisting of, or consisting essentially of a compound having Formula I, or a pharmaceutically acceptable salt thereof, in combination with one or more pharmaceutically acceptable excipients. A "pharmaceutically acceptable excipient" is one that is compatible with the compound of Formula I and that is not harmful to the person receiving the pharmaceutical composition. Mixtures of two or more of such suitable excipients may be used. A pharmaceutical composition may comprise one, two or more compounds having Formula I, or one, two or more salts thereof, or combinations thereof. A pharmaceutically acceptable excipient may improve the stability or effectiveness of the composition.

Pharmaceutical compositions of the present invention can be in the form of a liquid (such as an aqueous solution), solid, gel, suspension or emulsion, or other suitable form.

Pharmaceutical compositions of the present invention can be sterilized and therefore prepared in sterile form for pharmaceutical use.

The pharmaceutical composition may be prepared in a unit dosage form suitable for oral, parenteral, topical or intraocular administration to a patient.

For ocular applications, including but not limited to topical administration to the eye, pharmaceutical compositions may be prepared by combining a therapeutically effective amount of a compound of Formula I, or a pharmaceutically acceptable salt thereof, as an active ingredient, with one or more pharmaceutically acceptable excipients. The excipient is preferably ophthalmically acceptable, that is, it causes little or no injury to the eye. The pharmaceutical composition may be prepared in an aqueous liquid or emulsion form suitable for topical application to the eye(s) of the patient.

A therapeutically effective amount of a compound of Formula I can be from about 0.001% (w/v) to about 5% (w/v), from about 0.001% (w/v) to about 1.0% (w/v), from about 0.01% (w/v) to about 0.5% (w/v), from about 0.1% to about 0.5% (w/v), or from about 0.5% to about 1% (w/v) in liquid and emulsion formulations.

The actual dose of the active compounds of the present invention depends on the specific compound, and on the condition to be treated. The actual amount of compound to be administered in any given case will be determined by a physician taking into account the relevant circumstances, such as the severity of the condition, the age and weight of the patient, the patient's general physical condition, the cause of the condition, and the route of administration.

Pharmaceutically acceptable excipients for use with the invention include but are not limited to preservatives, buffering agents, antioxidants, lipophilic vehicles, hydrophilic vehicles, tonicity agents, electrolytes, thickeners, neutralizing agents, emulsifiers, dispersing agents, demulcents, plasticizers, occlusive agents, and film formers, and combinations thereof. Certain compositions may include both a buffer component and a tonicity component.

Useful preservatives include benzalkonium chloride, PURITE®, sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, methyl and ethyl parabens, methylparaben, polyvinyl alcohol, benzyl alcohol, phenylethanol, hexetidine, chlorite components, such as stabilized chlorine dioxide, metal chlorite, and other ophthalmically acceptable preservatives. The concentration of the preservative component, if any, in the present compositions is a concentration effective to preserve the composition, and is often in a range of about 0.00001% to about 0.05% or about 0.1% (w/w) of the composition.

Acceptable buffering agents include HEPES and those prepared from a suitable combination of the acid and/or base forms of acetates, citrates, phosphates, carbonates, succinates, and borates. Phosphate buffers may be composed of sodium phosphate dibasic and sodium phosphate monobasic. Buffering agents may be provided in any of the compositions in an amount effective to control the pH of the composition. The pH of the composition can be in a range of about 6 to about 8, about 7 to about 8, about 7 to about 7.6, or about 7.5 to about 8.

Useful tonicity agents include glycerin, sugar alcohols, xylitol, sorbitol, glycerol, erythritol, mannitol, salts, potassium chloride and/or sodium chloride. Tonicity agents may be provided in an amount effective to control the tonicity or osmolality of the compositions. The osmolality of the composition can be in a range of about 200 to about 400, or about 250 to about 350, mOsmol/kg. In one embodiment, the composition is isotonic. An isotonic solution is a solution that has the same solute concentration as that inside normal cells of the body and the blood. An isotonic solution in contact with a cell produces no net flow of water across the cell membrane.

Useful lipophilic vehicles include castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, cetyl alcohols, and stearyl alcohols.

Useful hydrophilic vehicles include water.

Emulsions may be prepared by combining a compound of Formula I in a sterile lipophilic vehicle or fixed oil. The lipophilic vehicle or fixed oil may be selected from the group consisting of synthetic mono- and diglycerides, fatty acids (including oleic acid), naturally occurring vegetable oils, sesame oil, coconut oil, peanut oil, cottonseed oil, castor oil, olive oil, mineral oil, synthetic fatty vehicles, and ethyl oleate. Buffers, emulsifiers, dispersing agents, preservatives, antioxidants, and the like can be incorporated as required.

A pharmaceutical composition may optionally comprise an acceptable amount of dimethyl sulfoxide as an excipient.

Additional examples of excipients that may be optionally included in the pharmaceutical compositions of the present invention are listed in Table A.

TABLE A

| Function | Ingredient |
| --- | --- |
| Active | Compound of Formula I |
| Thickener or polyelectrolyte | carbomer, sodium carboxymethylcellulose, methylcellulose, hydroxypropyl methylcellulose, polyvinyl alcohol, xanthan gum |
| Neutralizing Agent | sodium hydroxide, organic bases |
| Emulsifier or dispersing agent | polysorbate 20, polysorbate 40, polysorbate 60, polysorbate 80, POE-40-stearate, Pemulen ® and other polymeric emulsifiers. |
| Lipophilic Vehicle | castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, cetyl alcohols, stearyl alcohols |
| Buffering Agent | sodium citrate dihydrate, boric acid, monosodium phosphate, monohydrate, sodium phosphate dibasic heptahydrate, sodium phosphate monobasic monohydrate, HEPES |
| Tonicity Agent | Glycerin, erythritol, mannitol, potassium chloride, sodium chloride, |
| Demulcent | carboxymethylcellulose sodium, hydroxypropyl methylcellulose hydroxyethyl cellulose, methylcellulose, polyvinyl alcohol, povidone, glycerin, propylene glycol, PEG 300, PEG 400 |
| Preservative | benzalkonium chloride, PURITE ®, and other ophthalmic preservatives |
| Plasticizer | Silicone oils, isostearyl alcohol, cetyl alcohol, glycerin |
| Occlusive Agent | silicone oils, petrolatum, waxes |
| Film Former | acrylate/octylacrylamide copolymer, poly(ethyl acrylate, methyl methacrylate), chitosan, polyvinyl alcohol, polyisobutylene, polyvinylpyrrolidone-vinyl acetate copolymer, silicon gum, polyvinylpyrrolidone, other sustained release polymeric films |
| Hydrophilic Vehicle | water |

U.S. Pat. No. 5,474,979, the entire contents of which are incorporated herein by reference, provides examples of emulsions that may be used to prepare pharmaceutical compositions of the present invention.

Therapeutic Uses and Methods of Treatment

The present invention is directed in part to the use of a compound of Formula I, or a pharmaceutical composition comprising a compound of Formula I, for the treatment of a disease or condition. The disease or condition may be an inflammatory disease or condition. The inflammatory disease or condition may be secondary to a primary disease or condition.

A compound of Formula I, or a pharmaceutical composition comprising a compound of Formula I, may be used to treat dry eye, dry eye disease (i.e., keratoconjunctivitis sicca), ocular surface inflammation (i.e, inflammation of the ocular surface), blepharitis, meibomian gland disease, allergic conjunctivitis, pterygium, ocular symptoms of graft-versus-host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, adenoviral keratoconjunctivitis, ocular rosacea, and/or pinguecula, or to prevent or reduce the risk of corneal transplant rejection in a patient or subject in need thereof. Additionally, in one embodiment of this invention there is provided a method for administering a compound or pharmaceutical composition of this invention to a patient before, during, or after ocular surgery (such as refractive surgery) to reduce and/or prevent inflammation of the eye or ocular surface caused by the surgery.

Compounds or pharmaceutical compositions of the invention may be used to treat an inflammation of the ocular anterior segment of the eye. More specifically, the compounds or pharmaceutical compositions of the invention may be used to treat an inflammation of the ocular surface or ocular surface adnexa.

In one embodiment, there is provided a method for reducing or preventing an ocular condition in a subject in need thereof, the method comprising administering a therapeutically effective amount of a compound of Formula I, or a pharmaceutical composition comprising a compound of Formula I, to the eye(s) of the subject. The method may reduce one or more signs or symptoms of the ocular condition.

In another embodiment, there is provided a method for increasing tear production in a patient whose tear production is suppressed (or presumed to be suppressed) due to ocular inflammation associated with keratoconjunctivitis sicca (dry eye disease), the method comprising administering a therapeutically effective amount of a compound of Formula I, or a pharmaceutical composition comprising a compound of Formula I, to the eye(s) of the subject.

In another embodiment, there is provided a method for reducing ocular surface inflammation in a subject in need thereof, the method comprising administering a therapeutically effective amount of a compound of Formula I, or a pharmaceutical composition comprising a compound of Formula I, to the eye(s) of the subject. In one particular method, the ocular surface inflammation is associated with keratoconjunctivitis sicca (dry eye disease). In further embodiments of this method, the compound having Formula I is administered topically to the subject's eye(s).

In another embodiment there is provided a method for treating dry eye in a subject in need thereof, the method comprising administering a compound of Formula I, or a pharmaceutical composition comprising a compound of Formula I, to the eye(s) of the subject. In a further embodiment, there is provided a method for treating dry eye in a subject in need thereof, the method comprising administering a therapeutically effective amount of a compound of Formula I, or a pharmaceutical composition comprising a compound of Formula I, to the eye(s) of the subject.

"Dry eye" as used herein includes "dry eye disease" as defined by the International Dry Eye Workshop (DEWS) in Lemp et al. (2007) "The Definition and Classification of Dry Eye Disease: Report of the Definition and Classification Subcommittee of the International Dry Eye Workshop" *Ocul. Surf.* 5:75-92. The International Dry Eye Workshop (DEWS) defines dry eye disease as "a multifactorial disease of the tears and ocular surface that results in symptoms of discomfort, visual disturbance, and tear film instability with potential damage to the ocular surface, accompanied by increased osmolarity of the tear film and inflammation of the ocular surface."

The term "dry eye disease" is considered to be synonymous with "dry eye syndrome" and "keratoconjunctivitis sicca." Dry eye disease includes the aqueous deficient (Sjogren and non-Sjogren) and evaporative categories of dry eye disease. An individual subject with dry eye disease may present with symptoms of both aqueous deficiency (e.g., insufficient tear production) and excessive evaporation of the tear film.

A compound of Formula I, or pharmaceutical composition comprising a compound of Formula I, can be administered to a subject topically, orally, or systemically (including intravenously or intra-arterially). Administration may be to the eye of the subject, such as the surface of the eye of the subject.

The actual amount of the compound to be administered in any given case will be determined by a physician taking into account the relevant circumstances, such as the severity of the condition, the age and weight of the subject, the subject's general physical condition, the cause of the condition, and the route of administration.

Accordingly, the present invention includes methods for treating any of the above ocular conditions in a patient in need thereof by administering a therapeutically effective amount of a compound of Formula I, or a pharmaceutical composition comprising a therapeutically effective amount of a compound of Formula I, to the patient, for example, to the eye(s) of the patient. The compound or composition can be administered directly to the ocular surface of the eye or to an ocular region in the eye. Modes of direct administration to the eye can include topical delivery and intraocular injection.

Pharmaceutical compositions of the invention may also be used to restore corneal sensitivity that has been impaired, for example, due to surgery on the cornea or other surface of the eye. Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients may actually be a form of corneal neuropathy that results when corneal nerves are severed by surgery or inflamed after viral infection.

A patient in need of treatment of an "ocular surface inflammation" or more specifically "dry eye" may complain of superficial scratchy pain, abrasiveness, eye dryness, foreign body sensation, scratchiness, ocular discomfort, ocular pain, burning, itching, decreased vision, visual blurriness or cloudiness, irritation or pain from bright light, or decreased visual acuity. Dryness may be experienced and reported as a feeling that moisture is absent, foreign body sensation, and/or as a feeling of dust, sand, or gravel in the eye. Accordingly, a patient with dry eye may experience one or more of the following symptoms: stinging and/or burning, dryness, sensation of foreign body (gritty or sandy feeling), itching, sensitivity to light, pain or soreness, intermittent blurred vision, tired or fatigued eyes, and frequent blinking.

Dry eye may be due to inadequate tear production, a disruption in tear secretion, decreased tear film quality, or excessive evaporation of the tear film at the ocular surface, any and all of which can lead to sensations of dry eye and eye dryness and/or be associated with dry eye disease.

An individual subject having dry eye may exhibit one or more of the characteristics or symptoms associated with dry eye disease (keratoconjunctivitis sicca). Methods for diagnosing and monitoring dry eye disease may include those described in Bron et al. (2007) "Methodologies to Diagnose and Monitor Dry Eye Disease: Report of the Diagnostic Methodology Subcommittee of the International Dry Eye WorkShop (2007)" *Ocul. Surf.* 5(2):108-152, and can include, but are not necessarily limited to, symptom questionnaires developed for use in dry eye diagnosis, the fluorescein tear film break up test, ocular surface staining grading with fluorescein/yellow filter, the Schirmer test, and tear osmolarity measurement.

A common feature of dry eye disease is an unstable tear film due to abnormal or deficient tear production, increased tear evaporation, or imbalance of tear components. An unstable tear film may lead to or promote inflammation of the ocular surface (Pflugfelder et al. 2004, Am. J. Ophthalmol. 137:337-342).

An individual subject suffering from or in need of treatment of "dry eye," to which the present invention may be directed, can be one who presents with, is suffering from, or exhibits one or more symptoms of dry eye disease, or ocular surface dryness, or eye dryness, which depending on the individual may include sensations of dry eye (i.e., sensations of eye dryness), tear film instability, decreased tear secretion, delayed clearance, and altered tear composition, or tear hyperosmolarity.

For purposes of the present invention, "dry eye" treatable with one or more compounds of Formula I, or pharmaceutical compositions comprising one or more compounds of Formula I, may be chronic or temporary, may occur in one or both eyes of an individual, and in particular patients may be due to or caused by changes in physiological condition; use of contact lenses; allergy to a medication; in response to an external environmental factor such as pollen, dust, particulates, or low humidity; due to a side effect of a medication; aging; low blink rate; vitamin A deficiency; a chemical burn; radiation; blepharitis; rosacea; reaction to the use of preservative-containing topical eye drops, such as wetting drops; disorders of the lid; aperture; meibomian oil deficiency; lacrimal deficiency; disruption or damage of the lacrimal gland or obstruction of the lacrimal gland duct; reflex block; infection; changes in hormonal balance; eye surgery, including but not limited to refractive laser eye surgery, including LASIK, LASEK, and PRK; or as a result of exposure to an environmental contaminant encountered during a recreational or occupational activity; or as a result of physical injury to the eye. Accordingly, compounds or pharmaceutical compositions of the present invention may be used to reduce the severity of one or more symptoms associated with or accompanying dry eye.

In particular patients suffering from dry eye disease, to which the present method may be directed, the dry eye disease can be caused by nutritional disorders or deficiencies (including vitamins), pharmacologic side effects, eye stress and glandular and tissue destruction, environmental exposure to smog, smoke, excessively dry air, airborne particulates, autoimmune and immunodeficient disorders, and may be prevalent in patients who are unable to blink.

In other forms, the present invention may be directed to treating dry eye associated with rheumatoid arthritis, lupus erythematosus, polymyositis, rosacea, scleroderma, polyarteritis, thyroiditis, hepatobiliary disease, lymphoma, pulmonary fibrosis, macroglobulinemia, or coeliac disease.

Blepharitis is a disorder of the meibomian glands, which produce the lipid component of tear film. Both the upper and lower eye lids contain 30-40 glands, located beneath the skin. The glandular pores open just behind the base of the eye lashes on the eye lid margin. With blepharitis, the glands become inflamed and the pores become blocked. Symptoms of blepharitis include eye irritation, soreness, redness and an accumulation of matter on the eyelids. Patients may also experience dry eye as well. Patients suffering from blepharitis may complain of a sandy or itchy feeling of their eyes. There is usually redness, thickening, and irregularity of the lid margins. Accordingly, blepharitis involves an inflammation of the eye lid margins. Blepharitis can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary, hyperplasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, fornix foreshortening, trichiasis, entropion, and madarosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA-DR.sup.+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

Uveitis, the inflammation of the uvea, is responsible for about 10% of the visual impairment in the United States. Phacoanaphylactic endophthalmitis is a human autoimmune disease. Panuveitis refers to inflammation of the entire uveal (vascular) layer of the eye. Posterior uveitis generally refers to chorioretinitis, and anterior uveitis refers to iridocyclitis. The inflammatory products (i.e., cells, fibrins, excess proteins) of these inflammations are commonly found in the fluid spaces of the eye, i.e., the anterior chamber, posterior chamber and vitreous space, as well as infiltrating the tissue intimately involved in the inflammatory response. Uveitis may occur following surgical or traumatic injury to the eye; as a component of an autoimmune disorder, such as rheumatoid arthritis, Behcet's disease, ankylosing spondylitis, and sarcoidosis; as an isolated immune mediated ocular disorder, such as pars planitis, iridocyclitis etc., unassociated with known etiologies; and following certain systemic diseases which cause antibody-antigen complexes to be deposited in the uveal tissues. Together these disorders represent the non-infectious uveitis.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Uveitis is a prominent feature of Behcet's disease, a multi-system inflammatory disorder also characterized by oral and genital ulcers, cutaneous, vascular, joint, and neurological manifestations.

Rosacea is a chronic and common skin disorder with no identified cause or cure. The pathogenesis of rosacea is thought to have multiple factors. Possible factors include exposure to the demodex folliculorum mite, gastrointestinal disease or a vasodilation disorder, and other triggers such as diet or sunlight. Patients may present with a variety of symptoms, including inflammatory papules, edema, telangiectasia, rhinophyma and ocular symptoms.

The ocular signs of rosacea include blepharitis, including anterior blepharitis, conjunctivitis, iritis, iridocyclitis, keratitis, meibomian gland dysfunction, telangiectasia, erythema, chalazion, hordeolum, interpalpebral hyperemia, conjunctival hyperemia, ciliary base injection, bulbar injection, crusts, sleeves, and superficial punctuate keratopathy. The ocular symptoms are nonspecific and may include burning, tearing, decreased tear secretion, redness, and foreign body or gritty or dry sensation, irritation, itchiness, blurred vision, photosensitivity, watery eyes, bloodshot eyes, burning, telangiectasia, irregularity of the lid margins, and meibomian gland dysfunction.

Pinguecula is a benign, yellowish brown proliferative growth that forms on the conjunctiva. Pinguecula may cause irritation and scratchiness of the eye, dry eye, inflammation of the conjunctiva and effect appearance of the eye. Inflamed pinguecula, which cause ocular irritation or become unsightly, may require surgical removal. However, the post-operation scar may be as cosmetically objectionable as the pinguecula, and pinguecula regrowth may occur following surgical removal.

Allogeneic bone marrow transplantation (BMT) is a well-established treatment for malignant and non-malignant hematological diseases, and is performed in tens of thousands of patients each year. Mature donor T cells within the stem cell graft are the main mediators of the beneficial immune effects, but they are also responsible for the induction of graft-versus-host disease (GVHD), the major cause of morbidity and mortality in BMT patients. GVHD occurs when transplanted donor-derived T cells recognize proteins expressed by recipient antigen-presenting cells. Consequently, this recognition induces donor T-cell activation, proliferation, and differentiation, leading to a cellular and inflammatory attack on recipient target tissues. Acute or chronic GVHD occurs within a 100-day period post-BMT that leads to dermatitis, enteritis, and hepatitis. Ocular symptoms include blurry vision, foreign body sensation, burning sensation, severe light sensitivity, chronic conjunctivitis, dry eye, and eye pain.

In other aspects of the present invention, a compound of Formula I or a pharmaceutical composition comprising a compound of Formula I may be used to reduce one or more symptoms associated with an inflammatory dermatological condition; one example of an inflammatory dermatological condition that may be treated is psoriasis.

Accordingly, in one embodiment there is provided a method for reducing one or more symptoms associated with an inflammatory dermatological condition in a patient in need thereof, the method comprising administering a compound of Formula I or a pharmaceutical composition comprising a compound of Formula I to the patient. In another embodiment there is provided a method for reducing or preventing an inflammatory dermatological condition in a patient, the method comprising administering a therapeutically effective amount of a compound of Formula I or a pharmaceutical composition comprising a therapeutically effective amount of a compound of Formula I to the patient. The method may reduce one or more signs or symptoms of the inflammatory dermatological condition. In a further embodiment, the inflammatory dermatological condition being treated is psoriasis.

In another embodiment there is provided a method for treating an inflammation of the skin in a patient in need thereof, the method comprising administering a compound of Formula I or a pharmaceutical composition comprising a compound of Formula I to the patient. In another embodiment there is provided a method for reducing an inflammation of the skin in a patient, the method comprising administering a therapeutically effective amount of a compound of Formula I, or a pharmaceutical composition comprising a therapeutically effective amount of a compound of Formula I, to the patient.

Additionally, a pharmaceutical composition comprising a compound of Formula I may be used to treat a viral infection; examples of viral infections that may be treated include Hepatitis C infection and Hepatitis B infection.

Accordingly, in one embodiment there is provided a method of treating a viral infection in a patient in need thereof, the method comprising administering a pharmaceutical composition comprising a compound of Formula I to the patient. In another embodiment there is provided a method for reducing one or more signs or symptoms of a viral infection, or for inhibiting the progress of a viral infection in a patient in need thereof, the method comprising administering a pharmaceutical composition comprising a compound of Formula I to the patient.

The following are non-limiting embodiments of the invention.

In embodiment (1), there is provided a compound of Formula I:

Formula I

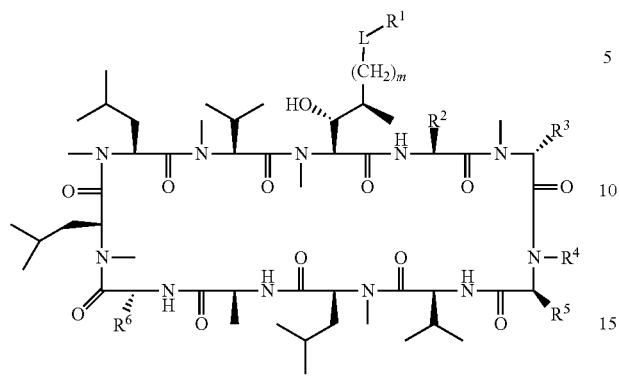

wherein:
R¹ is Het¹,
  wherein Het¹ is a heterocyclyl optionally substituted with one or more $R^a$;
  wherein each $R^a$ is independently selected from the group consisting of halogen, —$C_{1-6}$ alkyl, —$OC_{1-6}$ alkyl and —$(CH_2)_nR^b$;
  wherein each $R^b$ is independently selected from Het², —$C_{1-6}$ haloalkyl, —OH, —$NH_2$, —$NH(C_{1-6}$ alkyl), —$N(C_{1-6}$ alkyl$)_2$ wherein each $C_{1-6}$ alkyl is the same or different; and
  wherein each Het² is independently a heterocyclyl optionally substituted with one or more halogen, —$C_{1-6}$ alkyl, —$C_{1-6}$ haloalkyl, —$(CH_2)_{1-6}OH$, —$(CH_2)_{1-6}NH_2$, —$(CH_2)_{1-6}NH(C_{1-6}$ alkyl) or —$(CH_2)_{1-6}N(C_{1-6}$ alkyl$)_2$ (wherein each $C_{1-6}$ alkyl is the same or different);
R² is —$CH_3$, —$CH_2CH_3$, —$CH(CH_3)_2$, —$CH_2CH_2CH_3$ or —$CH(CH_3)(OH)$;
R³ is —H, —$C_{1-6}$alkyl, —$OC_{1-6}$alkyl, —$SC_{1-6}$alkyl, —$CH_2OH$, —$CH_2OCH_3$,

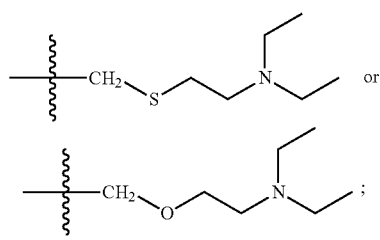

R⁴ is —$CH_3$ or —$CH_2CH_3$;
R⁵ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
R⁶ is —$CH_3$ or —$CH_2OH$;
L is absent or —O—$(CH_2)_p$—, wherein the oxygen atom is directly joined to the carbon atom of the $(CH_2)_m$;
m is 1, 2, 3 or 4;
n is 1, 2 or 3; and
p is 0 or 1;
or a pharmaceutically acceptable salt thereof.

In embodiment (1a), Het¹ is optionally substituted with $(R^a)_q$, wherein q is 0, 1, 2, 3 or 4 (i.e., Het¹ has 0, 1, 2, 3 or 4 $R^a$ substituents).

In embodiment (2), there is provided a compound of embodiment (1), wherein m is 1 and L is absent.

In embodiment (3), there is provided a compound of embodiment (1) or (2) having the following structure:

Formula VIII

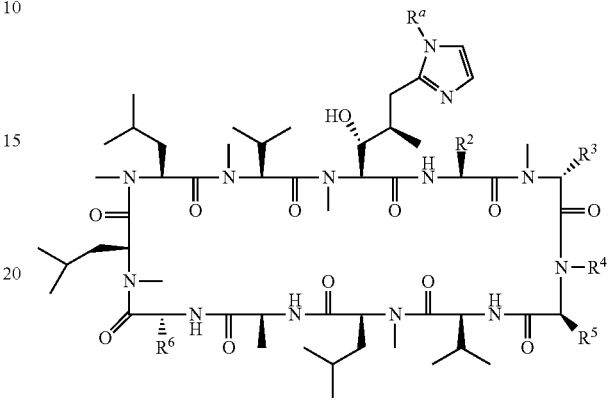

wherein:
$R^a$ is selected from the group consisting of halogen, —$C_{1-6}$ alkyl, —$OC_{1-6}$ alkyl and —$(CH_2)_nR^b$;
  wherein $R^b$ is selected from Het², —$C_{1-6}$ haloalkyl, —OH, —$NH_2$, —$NH(C_{1-6}$ alkyl), —$N(C_{1-6}$alkyl$)_2$ wherein each $C_{1-6}$ alkyl is the same or different; and
  wherein Het² is a heterocyclyl optionally substituted with one or more halogen, —$C_{1-6}$ alkyl, —$C_{1-6}$ haloalkyl, —$(CH_2)_{1-6}OH$, —$(CH_2)_{1-6}NH_2$, —$(CH_2)_{1-6}NH(C_{1-6}$ alkyl) or —$(CH_2)_{1-6}N(C_{1-6}$ alkyl$)_2$ (wherein each $C_{1-6}$ alkyl is the same or different);
R² is —$CH_3$, —$CH_2CH_3$, —$CH(CH_3)_2$, —$CH_2CH_2CH_3$ or —$CH(CH_3)(OH)$;
R³ is —H, —$C_{1-6}$alkyl, —$OC_{1-6}$alkyl, —$SC_{1-6}$alkyl, —$CH_2OH$, —$CH_2OCH_3$,

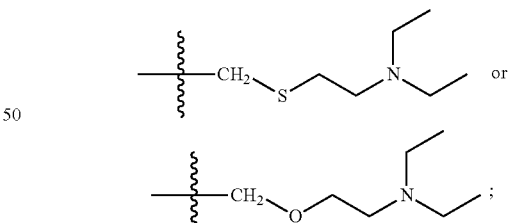

R⁴ is —$CH_3$ or —$CH_2CH_3$;
R⁵ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
R⁶ is —$CH_3$ or —$CH_2OH$; and
n is 1, 2 or 3;
or a pharmaceutically acceptable salt thereof.

In embodiment (4), there is provided a compound of embodiment (1) or (2) having the following structure:

Formula V

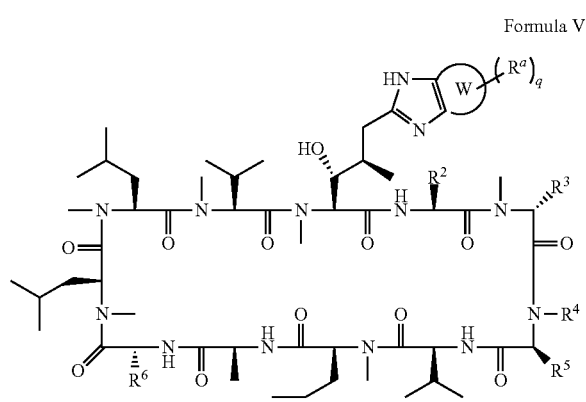

wherein:
W is a 5- or 6-membered cycloalkyl, cycloalkenyl or heterocyclic ring;
each $R^a$ is independently selected from the group consisting of halogen, —$C_{1-6}$ alkyl, —$OC_{1-6}$ alkyl and —$(CH_2)_nR^b$;
wherein each $R^b$ is independently selected from $Het^2$, —$C_{1-6}$ haloalkyl, —OH, —$NH_2$, —$NH(C_{1-6}$ alkyl), —$N(C_{1-6}$ alkyl)$_2$ wherein each $C_{1-6}$ alkyl is the same or different, and
wherein each $Het^2$ is independently a heterocyclyl optionally substituted with one or more halogen, —$C_{1-6}$ alkyl, —$C_{1-6}$ haloalkyl, —$(CH_2)_{1-6}OH$, —$(CH_2)_{1-6}NH_2$, —$(CH_2)_{1-6}NH(C_{1-6}$ alkyl) or —$(CH_2)_{1-6}N(C_{1-6}$ alkyl)$_2$ (wherein each $C_{1-6}$ alkyl is the same or different);
$R^2$ is —$CH_3$, —$CH_2CH_3$, —$CH(CH_3)_2$, —$CH_2CH_2CH_3$ or —$CH(CH_3)(OH)$;
$R^3$ is —H, —$C_{1-6}$alkyl, —$OC_{1-6}$alkyl, —$SC_{1-6}$alkyl, —$CH_2OH$, —$CH_2OCH_3$,

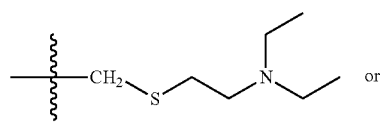

$R^4$ is —$CH_3$ or —$CH_2CH_3$;
$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
$R^6$ is —$CH_3$ or —$CH_2OH$;
n is 1, 2 or 3;
q is 0, 1, 2, 3 or 4; and
wherein the dashed line is a double or single bond;
or a pharmaceutically acceptable salt thereof.

In embodiment (5), there is provided a compound of embodiment (1) or (2) having the following structure:

Formula IX

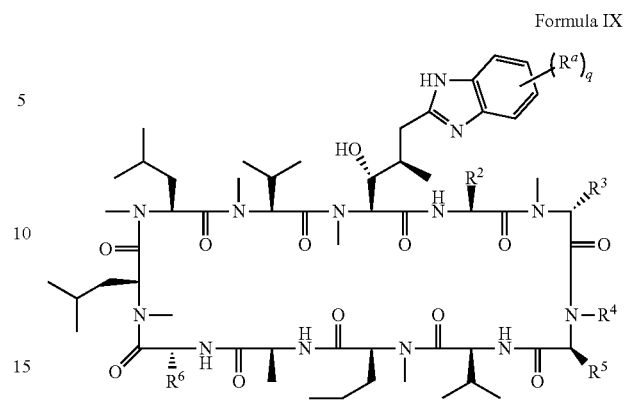

wherein:
each $R^a$ is independently selected from the group consisting of halogen, —$C_{1-6}$ alkyl, —$OC_{1-6}$ alkyl and —$(CH_2)_nR^b$;
wherein each $R^b$ is independently selected from $Het^2$, —$C_{1-6}$ haloalkyl, —OH, —$NH_2$, —$NH(C_{1-6}$ alkyl), —$N(C_{1-6}$ alkyl)$_2$ wherein each $C_{1-6}$ alkyl is the same or different, and
wherein each $Het^2$ is independently a heterocyclyl optionally substituted with one or more halogen, —$C_{1-6}$ alkyl, —$C_{1-6}$ haloalkyl, —$(CH_2)_{1-6}OH$, —$(CH_2)_{1-6}NH_2$, —$(CH_2)_{1-6}NH(C_{1-6}$ alkyl) or —$(CH_2)_{1-6}N(C_{1-6}$ alkyl)$_2$ (wherein each $C_{1-6}$ alkyl is the same or different);
$R^2$ is —$CH_3$, —$CH_2CH_3$, —$CH(CH_3)_2$, —$CH_2CH_2CH_3$ or —$CH(CH_3)(OH)$;
$R^3$ is —H, —$C_{1-6}$alkyl, —$OC_{1-6}$alkyl, —$SC_{1-6}$alkyl, —$CH_2OH$, —$CH_2OCH_3$,

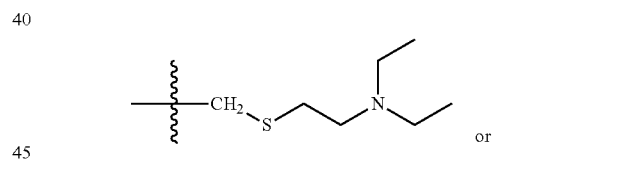

$R^4$ is —$CH_3$ or —$CH_2CH_3$;
$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
$R^6$ is —$CH_3$ or —$CH_2OH$;
n is 1, 2 or 3; and
q is 0, 1, 2, 3 or 4;
or a pharmaceutically acceptable salt thereof.

In embodiment (6), there is provided a compound of embodiment (1), wherein m is 3 or 4, and L is absent.

In embodiment (7), there is provided a compound of embodiment (1) or (6) having the following structure:

Formula XII

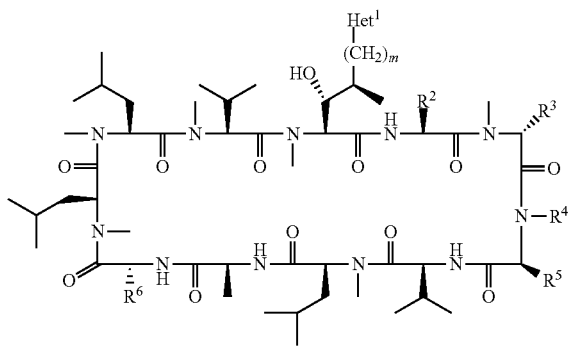

wherein:
Het$^1$ is a heterocyclyl optionally substituted with one or more R$^a$;
wherein each R$^a$ is independently selected from the group consisting of halogen, —C$_{1-6}$ alkyl, —OC$_{1-6}$ alkyl and —(CH$_2$)$_n$R$^b$;
wherein each R$^b$ is independently selected from Het$^2$, —C$_{1-6}$ haloalkyl, —OH, —NH$_2$, —NH(C$_{1-6}$ alkyl), —N(C$_{1-6}$ alkyl)$_2$ wherein each C$_{1-6}$ alkyl is the same or different, and
wherein Het$^2$ is a heterocyclyl optionally substituted with one or more halogen, —C$_{1-6}$ alkyl, —C$_{1-6}$ haloalkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$N(C$_{1-6}$ alkyl)$_2$ (wherein each C$_{1-6}$ alkyl is the same or different);
R$^2$ is —CH$_3$, —CH$_2$CH$_3$, —CH(CH$_3$)$_2$, —CH$_2$CH$_2$CH$_3$ or —CH(CH$_3$)(OH);
R$^3$ is —H, —C$_{1-6}$alkyl, —OC$_{1-6}$alkyl, —SC$_{1-6}$alkyl, —CH$_2$OH, —CH$_2$OCH$_3$,

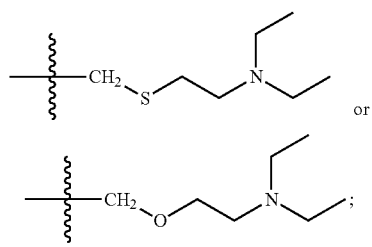

R$^4$ is —CH$_3$ or —CH$_2$CH$_3$;
R$^5$ is —CH(CH$_3$)$_2$, —CH$_2$CH(CH$_3$)$_2$, —CH$_2$C(CH$_3$)$_2$(OH), —CH(CH$_3$)(CH$_2$CH$_3$) or —CH$_2$CH(R$^c$)(CH$_2$CH$_3$), wherein R$^c$ is OC$_{1-6}$ alkyl;
R$^6$ is —CH$_3$ or —CH$_2$OH;
m is 1, 2, 3 or 4 (preferably, 3 or 4); and
n is 1, 2 or 3;
or a pharmaceutically acceptable salt thereof.

In embodiment (8), there is provided a compound of embodiment (1), wherein m is 2, and L is —O—(CH$_2$)$_p$—.

In embodiment (9), there is provided a compound of embodiment (1) or (8) having the following structure:

Formula XV

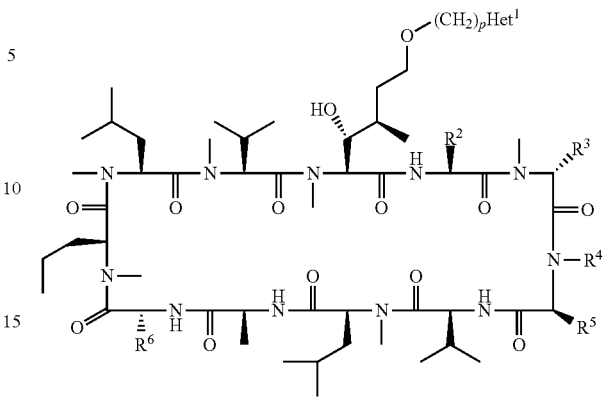

wherein:
Het$^1$ is a heterocyclyl optionally substituted with one or more R$^a$;
wherein each R$^a$ is independently selected from the group consisting of halogen, —C$_{1-6}$ alkyl, —OC$_{1-6}$ alkyl and —(CH$_2$)$_n$R$^b$;
wherein each R$^b$ is independently selected from Het$^2$, —C$_{1-6}$ haloalkyl, —OH, —NH$_2$, —NH(C$_{1-6}$ alkyl), —N(C$_{1-6}$alkyl)$_2$ wherein each C$_{1-6}$ alkyl is the same or different, and
wherein Het$^2$ is a heterocyclyl optionally substituted with one or more halogen, —C$_{1-6}$ alkyl, —C$_{1-6}$ haloalkyl, —(CH$_2$)$_{1-6}$OH, —(CH$_2$)$_{1-6}$NH$_2$, —(CH$_2$)$_{1-6}$NH(C$_{1-6}$ alkyl) or —(CH$_2$)$_{1-6}$N(C$_{1-6}$ alkyl)$_2$ (wherein each C$_{1-6}$ alkyl is the same or different);
R$^2$ is —CH$_3$, —CH$_2$CH$_3$, —CH(CH$_3$)$_2$, —CH$_2$CH$_2$CH$_3$ or —CH(CH$_3$)(OH);
R$^3$ is —H, —C$_{1-6}$alkyl, —OC$_{1-6}$alkyl, —SC$_{1-6}$alkyl, —CH$_2$OH, —CH$_2$OCH$_3$,

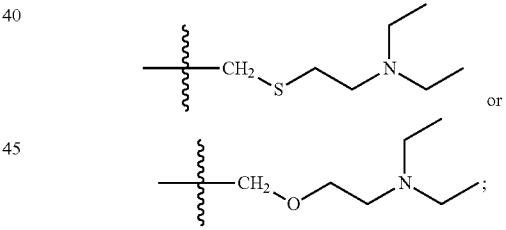

R$^4$ is —CH$_3$ or —CH$_2$CH$_3$;
R$^5$ is —CH(CH$_3$)$_2$, —CH$_2$CH(CH$_3$)$_2$, —CH$_2$C(CH$_3$)$_2$(OH), —CH(CH$_3$)(CH$_2$CH$_3$) or —CH$_2$CH(R$^c$)(CH$_2$CH$_3$), wherein R$^c$ is OC$_{1-6}$ alkyl;
R$^6$ is —CH$_3$ or —CH$_2$OH;
n is 1, 2 or 3; and
p is 0 or 1;
or a pharmaceutically acceptable salt thereof.

In embodiment (10), there is provided a compound of any one of embodiments (1), (2) and (6) through (9), wherein Het$^1$ is a mono or bicyclic heterocyclyl containing from 3 to 10 ring atoms, wherein at least one ring atom is nitrogen, and wherein Het$^1$ is optionally substituted with one or more R$^a$.

In embodiment (11), there is provided a compound of embodiment (1) or (10), wherein Het$^1$ contains at least one aromatic heterocycle.

In embodiment (12), there is provided a compound of embodiment (1) or (10), wherein Het$^1$ is a monocyclic heterocyclyl containing from 5 to 6 ring atoms and is optionally substituted with one or more $R^a$.

In embodiment (13), there is provided a compound of embodiment (12), wherein $Het^1$ is an aromatic heterocyclyl containing from 5 to 6 ring atoms and is optionally substituted with one or more $R^a$.

In embodiment (14), there is provided a compound of any one of embodiments (1), (2), and (6) through (10), wherein $Het^1$ is selected from imidazolyl, oxazolinyl, thiazolyl, pyrazolyl, pyridinyl, pyrazinyl, pyridazinyl, pyrimidinyl, benzimidazolyl, imidazo[1,2-a]pyridin-2-yl, tetrahydro-imidazo[1,2-a]pyridin-2-yl, 3a,4,5,6,7,7a-hexahydro-1H-benzo[d]imidazole and 4,5,6,7-tetrahydro-1H-benzo[d]imidazole; wherein each of the foregoing is optionally substituted with one or more $R^a$.

In embodiment (15), there is provided a compound of any one of the preceding embodiments, wherein $Het^1$ is optionally substituted with one $R^a$.

In embodiment (16), there is provided a compound of any one of the preceding embodiments, wherein $Het^1$ is substituted with one $R^a$, which is —$(CH_2)_nR^b$.

In embodiment (17), there is provided a compound of any one of the preceding embodiments, wherein $R^b$ is $Het^2$.

In embodiment (18), there is provided a compound of any one of the preceding embodiments, wherein $Het^2$ is an unsubstituted heterocycle.

In embodiment (19), there is provided a compound of any one of the preceding embodiments, wherein $Het^2$ is selected from morpholinyl, pyridinyl and pyrrolidinyl.

In embodiment (20), there is provided a compound of any one of the preceding embodiments, wherein $Het^2$ is selected from N-morpholinyl, pyridin-2-yl, pyridin-3-yl and N-pyrrolidinyl.

In embodiment (21), there is provided a compound of any one of the preceding embodiments, wherein $R^3$ is —H, —$OC_{1-3}$alkyl or —$SC_{1-3}$alkyl.

In embodiment (22), there is provided a compound of any one of the preceding embodiments, wherein $R^3$ is —H, —$CH_3$, —$OCH_3$ or —$SCH_3$.

In embodiment (23), there is provided a compound of any one of the preceding embodiments, wherein $R^3$ is —H or —$CH_3$.

In embodiment (24), there is provided a compound of embodiment (1), wherein $Het^1$ is heterocyclyl, which is unsubstituted or substituted with one or more $R^a$,
  wherein each $R^a$ is independently selected from the group consisting of halogen, —$C_{1-6}$alkyl, —$OC_{1-6}$alkyl and —$(CH_2)_nR^b$;
    wherein each $R^b$ is independently selected from —OH, —$N(C_{1-6}alkyl)_2$, —$C_{1-6}$haloalkyl and $Het^2$;
      wherein $Het^2$ is unsubstituted heterocyclyl.

In embodiment (25), there is provided the compound of any one of the preceding embodiments, wherein each $R^a$ is independently selected from the group consisting of F, Cl, Br, methyl, ethyl, n-propyl, isopropyl, —$OCH_3$, and —$(CH_2)_nR^b$; wherein each $R^b$ is independently selected from —OH, —$N(CH_3)_2$, —$CF_3$ and $Het^2$; wherein $Het^2$ is unsubstituted heterocyclyl.

In embodiment (26), there is provided the compound of any one of the preceding embodiments, wherein $R^2$ is ethyl; $R^3$ is H, methyl, —$CH_2OCH_3$, —$CH_2OH$ or —$SCH_3$; $R^4$ is methyl; $R^5$ is —$CH_2CH(CH_3)_2$; and $R^6$ is methyl.

In embodiment (27), there is provided a compound selected from the group consisting of:
[(2S,3R,4R)-3-Hydroxy-4-methyl-2-(methylamino)-5-(1-Methyl-1H-imidazol-2-yl)-pentanoic acid]$^1$ [(R)-methyl-Sar]$^3$ cyclosporin A;
[(2S,3R,4R)-3-Hydroxy-4-methyl-2-(methylamino)-5-(1-(N-morpholino-ethyl)-1H-imidazol-2-yl)-pentanoic acid]$^1$ [(R)-methyl-Sar]$^3$ cyclosporin A;
[(2S,3R,4R)-3-Hydroxy-4-methyl-2-(methylamino)-5-(1-(N-pyrrolidinyl-ethyl)-1H-imidazol-2-yl)pentanoic acid]$^1$ [(R)-methyl-Sar]$^3$ cyclosporin A;
[(2S,3R,4R)-5-(1-(N,N-Dimethyl-ethyl)-1H-imidazol-2-yl)-3-hydroxy-4-methyl-2-(methylamino) pentanoic acid]$^1$ [(R)-methyl-Sar]$^3$ cyclosporin A;
[(2S,3R,4R)-3-Hydroxy-4-methyl-2-(methylamino)-5-(1-(pyridin-2-yl-methyl)-1H-imidazol-2-yl-pentanoic acid]$^1$ [(R)-methyl-Sar]$^3$cyclosporin A;
[(2S,3R,4R)-3-Hydroxy-5-(1-(3-hydroxypropyl)-1H-imidazol-2-yl)-4-methyl-2-(methylamino) pentanoic acid]$^1$ [(R)-methyl-Sar]$^3$ cyclosporin A;
[(2S,3R,4R)-3-Hydroxy-4-methyl-2-(methylamino)-5-(1-(pyridin-3-yl-ethyl)-1H-imidazol-2-yl) pentanoic acid]$^1$ [(R)-methyl-Sar]$^3$ cyclosporin A;
[(2S,3R,4R)-3-Hydroxy-4-methyl-2-(methylamino)-5-[3-(3,3,3-trifluoro-propyl)-3H-imidazol-4-yl]-pentanoic acid]$^1$ [(R)-methyl-Sar]$^3$ cyclosporin A;
[(2S,3R,4R)-1-(1H-Benzimidazol-2-yl)-3-hydroxy-4-methyl-2-(methylamino) pentanoic acid]$^1$ [(R)-methyl-Sar]$^3$ cyclosporin A;
[(2S,3R,4R)-1-(1H-Benzimidazol-2-yl)-3-hydroxy-4-methyl-2-(methylamino) pentanoic acid]$^1$ cyclosporin A;
[(2S,3R,4S)-3-Hydroxy-4-methyl-2-(methylamino)-7-(pyridin-3-yl)-heptanoic acid]$^1$ [(R)-methyl-Sar]$^3$ cyclosporin A;
[(2S,3R,4R)-3-Hydroxy-4-methyl-2-(methylamino)-7-(pyridin-2-yl)-heptanoic acid]$^1$ [(R)-methyl-Sar]$^3$ cyclosporin A;
[(2S,3R,4R)-3-Hydroxy-4-methyl-2-(methylamino)-7-(2-methyl-thiazol-4-yl)-heptanoic acid]$^1$ [(R)-methyl-Sar]$^3$ cyclosporin A;
[(2S,3R,4R)-7-(5-Fluoro-pyridin-2-yl)-3-hydroxy-4-methyl-2-(methylamino)-heptanoic acid]$^1$ [(R)-methyl-Sar]$^3$ cyclosporin A;
[(2S,3R,4R)-3-Hydroxy-4-methyl-2-(methylamino)-7-(pyridin-4-yl)-heptanoic acid]$^1$ [(R)-methyl-Sar]$^3$ cyclosporin A;
[(2S,3R,4R)-3-Hydroxy-4-methyl-2-(methylamino)-7-(5-methoxy-pyridin-2-yl)-heptanoic acid]$^1$ [(R)-methyl-Sar]$^3$ cyclosporin A;
[(2S,3R,4R)-3-Hydroxy-4-methyl-2-(methylamino)-7-(2-methyl-pyridin-4-yl)-heptanoic acid]$^1$ [(R)-methyl-Sar]$^3$ cyclosporin A;

[(2S,3R,4R)-3-Hydroxy-4-methyl-2-(methylamino)-7-(pyrazin-2-yl)-heptanoic acid]¹ [(R)-methyl-Sar]³ cyclosporin A;

[(2S,3R,4R)-3-Hydroxy-4-methyl-2-(methylamino)-7-(5,6,7,8-tetrahydro imidazo[1,2-a]pyridin-2-yl)-heptanoic acid]¹ [(R)-methyl-Sar]³ cyclosporin A;

[(2S,3R,4R)-3-Hydroxy-7-(1-methyl-1H-imidazol-4-yl)-4-methyl-2-(methylamino) heptanoic acid]¹ [(R)-methyl-Sar]³ cyclosporin A;

[(2S,3R,4R)-3-Hydroxy-4-methyl-2-(methylamino)-7-(pyridazin-3-yl)-heptanoic acid]¹ [(R)-methyl-Sar]³ cyclosporin A;

[(2S,3R,4R)-3-Hydroxy-4-methyl-2-(methylamino)-7-(pyrimidin-2-yl)-heptanoic acid]¹ [(R)-methyl-Sar]³ cyclosporin A;

[(2S,3R,4R)-3-Hydroxy-4-methyl-2-(methylamino)-7-(2-methylpyrazol-3-yl)-heptanoic acid]¹ [(R)-methyl-Sar]³ cyclosporin A;

[(2S,3R,4R)-3-Hydroxy-4-methyl-2-(methylamino)-7-(oxazolin-2-yl)-heptanoic acid]¹ cyclosporin A;

[(2S,3R,4R)-3-Hydroxy-4-methyl-2-(methylamino)-7-(1-methylpyrazol-3-yl) heptanoic acid]¹ [(R)-methyl-Sar]³ cyclosporin A;

[(2S,3R,4R)-3-Hydroxy-7-(1-methyl-1H-imidazol-2-yl)-4-methyl-2-(methylamino) heptanoic acid]¹ [(R)-methyl-Sar]³ cyclosporin A;

[(2S,3R,4R)-3-Hydroxy-4-methyl-2-(methylamino)-7-(1-methylpyrazol-4-yl)-heptanoic acid]¹ [(R)-methyl-Sar]³ cyclosporin A;

[(2S,3R,4R)-3-Hydroxy-4-methyl-2-(methylamino)-8-(pyridin-2-yl)-octanoic acid]¹ [(R)-methyl-Sar]³ cyclosporin A;

[(2S,3R,4R)-3-Hydroxy-4-methyl-2-(methylamino)-7-(pyridin-2-yl)-heptanoic acid]¹ cyclosporin A;

[(2S,3R,4R)-3-Hydroxy-4-methyl-2-(methylamino)-7-(pyridin-4-yl)-heptanoic acid]¹ cyclosporin A;

[(2S,3R,4R)-3-Hydroxy-4-methyl-2-(methylamino)-7-(pyridin-3-yl)-heptanoic acid]¹ cyclosporin A;

[(2S,3R,4R)-3-Hydroxy-4-methyl-2-(methylamino)-7-(pyrimidin-2-yl)-heptanoic acid]¹ cyclosporin A;

[2S,3R,4R)-3-Hydroxy-4-methyl-2-(methylamino)-7-(pyrid-4-yl)heptanoic acid]¹ [(R)-methoxymethyl Sar]³ cyclosporin A;

[2S,3R,4R)-3-Hydroxy-4-methyl-2-(methylamino)-7-(pyrid-2-yl)heptanoic acid]¹ [(R)-hydroxymethyl Sar]³ cyclosporin A;

[2S,3R,4R)-3-Hydroxy-4-methyl-2-(methylamino)-7-(pyrid-2-yl)heptanoic acid]¹ [(R)-thiomethyl Sar]³ cyclosporin A;

[(2S,3R,4R)-3-Hydroxy-4-methyl-2-(methylamino)-6-(pyrimidin-2-yloxy)-hexanoic acid]¹ cyclosporin A;

[(2S,3R,4R)-3-Hydroxy-4-methyl-2-(methylamino)-6-(pyridin-4-ylmethoxy)-hexanoic acid]¹ cyclosporin A;

[(2S,3R,4R)-3-Hydroxy-4-methyl-2-(methylamino)-6-(pyridin-4-yl)-hexanoic acid]¹ [(R)-methyl-Sar]³ cyclosporin A;

[(2S,3R,4R)-3-Hydroxy-4-methyl-2-(methylamino)-6-(pyridin-4-yl)-hexanoic acid]¹ cyclosporin A;

[(2S,3R,4R)-3-Hydroxy-4-methyl-2-(methylamino)-6-(pyridin-2-yl)-hexanoic acid]¹ [(R)-methyl-Sar]³ cyclosporin A; and

[(2S,3R,4R)-3-Hydroxy-4-methyl-2-(methylamino)-6-(pyridin-2-yl)-hexanoic acid]¹ cyclosporin A.

In embodiment (28), there is provided a compound selected from the group consisting of:

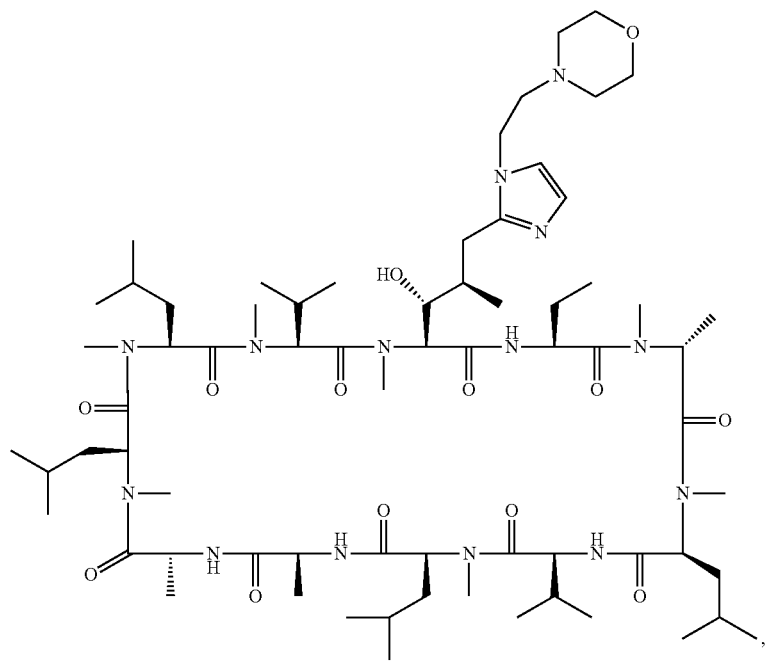
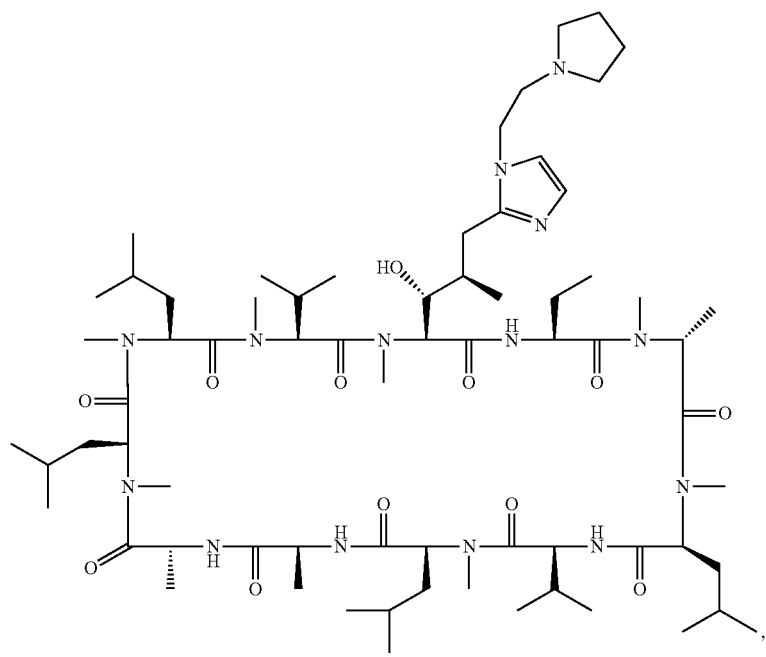

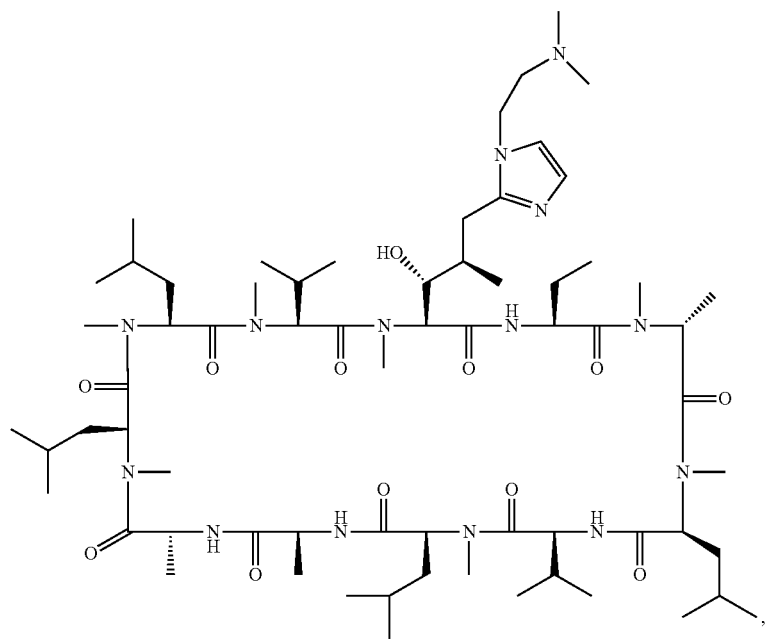
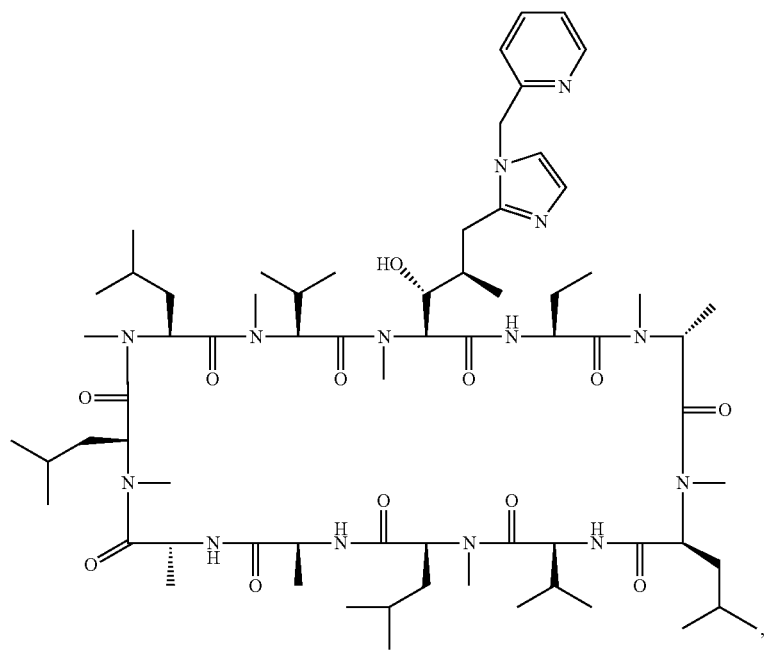

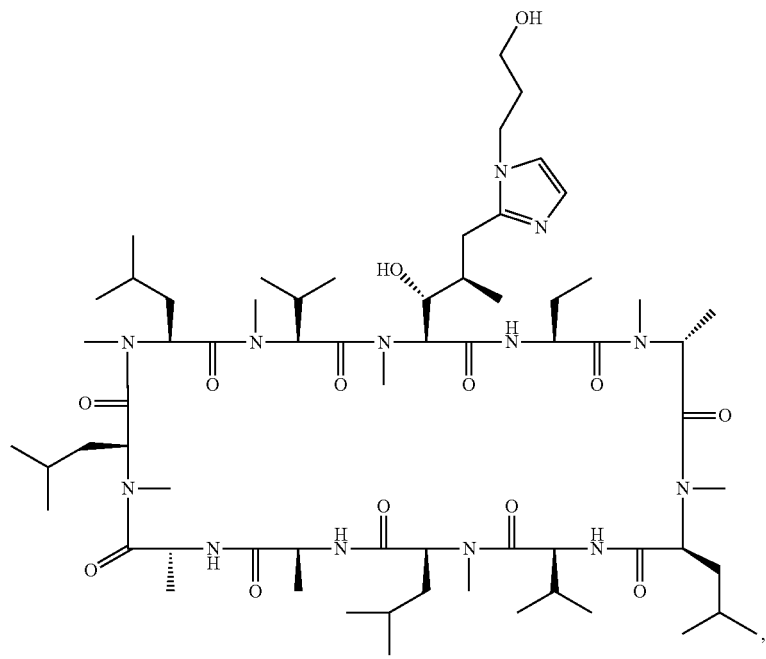
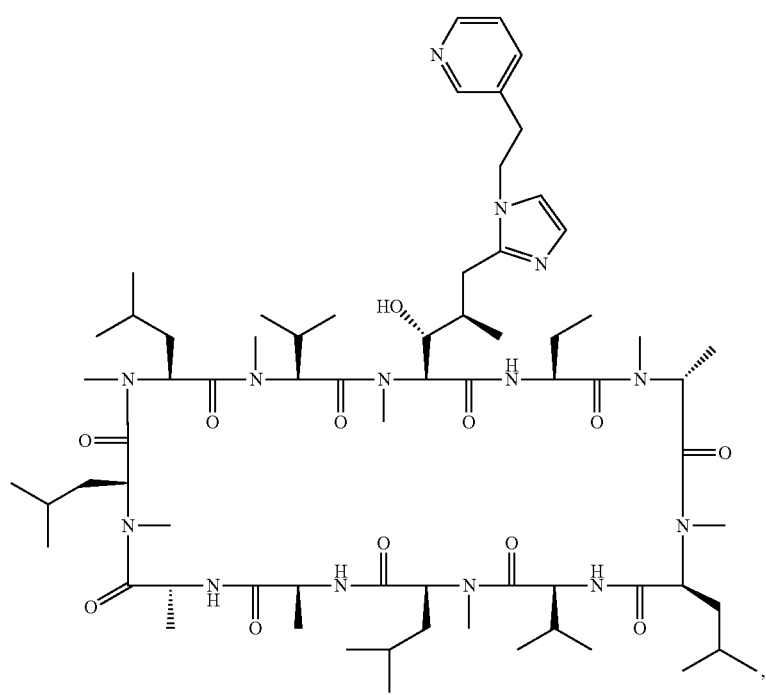

-continued
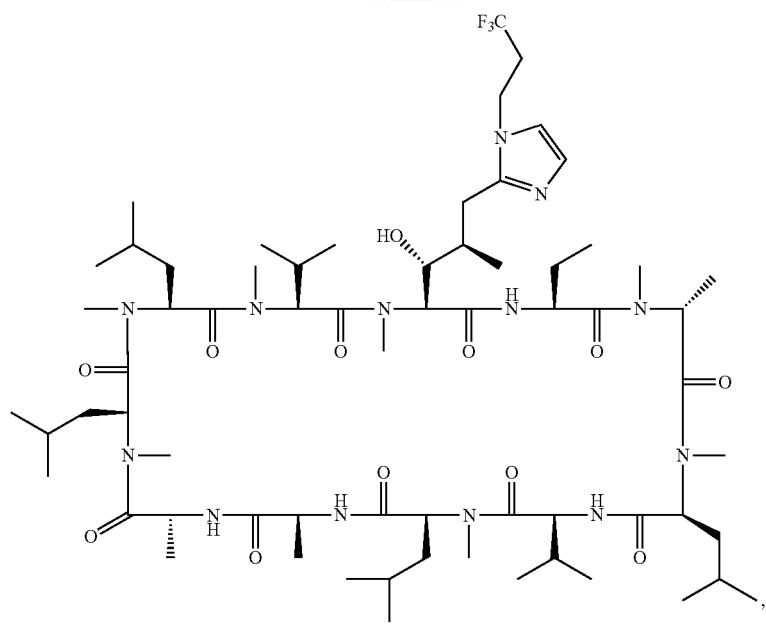
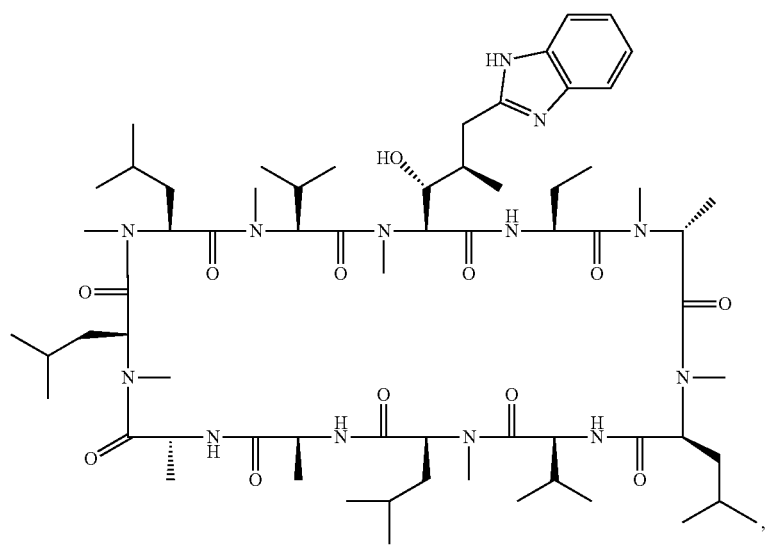
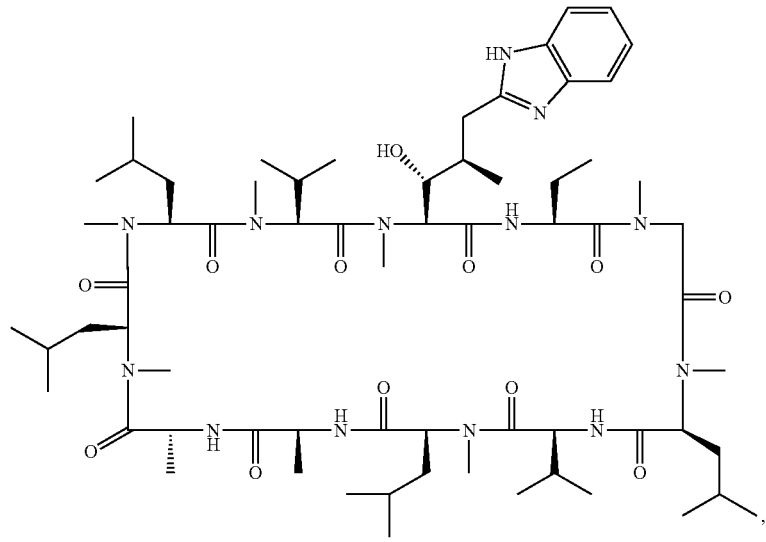

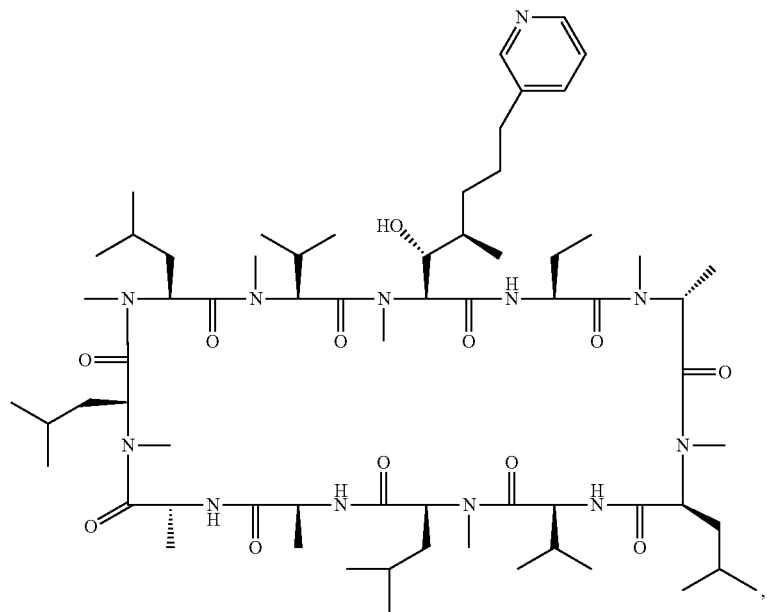
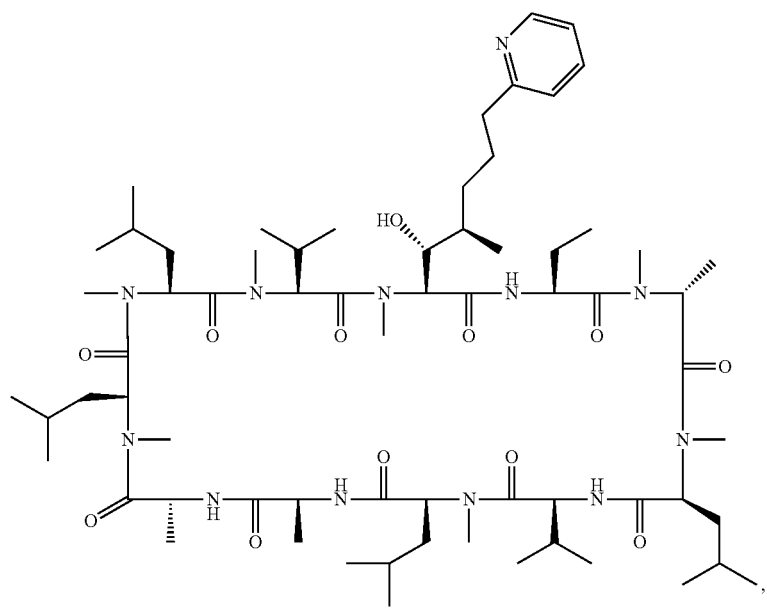

-continued
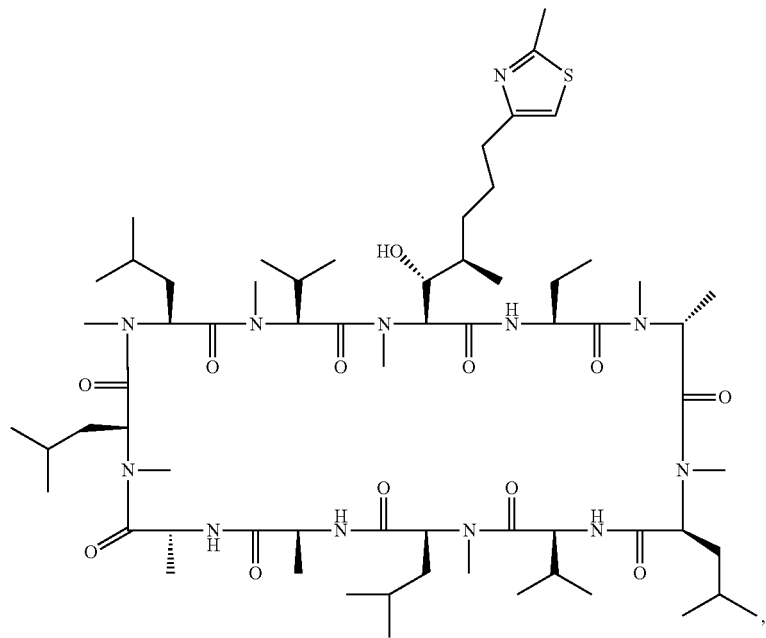
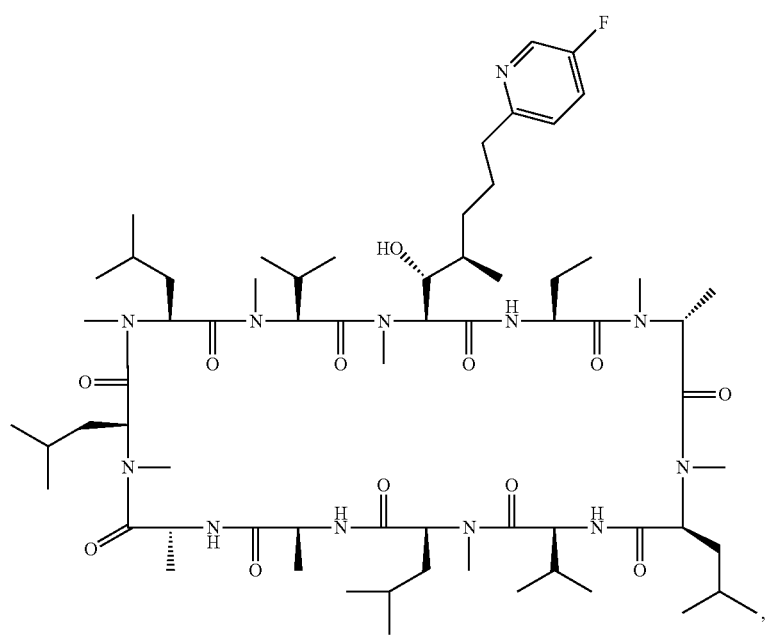

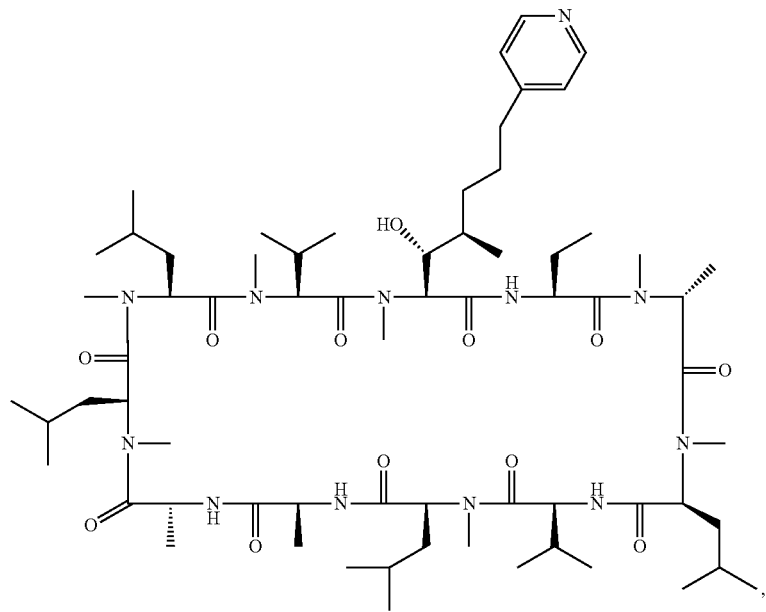
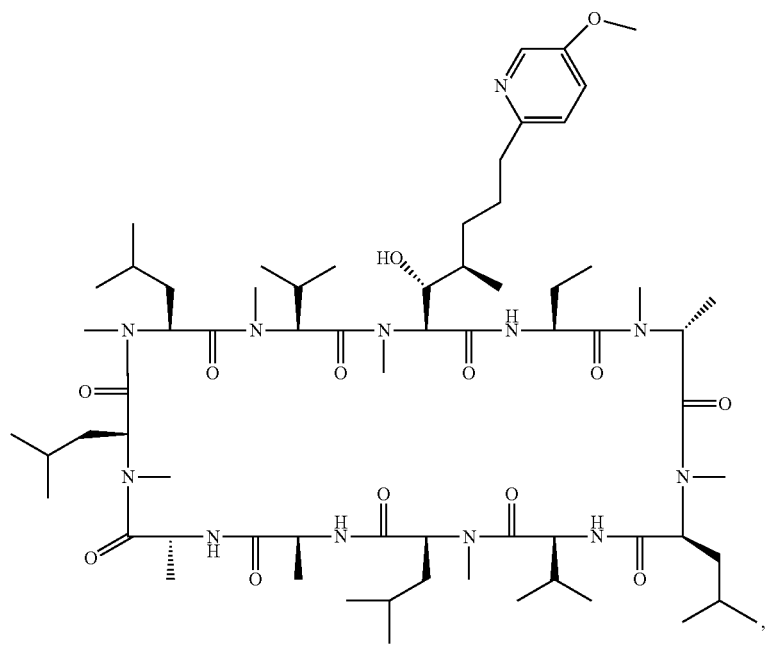

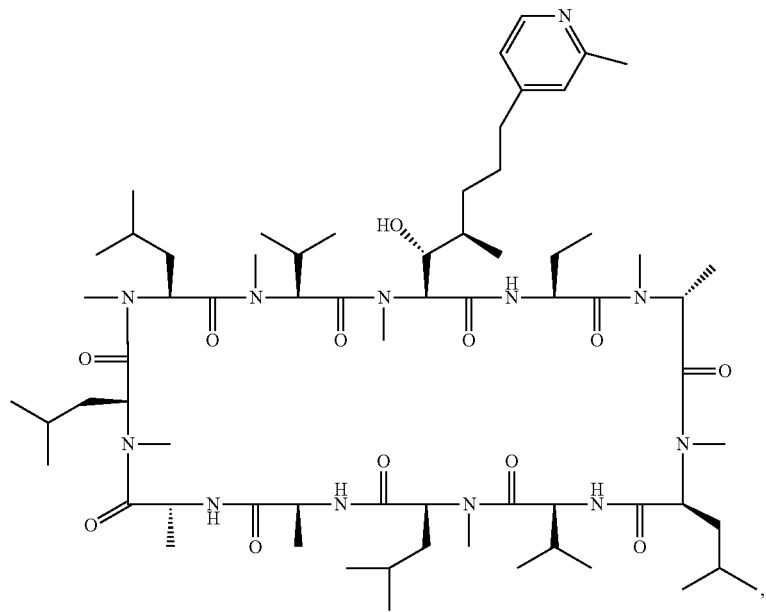
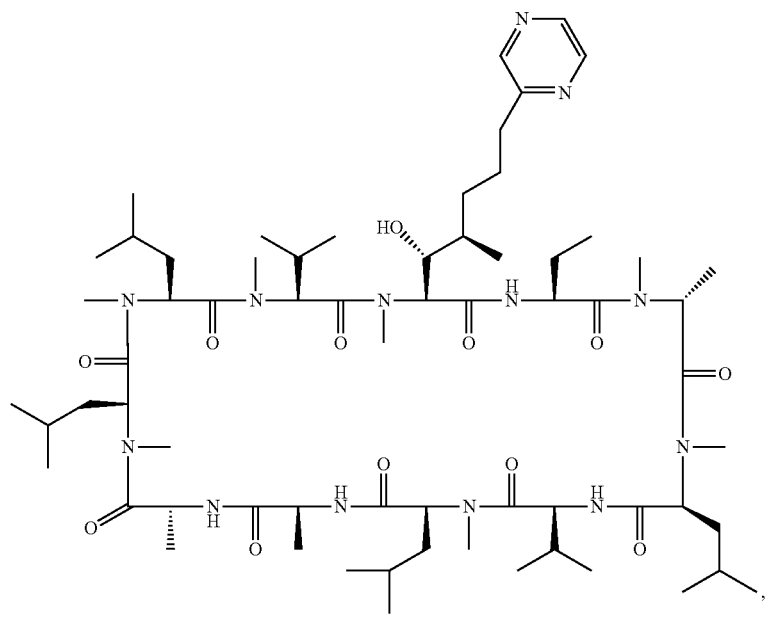

-continued
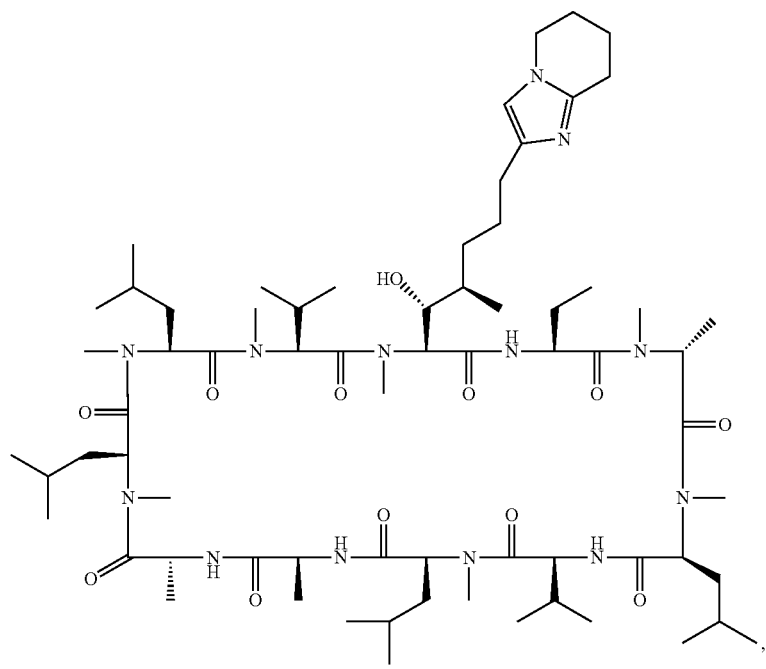
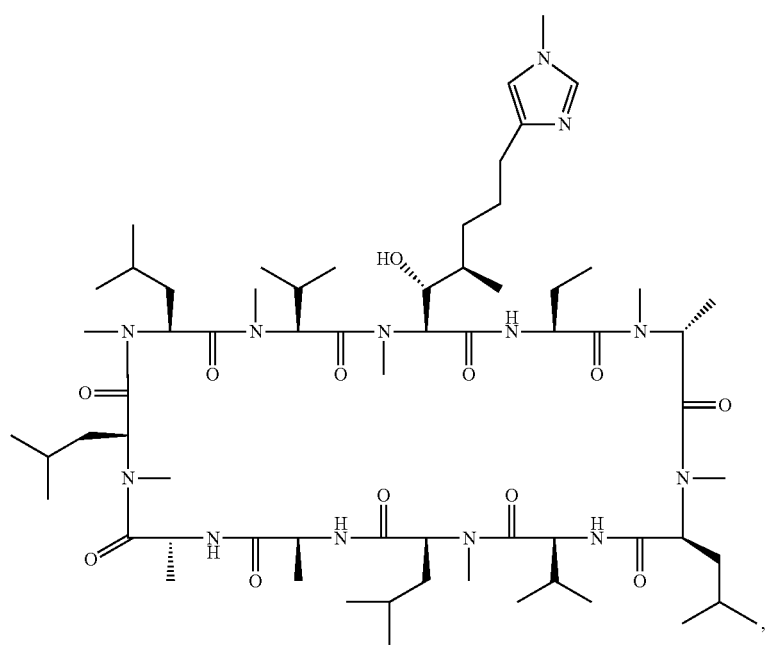

-continued
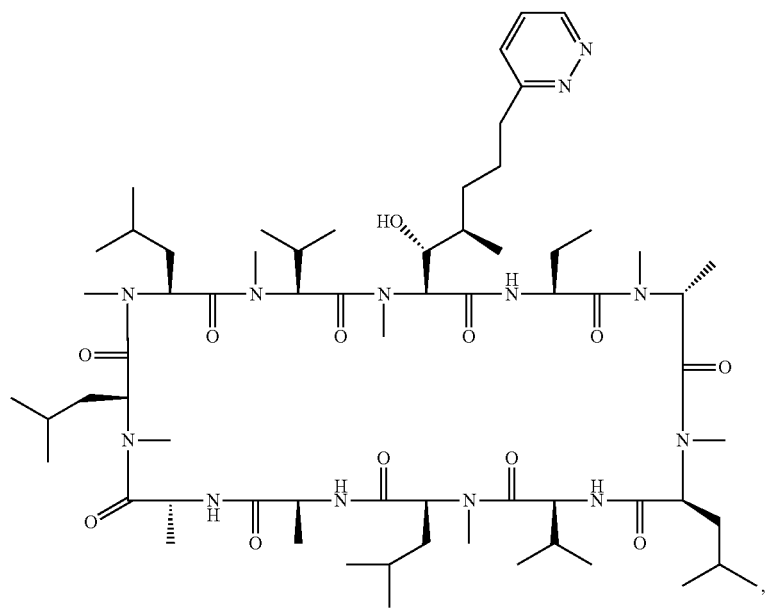
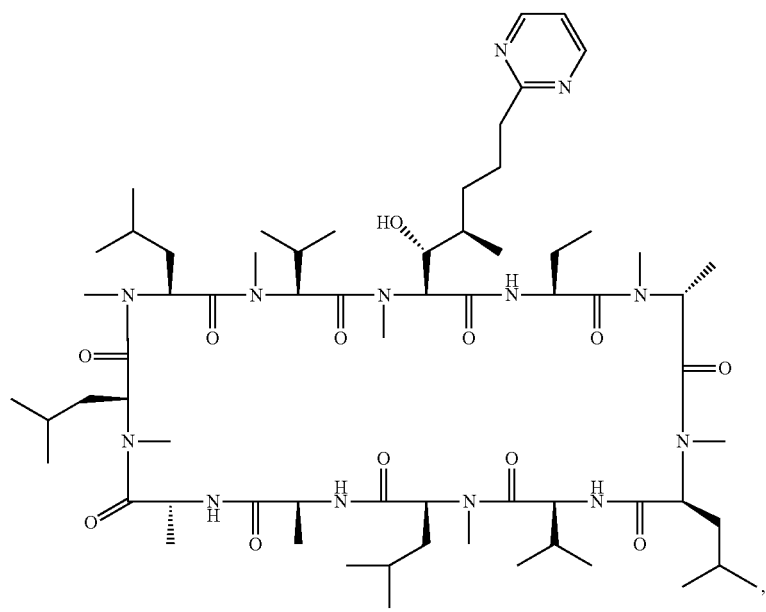

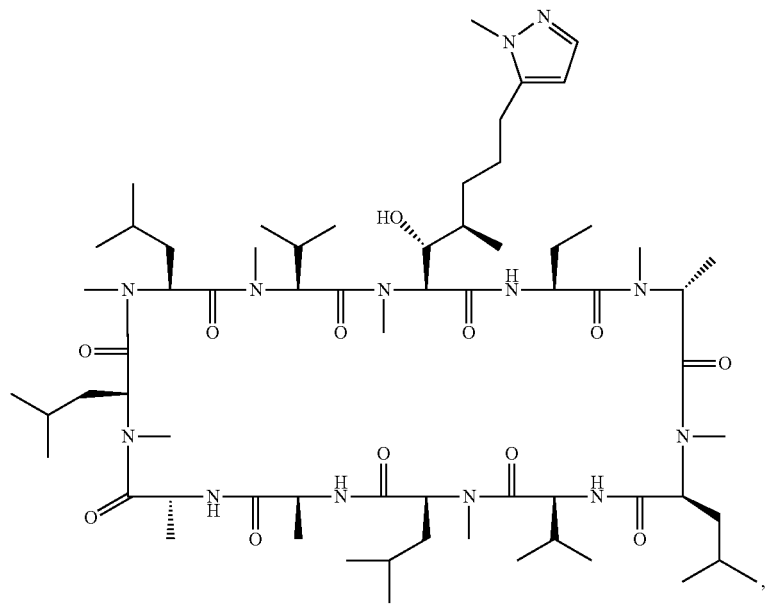
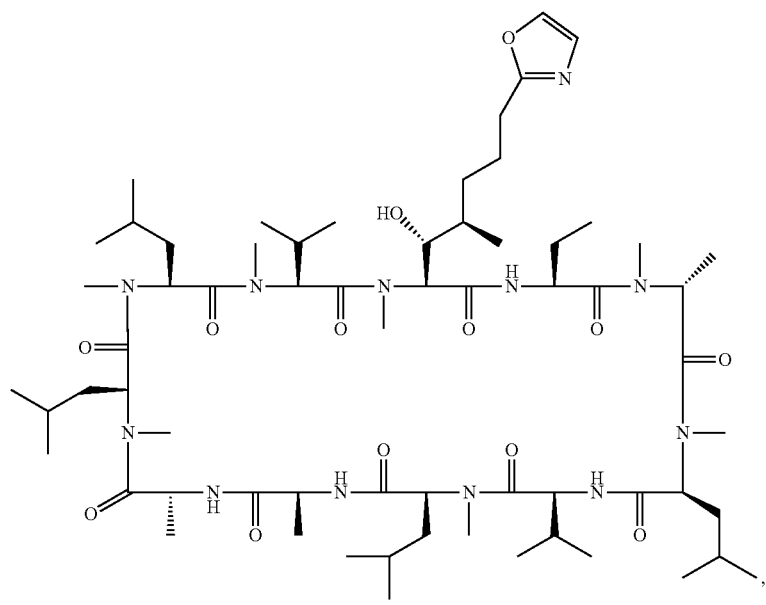

-continued
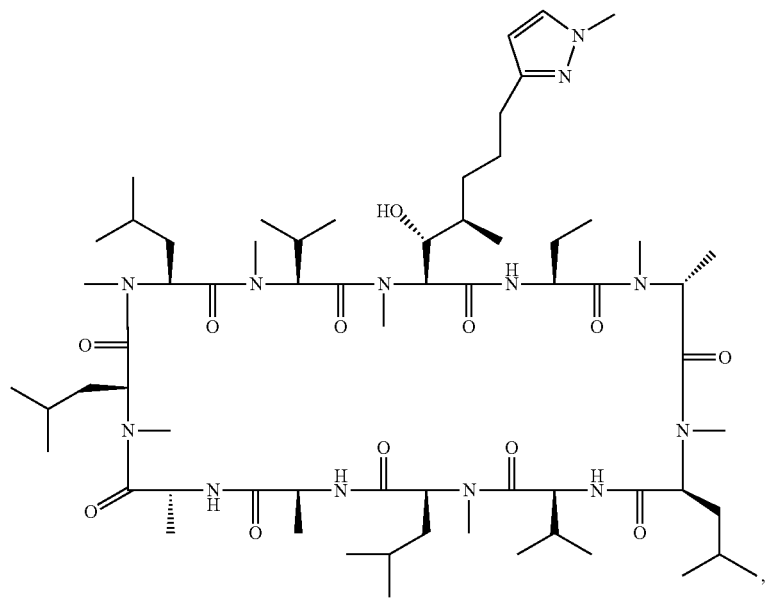
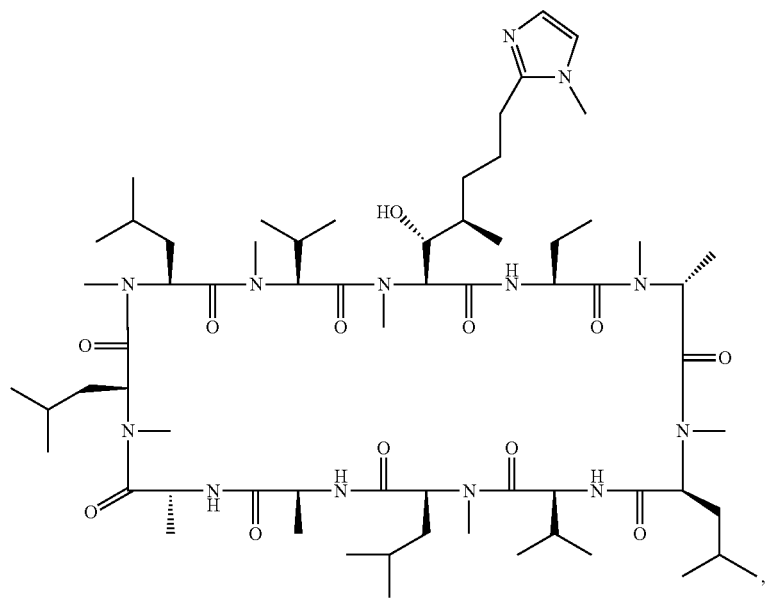

-continued
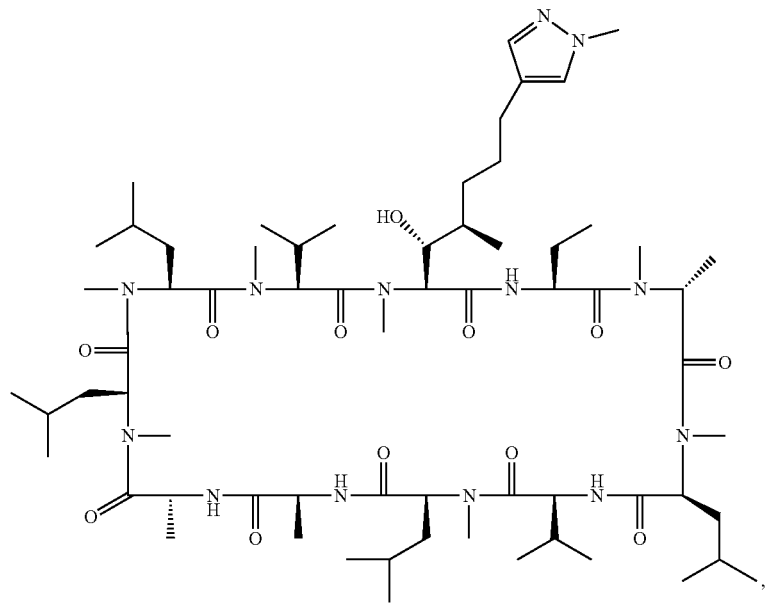
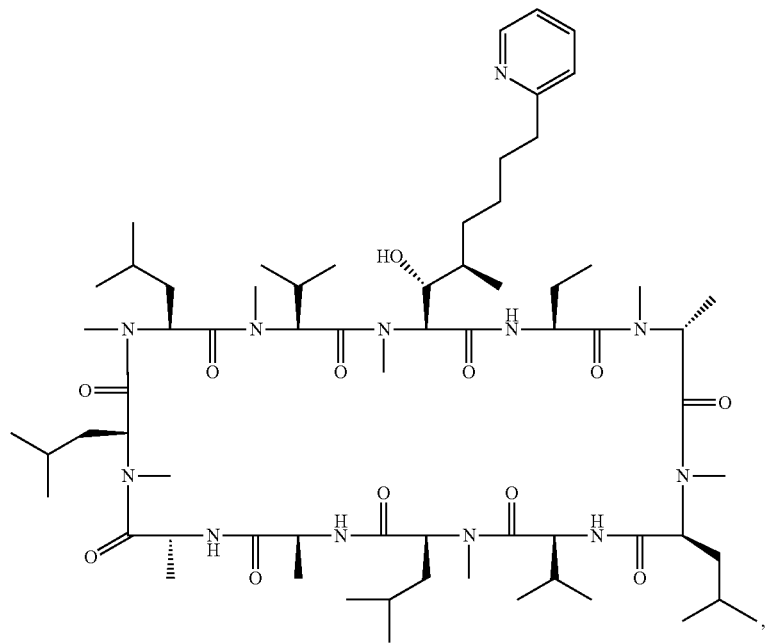

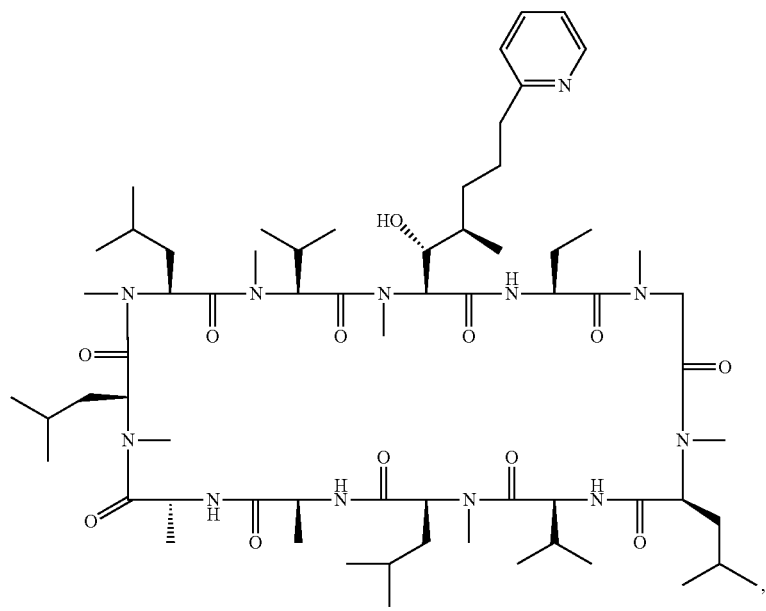
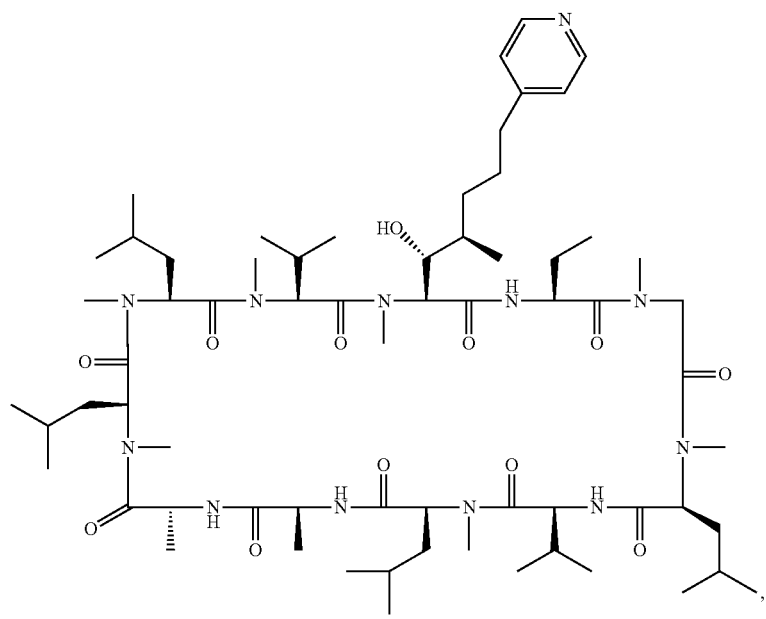

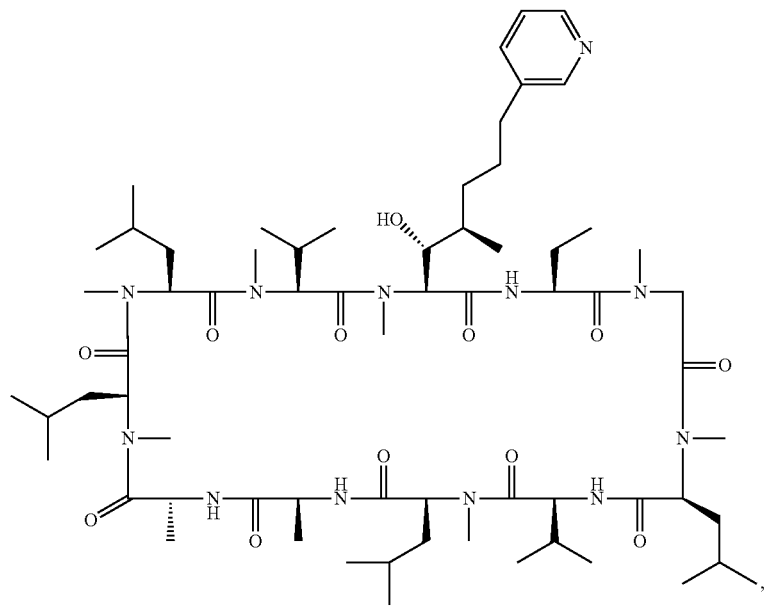
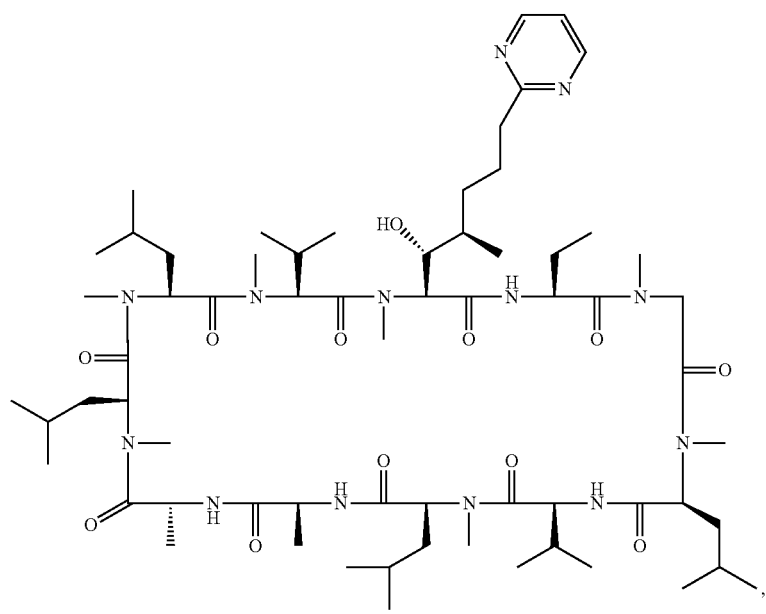

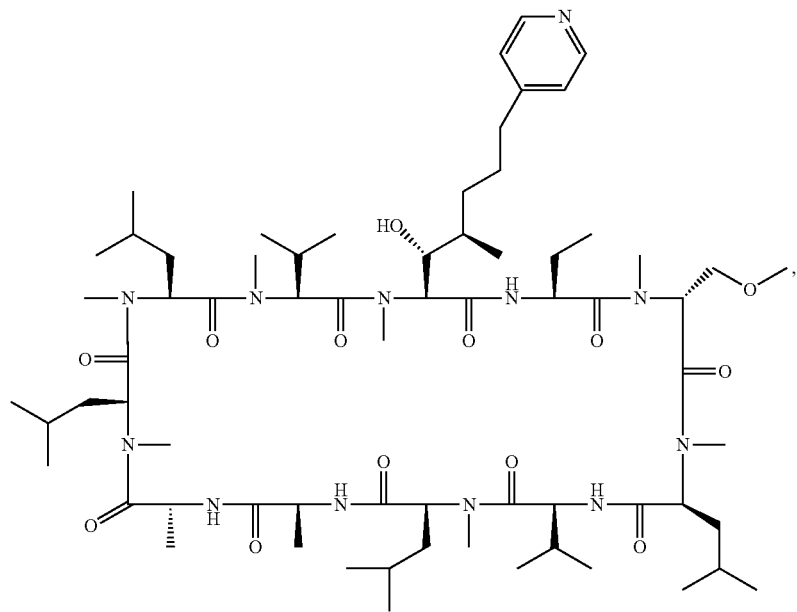
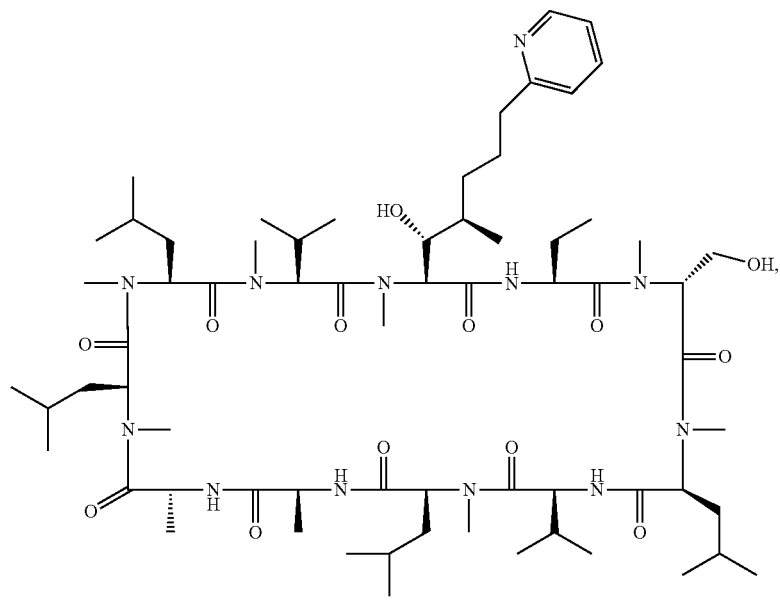

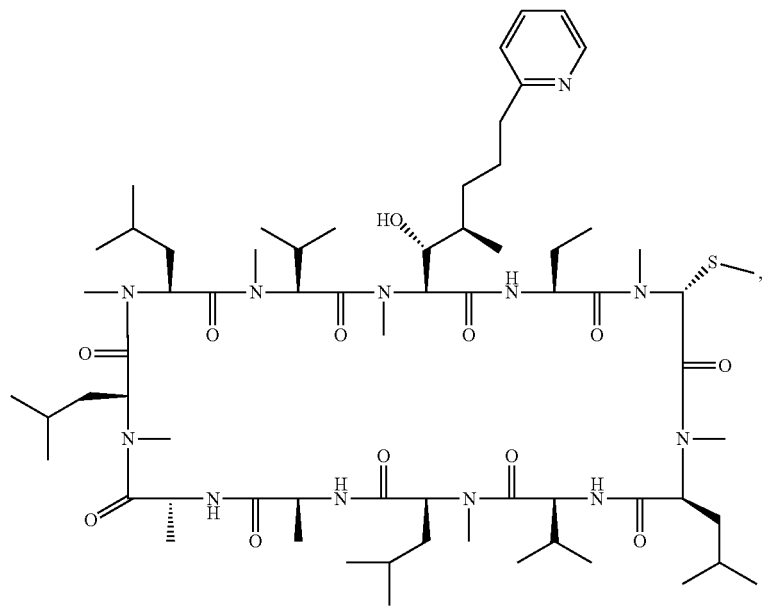
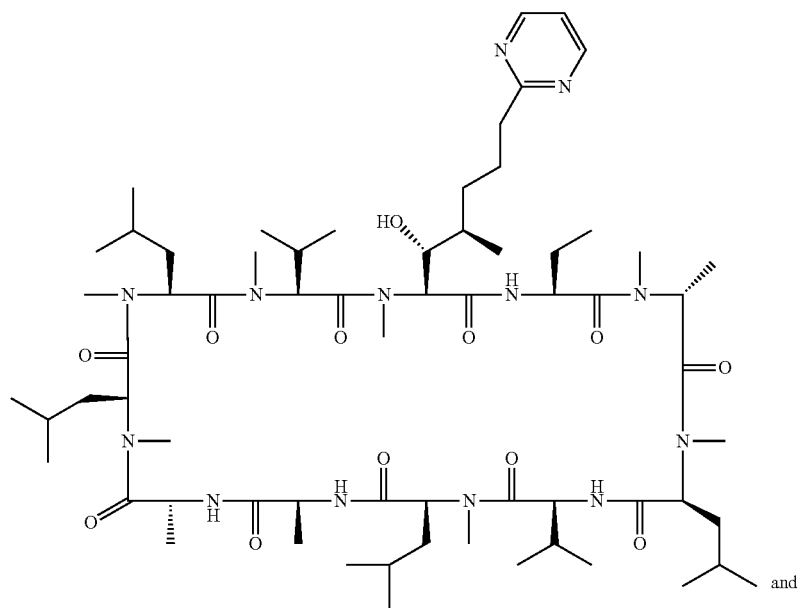
and

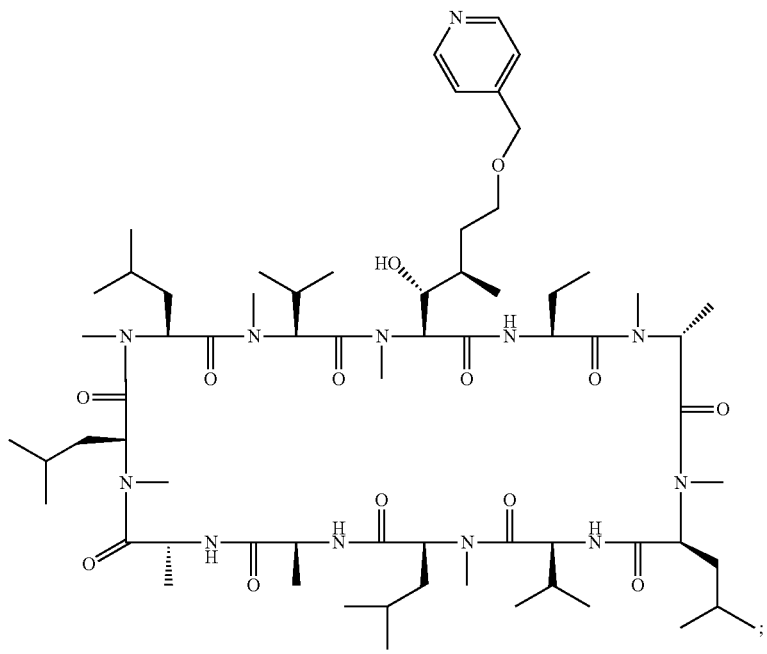

and pharmaceutically acceptable salts thereof.

In embodiment (29), there is provided a pharmaceutical composition comprising a compound of any one of embodiments (1) through (28) and a pharmaceutically acceptable excipient.

In embodiment (30), there is provided the pharmaceutical composition of embodiment (29), wherein the pharmaceutically acceptable excipient is an ophthalmically acceptable excipient.

In embodiment (31), there is provided a pharmaceutical composition comprising a therapeutically effective amount of a compound of any one of embodiments (1) through (28), or a pharmaceutically acceptable salt thereof, and a pharmaceutically acceptable excipient.

In embodiment (32), there is provided a method of treating a medical condition in a subject in need thereof, the method comprising administering to the subject (a) a therapeutically effective amount of a compound of any one of embodiments (1) through (28) or a pharmaceutically acceptable salt thereof, or (b) a pharmaceutical composition of any one of embodiments (29) through (31), thereby treating the condition.

In embodiment (33), there is provided the method of embodiment (32), wherein the medical condition is dry eye, dry eye disease, ocular surface inflammation, corneal transplant rejection, ocular inflammation caused by an ocular surgery, suppressed tear production, blepharitis, meibomian gland disease, allergic conjunctivitis, pterygium, ocular symptoms of graft-versus-host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, adenoviral keratoconjunctivitis, ocular rosacea or pinguecula.

In embodiment (34), there is provided the method of embodiment (32) or (33), wherein the condition is corneal transplant rejection, and the treatment results in the retention of the corneal implant.

In embodiment (35), there is provided the method of embodiment (32) or (33), wherein the condition is ocular inflammation caused by an ocular surgery, and the treatment reduces the inflammation.

In embodiment (36), there is provided the method of embodiment (32) or (33), wherein the condition is suppressed tear production, and the method results in the enhancement of tear production; in a further embodiment, the suppressed tear production is due to ocular inflammation associated with keratoconjunctivitis sicca (dry eye disease).

In embodiment (37), there is provided the method of embodiment (32), wherein the medical condition is a dermatological inflammation, and the method reduces the inflammation.

In embodiment (38), there is provided the method of embodiment (32) or (37), wherein the medical condition is psoriasis, and the method treats the psoriasis.

In embodiment (39), there is provided the method of embodiment (32), wherein the compound is administered to the subject topically, orally, systemically or via an implant, such as an ocular implant.

In embodiment (40), there is provided the method of any one of embodiments (32) through (39), wherein the subject is a human.

In embodiment (41), there is provided a method for making a compound of Formula IIIb:

Formula IIIb

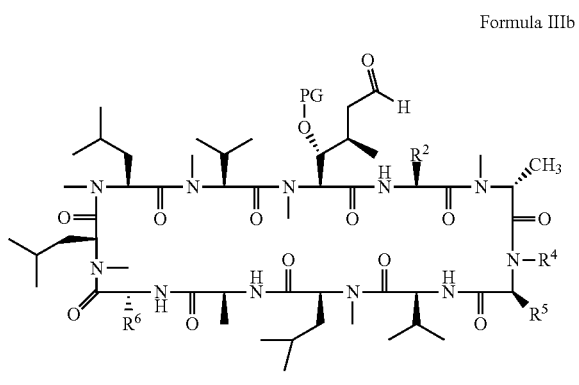

wherein R², R⁴, R⁵ and R⁶ are as defined in Formula I, and PG is a protecting group;

the method comprising:

(a) adding 10% palladium on carbon to a solution comprising a compound of Formula III' having the following structure Formula III' to provide a mixture;

(b) stirring the mixture from step (a) under a hydrogen atmosphere;

(c) filtering the mixture from step (b) through diatomaceous earth to provide a filtrate, and collecting the filtrate;

(d) washing the diatomaceous earth from step (c) with an organic solvent to obtain a wash solution, and combining the wash solution with the filtrate from step (c) to obtain a solution containing the compound of Formula IIIb;

(e) evaporating the solution containing the compound of Formula IIIb from step (d) to obtain the compound of Formula IIIb as a major product.

In embodiment (42), there is provided the method of embodiment (41) for making a compound of Formula IIIc:

Formula IIIc wherein R², R⁴, R⁵ and R⁶ are as defined in Formula I, the method comprising:

(a) adding 10% palladium on carbon to an ethanol solution comprising a compound of Formula III" having the following structure Formula III"

to provide a mixture;

(b) stirring the mixture from step (a) under a hydrogen atmosphere;

(c) filtering the mixture from step (b) through diatomaceous earth to provide a filtrate, and collecting the filtrate;

(d) washing the diatomaceous earth from step (c) with ethyl acetate to obtain a wash solution, and combining the wash solution with the filtrate from step (c) to obtain a solution containing the compound of Formula IIIc;

(e) evaporating the solution containing the compound of Formula IIIc from step (d) to obtain the compound of Formula IIIc as a major product.

In embodiment (43), there is provided the method of embodiment (41) or (42) for making a compound of Formula IIId:

Formula IIId

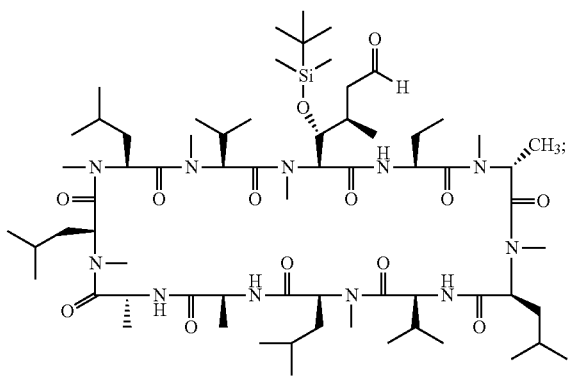

the method comprising:
(a) adding 10% palladium on carbon to an ethanol solution comprising a compound of Formula III''' to provide a mixture Formula III'''

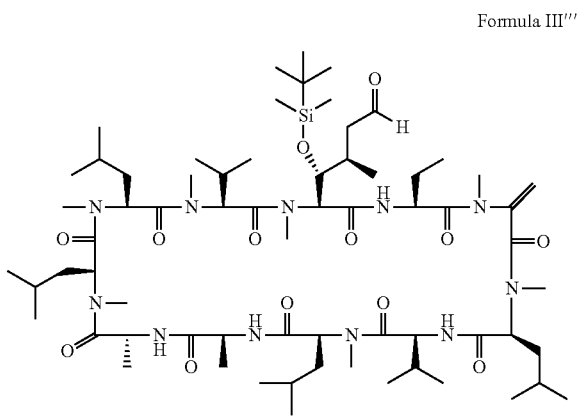 [SMILES: C=C1C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@H](O[Si](C)(C)C(C)(C)C)[C@H](C)CC=O)C(=O)N[C@H](CC)C(=O)N1C]

to provide a mixture;
(b) stirring the mixture from step (a) under a hydrogen atmosphere;
(c) filtering the mixture from step (b) through diatomaceous earth to provide a filtrate, and collecting the filtrate;
(d) washing the diatomaceous earth from step (c) with ethyl acetate to obtain a wash solution, and combining the wash solution with the filtrate from step (c) to obtain a solution containing the compound of Formula IIId;
(e) evaporating the solution containing the compound of Formula IIId from step (d) to obtain the compound of Formula IIId as a major product.

In embodiment (44), there is provided the method of embodiment (41), wherein the protecting group is —C(O)CH$_3$ or —Si(Me)$_2$(t-Bu).

In embodiment (45), there is provided the method of any one of embodiments (41) through (44), wherein the diatomaceous earth is Celite®.

Methods of Making Compounds of the Invention

The present invention includes processes (i.e., methods) for preparing compounds of Formula I. Compounds of Formula I may be prepared according to the following reaction schemes and accompanying discussions. Variable group definitions for R$^1$, R$^2$, R$^3$, R$^4$, R$^5$, R$^6$, Het$^1$, Het$^2$, R$^a$, R$^b$, L, m, n and p in the following reaction schemes and discussions are as defined for Formula I, unless expressly indicated otherwise. As readily understood by a person of ordinary skill in the art, synthetic intermediates optionally include one or more protecting groups which are added and removed enroute to the target compound.

The present invention includes isotopically-labeled compounds of Formula I. For example, a compound of Formula I may contain one or more isotopic atoms such as deuterium $^2$H (or D) in place of proton $^1$H (or H), or $^{13}$C in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accordance with the preparations described by use of isotopically enriched reagents.

Isotopically-labeled compounds of the present invention are identical to those recited herein, except that one or more atoms in the compound is replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl and $^{123}$I, respectively.

The present invention further provides synthetic intermediates and compounds formed by the Schemes set forth herein. Compounds of the invention may be synthesized in a variety of ways known to those skilled in the art.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

As shown in the following schemes, one starting material for compounds of Formula I is cyclosporin A (CAS Number 59865-13-3). Cyclosporin A may be obtained commercially from suppliers such as Sigma-Aldrich (St. Louis, Mo., U.S.A.) or TCI America (Portland, Oreg., U.S.A.). Another cyclosporin starting material used for preparing compounds of Formula I is cyclosporin D (CAS Registry Number 63775-96-2), which may also be obtained through commercial suppliers, such as Enzo Life Sciences (Ann Arbor, Mich., U.S.A.; Farmingdale, N.Y., U.S.A.). Additional starting materials for compounds of Formula I include other cyclosporins, such as Cyclosporin B, Cyclosporin C, and Cyclosporin G, each which may be prepared from cyclosporin A as described by M. Mutter et al. *Tet. Lett.* 2000, 41, 7193-7196 and U.S. Pat. No. 5,214,130.

All the reagents, solvents, and catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa Aeser, Fisher, Maybridge, Frontier, Matrix, Ukrorgsynth, Toronto, Ryan Scientific, SiliCycle, Anaspec, Syn Chem, Chem-Impex, MIC-scientific, Ltd, and Synthonix. Some known intermediates were prepared according to published procedures. For example, (triphenylphosphoranyl)ethyl)morpholine bromide was prepared as described in Tetrahedron, 2008, 49, 824; 2-((triphenylphosphoranyl)methyl)pyrazine chloride was prepared as described in U.S. Pat. No. 4,826,833; 2-((triphenylphosphoranyl)methyl)imidazo[1,2-a]pyridine chloride was prepared as described in WO 2011150156; 3-((triphenylphosphoranyl)methyl)pyridazine chloride is known in the art (EP 103264); N,N-dimethyl-4-((triphenylphosphoranyl)methyl)aniline bromide was prepared as described in Synth Comm, 1996, 26, 16, 3091; 1-methyl-5-((triphenylphosphoranyl)methyl)-1H-pyrazole chloride and 1-methyl-3-((triphenylphosphoranyl)methyl)-1H-pyrazole, chloride salt were prepared as described in J. Gen. Chem. USSR (Engl. Transl.), 1982, vol. 52, No. 11 pp. 2598-2605, 2297-2303; m-methoxyphenyl-$CH_2PPh_3$ chloride was prepared as described in Journal of the Chemical Society, Chemical Communications, 1974, pp. 11-12; 1-methyl-2-((triphenylphosphoranyl)methyl)-1H-imidazole chloride was prepared as described in WO 2009/150240; o-methylphenyl-$CH_2PPh_3$ bromide was prepared as described in EP 1602645 A1; 1-methyl-4-(4-((triphenylphosphoranyl)methyl)phenyl)piperazine bromide was prepared as described in New Journal of Chemistry, 2010, vol. 34, pp. 2612-2621.

Additional Wittig reagents are prepared as follows: 1-methyl-4-((triphenylphosphoranyl)methyl)-1H-imidazole chloride is prepared by treating 4-(chloromethyl)-1-methyl-1H-imidazole (commercially available) with triphenylphosphine under standard conditions known in the art to make the phosphonium salt; 1-methyl-4-((triphenylphosphoranyl)methyl)-1H-pyrazole chloride is prepared by treating 4-(chloromethyl)-1-methyl-1H-pyrazole hydrochloride (commercially available) with triphenylphosphine under standard conditions known in the art to make the phosphonium salt; 4-(4-((triphenylphosphoranyl)methyl)phenyl)morpholine bromide is prepared from 4-morpholinobenzoic acid (commercially available), by reducing the acid to the alcohol with lithium aluminum hydride, followed by conversion to the halide and then to the phosphonium salt by standard methods known in the art.

In general, characterization of the compounds was performed according to the following methods: proton nuclear magnetic resonance CH NMR) and carbon nuclear magnetic resonance ($^{13}C$ NMR) spectra were recorded on a Bruker 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, integrated intensity, assignment).

Electron spray mass spectra (ESMS) were recorded on a Micromass ZQ.

The following abbreviations used in the reaction schemes and accompanying discussions are defined as follows:

Ac —$C(O)CH_3$ (or "acyl")

THF tetrahydrofuran $P_2O_5$ diphosphorus pentoxide $Na_2SO_4$ sodium sulfate

MPLC medium pressure liquid chromatography $CDCl_3$ deuterated chloroform

DMF dimethylformamide

TBDMSOTf t-butyldimethylsilyl trifluoromethanesulphonate

TBAF tetra-n-butylammonium fluoride

HCl hydrochloric acid $MgSO_4$ magnesium sulfate $CH_2Cl_2$ dichloromethane

KI potassium iodide $CO_2$ carbon dioxide

TosMIC p-toluenesulfonylmethyl isocyanide

SCX silica-based strong cation exchange

KOH potassium hydroxide $C_6D_6$ deuterated benzene

PG protecting group

The following synthetic schemes illustrate how compounds according to the invention can be made. Those skilled in the art will routinely be able to modify and/or adapt the following schemes to synthesize any compound of the invention covered by Formula I.

Starting materials for the synthesis of compounds of the invention include a compound of Formula II:

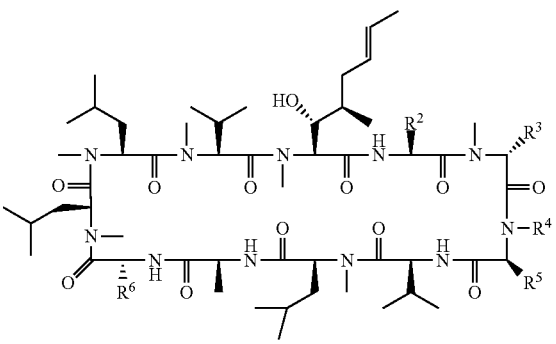

Formula II wherein:

R² is —CH₃, —CH₂CH₃, —CH(CH₃)₂, —CH₂CH₂CH₃ or —CH(CH₃)(OH);

R³ is —H, —C₁₋₆alkyl, —OC₁₋₆alkyl, —SC₁₋₆alkyl, —CH₂OH, —CH₂OCH₃,

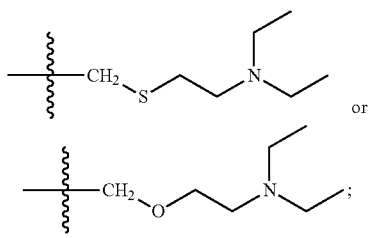

R⁴ is —CH₃ or —CH₂CH₃;

R⁵ is —CH(CH₃)₂, —CH₂CH(CH₃)₂, —CH₂C(CH₃)₂(OH), —CH(CH₃)(CH₂CH₃) or —CH₂CH(Rᶜ)(CH₂CH₃), wherein Rᶜ is OC₁₋₆ alkyl; and R⁶ is —CH₃ or —CH₂OH;

or a salt thereof.

In some aspects, the starting material for the synthesis of compounds of the invention is a compound of Formula IIa:

Formula IIa

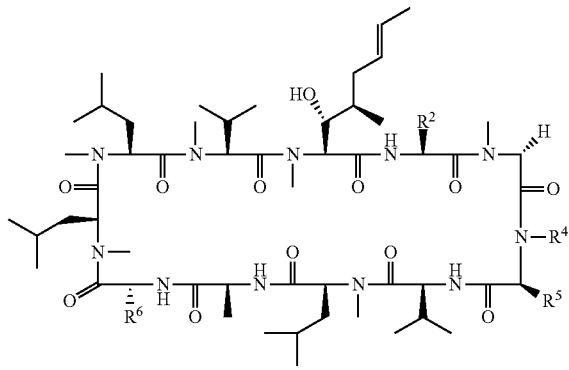

(the compound of Formula II wherein R³ is H)

wherein:

R² is —CH₃, —CH₂CH₃, —CH(CH₃)₂, —CH₂CH₂CH₃ or —CH(CH₃)(OH);

R⁴ is —CH₃ or —CH₂CH₃;

R⁵ is —CH(CH₃)₂, —CH₂CH(CH₃)₂, —CH₂C(CH₃)₂(OH), —CH(CH₃)(CH₂CH₃) or —CH₂CH(Rᶜ)(CH₂CH₃), wherein Rᶜ is OC₁₋₆ alkyl; and R⁶ is —CH₃ or —CH₂OH;

or a salt thereof.

In some aspects, the compound of Formula II is cyclosporin A, B, D or G.

In some aspects, a compound of Formula II is used to prepare a synthetic intermediate compound of Formula III, having the following structure:

Formula III

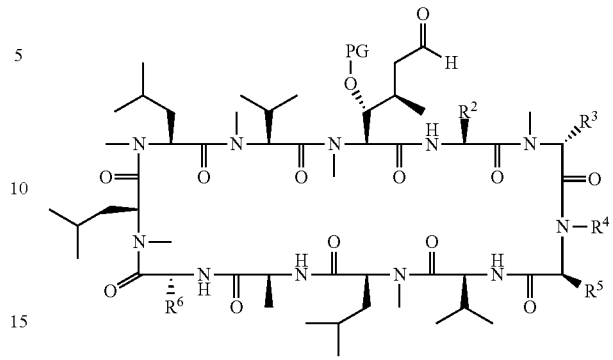

wherein:

R² is —CH₃, —CH₂CH₃, —CH(CH₃)₂, —CH₂CH₂CH₃ or —CH(CH₃)(OH);

R³ is —H, —C₁₋₆alkyl, —OC₁₋₆alkyl, —SC₁₋₆alkyl, —CH₂OH, —CH₂OCH₃, —CH₂OAc,

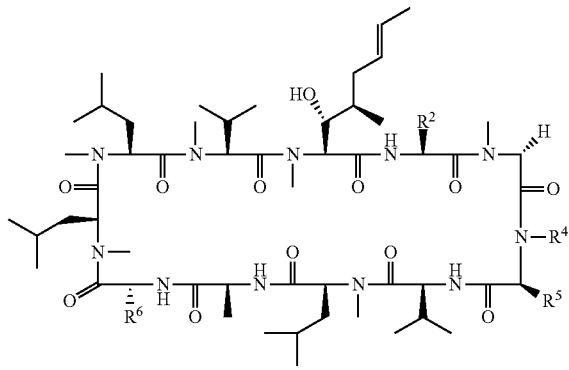

R⁴ is —CH₃ or —CH₂CH₃;

R⁵ is —CH(CH₃)₂, —CH₂CH(CH₃)₂, —CH₂C(CH₃)₂(OH), —CH(CH₃)(CH₂CH₃) or —CH₂CH(Rᶜ)(CH₂CH₃), wherein Rᶜ is OC₁₋₆ alkyl;

R⁶ is —CH₃ or —CH₂OH; and

PG is any suitable protecting group, preferably —C(O)CH₃ or —Si(Me)₂(t-Bu); or a salt thereof.

In some aspects, the compound of Formula II is used to prepare a synthetic intermediate compound of Formula IIIa, having the following structure:

Formula IIIa

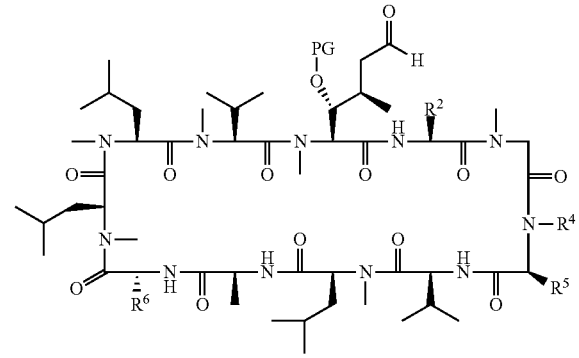

(the compound of Formula III wherein R³ is H)

wherein:

R² is —CH₃, —CH₂CH₃, —CH(CH₃)₂, —CH₂CH₂CH₃ or —CH(CH₃)(OH);

$R^4$ is —$CH_3$ or —$CH_2CH_3$;

$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;

$R^6$ is —$CH_3$ or —$CH_2OH$; and

PG is any suitable protecting group, preferably —$C(O)CH_3$ or —$Si(Me)_2(t$-$Bu)$; or a salt thereof.

In some aspects, the compound of Formula II is used to prepare a synthetic intermediate compound of Formula IIIb, having the following structure:

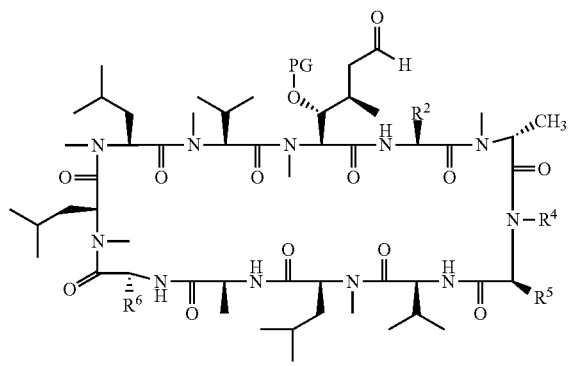

Formula IIIb (the compound of Formula III wherein $R^3$ is $CH_3$)

wherein:

$R^2$ is —$CH_3$, —$CH_2CH_3$, —$CH(CH_3)_2$, —$CH_2CH_2CH_3$ or —$CH(CH_3)(OH)$;

$R^4$ is —$CH_3$ or —$CH_2CH_3$;

$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;

$R^6$ is —$CH_3$ or —$CH_2OH$; and

PG is any suitable protecting group, preferably —$C(O)CH_3$ or —$Si(Me)_2(t$-$Bu)$; or a salt thereof.

In some aspects, the compound of Formula II is used to prepare a synthetic intermediate compound of Formula IIIc:

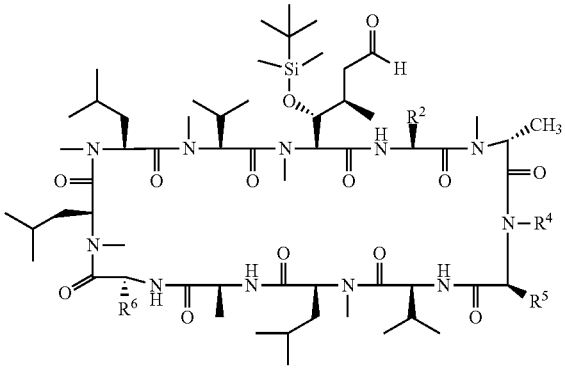

Formula IIIc wherein:

$R^2$ is —$CH_3$, —$CH_2CH_3$, —$CH(CH_3)_2$, —$CH_2CH_2CH_3$ or —$CH(CH_3)(OH)$;

$R^4$ is —$CH_3$ or —$CH_2CH_3$;

$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl; and $R^6$ is —$CH_3$ or —$CH_2OH$;

or a salt thereof.

In further aspects, there is provided a method of converting a compound of Formula II to a compound of Formula III. As shown in Scheme 1a, the MeBmt hydroxyl group of the compound of Formula II is protected with a suitable protecting group (PG), followed by ozonolysis to provide a compound of Formula III.

Scheme 1a. A procedure for preparing intermediates of Formula III.

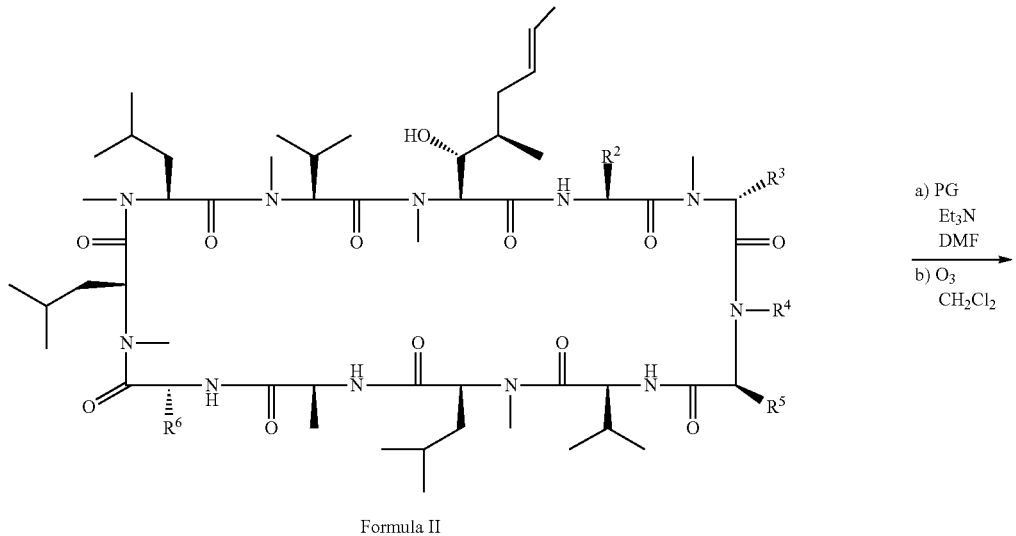

Formula II

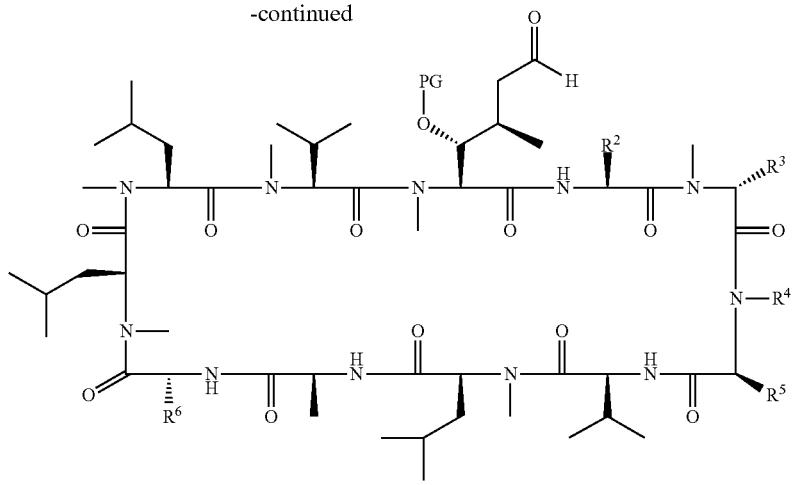

Formula III

The method provides for (but is not limited to) the synthesis of intermediates of Formula IIIa. For example, starting with cyclosporin A, the MeBmt hydroxyl group is protected with a suitable protecting group, such as —Si(Me)$_2$(t-Bu), followed by ozonolysis to provide Intermediate 7 (see Example A).

Intermediate 7

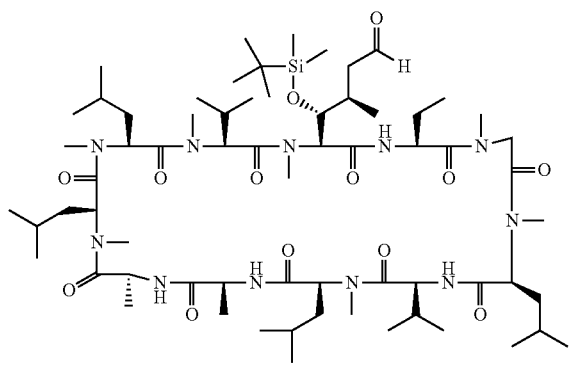

In a further example, starting with cyclosporin B, the MeBmt hydroxyl group is protected with a suitable protecting group, for example, —Ac or —Si(Me)$_2$(t-Bu), followed by ozonolysis to provide an intermediate of Formula IIIa wherein R$^2$ is methyl, R$^4$ is methyl, R$^5$ is —CH$_2$CH(CH$_3$)$_2$ and R$^6$ is methyl.

In yet a further example, starting with cyclosporin D, the MeBmt hydroxyl group is protected with a suitable protecting group, for example, —Ac or —Si(Me)$_2$(t-Bu), followed by ozonolysis to provide an intermediate of Formula IIIa wherein R$^2$ is —CH(CH$_3$)$_2$, R$^4$ is methyl, R$^5$ is —CH$_2$CH(CH$_3$)$_2$ and R$^6$ is methyl.

The method further provides for the synthesis of intermediates of Formula III wherein R$^3$ is —OCH$_3$. For example, the MeBmt hydroxyl group of Intermediate 12 (see Example A) is protected with a suitable protecting group, such as —Ac or —Si(Me)$_2$(t-Bu), followed by ozonolysis to provide an intermediate of Formula III wherein R$^2$ is ethyl, R$^3$ is —OCH$_3$, R$^4$ is methyl, R$^5$ is —CH$_2$CH(CH$_3$)$_2$ and R$^6$ is methyl.

Also provided is a method for preparing compounds of the invention wherein R$^3$ is methyl, as shown in Scheme 1b. Starting with compound of Formula IIa, an exocyclic olefin (R$^3$ is (=CH$_2$)) is introduced to provide a compound of Formula II'. The compound of Formula II' is protected and then undergoes ozonolysis to provide the aldehyde of Formula III'. The exocyclic double bond is subsequently reduced to provide an intermediate of Formula IIIb.

Scheme 1b. A procedure for preparing intermediates of Formula IIIb.

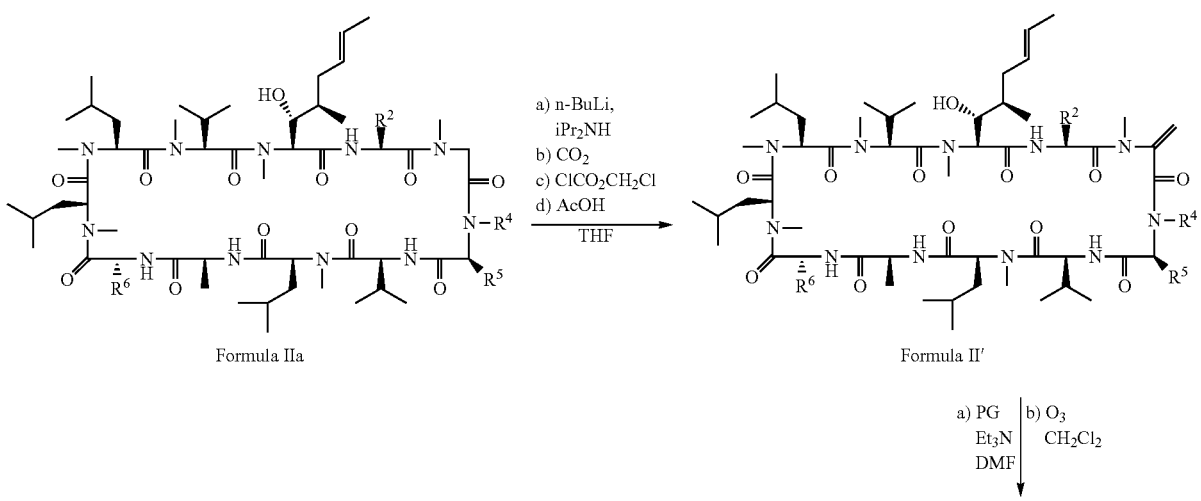

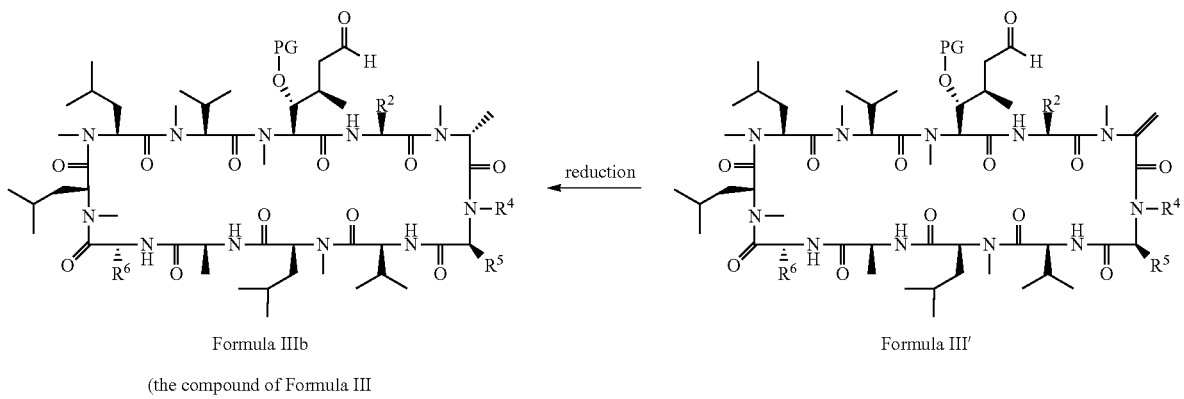

Formula IIIb
(the compound of Formula III wherein $R^3$ is $CH_3$)

reduction

Formula III'

For example, cyclosporin A was modified as shown in Scheme 1b to introduce an exocyclic olefin, thereby providing Intermediate 1; subsequent protection with Si(Me)$_2$(t-Bu) gave Intermediate 2, which was subjected to ozonolysis to provide Intermediate 3. The exocyclic double bond was subsequently reduced to provide Intermediate 4 (see Example A).

In another example, cyclosporin B is modified as described in Scheme 1b to introduce an exocyclic olefin, followed by protection and ozonolysis; the exocyclic double bond is subsequently reduced to provide the compound of Formula IIIc wherein $R^2$ is methyl, $R^3$ is methyl, $R^4$ is methyl, $R^5$ is —CH$_2$CH(CH$_3$)$_2$ and $R^6$ is methyl.

In a further example, cyclosporin D is modified as described in Scheme 1b to introduce an exocyclic olefinic compound, followed by protection, ozonolysis and reduction of the exocyclic double bond to provide the compound of Formula IIIc wherein $R^2$ is —CH(CH$_3$)$_2$, $R^4$ is methyl, $R^5$ is —CH$_2$CH(CH$_3$)$_2$ and $R^6$ is methyl.

In further aspects, there are provided compounds of Formula VII and methods of making the same, wherein the compound of Formula VII has the following structure:

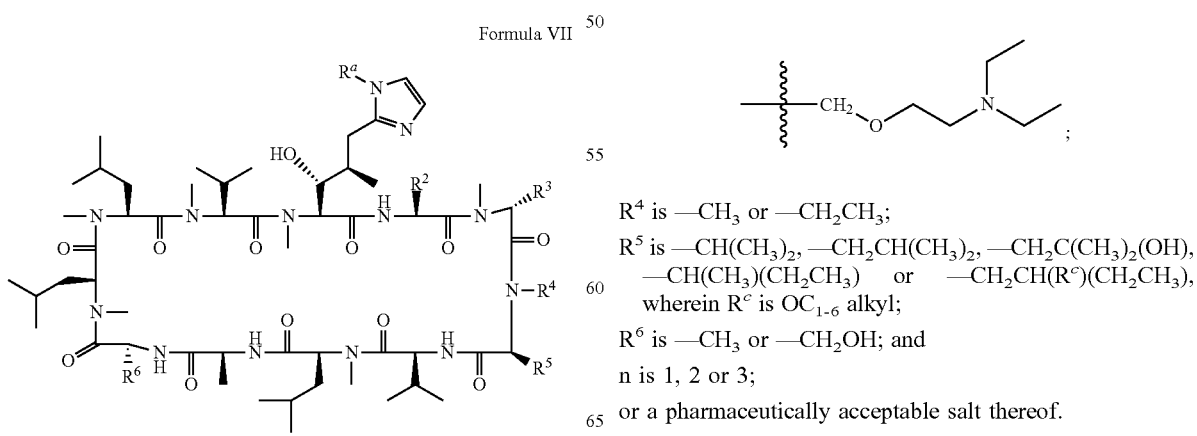

Formula VII wherein:

$R^a$ is selected from the group consisting of halogen, —C$_{1-6}$ alkyl, —OC$_{1-6}$ alkyl and —(CH$_2$)$_n$R$^b$;

wherein R$^b$ is selected from Het$^2$, —C$_{1-6}$ haloalkyl, —OH, —NH$_2$, —NH(C$_{1-6}$ alkyl), —N(C$_{1-6}$alkyl)$_2$ wherein each C$_{1-6}$ alkyl is the same or different; and wherein Het$^2$ is a heterocyclyl optionally substituted with one or more halogen, —C$_{1-6}$ alkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl), —(CH$_2$)$_{1-6}$N(C$_{1-6}$ alkyl)$_2$ or —C$_{1-6}$ haloalkyl;

$R^2$ is —CH$_3$, —CH$_2$CH$_3$, —CH(CH$_3$)$_2$, —CH$_2$CH$_2$CH$_3$ or —CH(CH$_3$)(OH);

$R^3$ is —H, —C$_{1-6}$alkyl, —OC$_{1-6}$alkyl, —SC$_{1-6}$alkyl, —CH$_2$OH, —CH$_2$OCH$_3$, $$\text{-CH}_2\text{-S-CH}_2\text{CH}_2\text{-N(CH}_2\text{CH}_3\text{)}_2 \quad \text{or}$$

$$\text{-CH}_2\text{-O-CH}_2\text{CH}_2\text{-N(CH}_2\text{CH}_3\text{)}_2;$$

$R^4$ is —CH$_3$ or —CH$_2$CH$_3$;

$R^5$ is —CH(CH$_3$)$_2$, —CH$_2$CH(CH$_3$)$_2$, —CH$_2$C(CH$_3$)$_2$(OH), —CH(CH$_3$)(CH$_2$CH$_3$) or —CH$_2$CH(R$^c$)(CH$_2$CH$_3$), wherein R$^c$ is OC$_{1-6}$ alkyl;

$R^6$ is —CH$_3$ or —CH$_2$OH; and n is 1, 2 or 3;

or a pharmaceutically acceptable salt thereof.

Compounds of Formula VII can be prepared as shown in Scheme 2.

Scheme 2. Route to Imidazole Compounds of Formula VII (i.e., compounds of Formula I, wherein Het[1] is optionally substituted imidazole, m is 1 and L is absent.
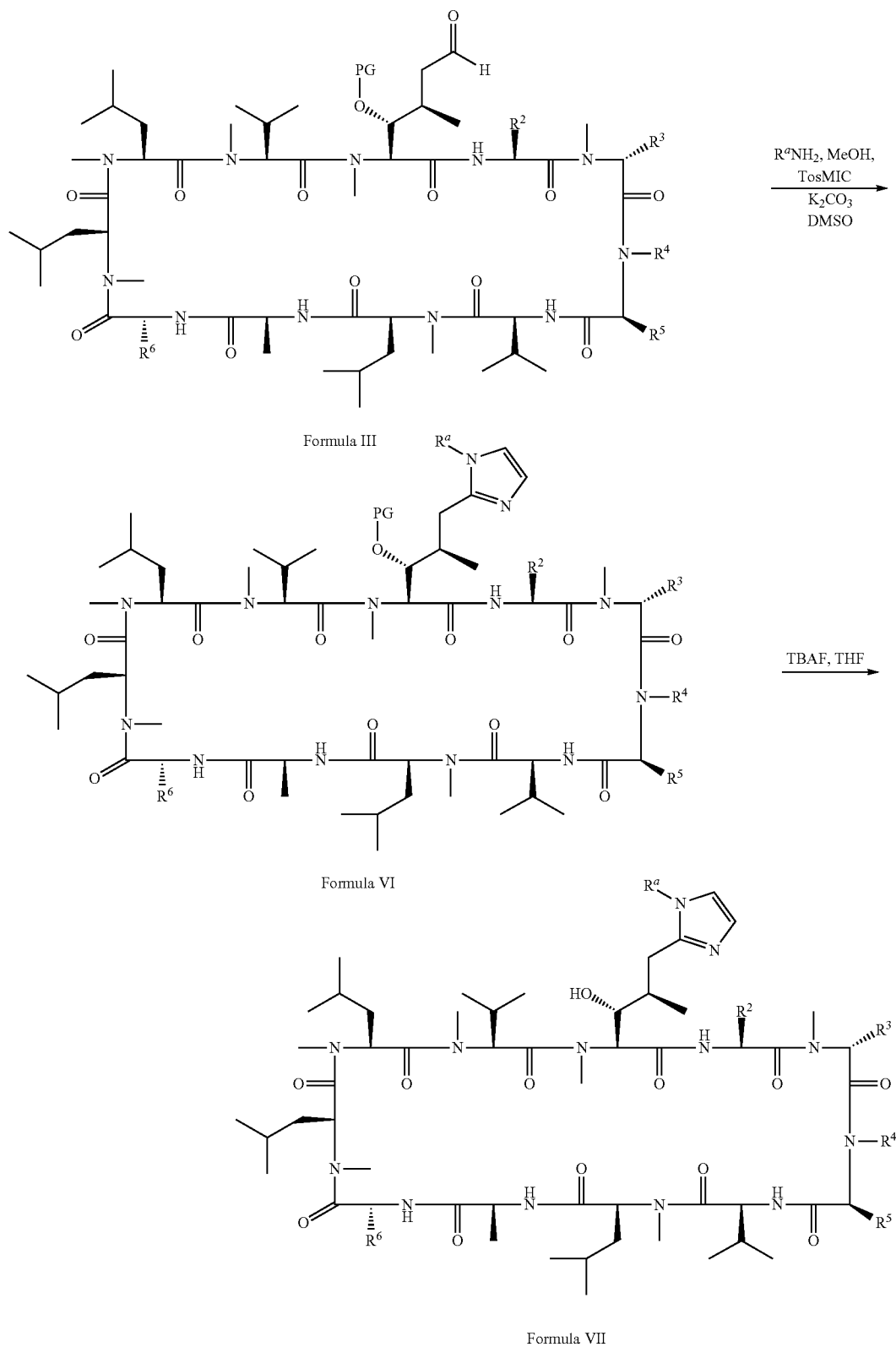

Briefly, a compound of Formula III is reacted with an optionally substituted amine to provide an intermediate of Formula VI, which is subsequently deprotected to provide a compound of Formula VII wherein Het[1] is an optionally substituted imidazole. For example, as described in Example A, Intermediate 4 was reacted with methylamine to provide Intermediate 5 ($R^a$ is methyl), which was subsequently deprotected to give Compound 1 (see Example 1).

Other compounds of the invention are prepared by using different amines in place of methylamine. For example, ethylamine is used in place of methylamine to provide a compound of Formula VII wherein $R^a$ is ethyl. In another example, an amino compound $H_2N(CH_2)_nR^b$ (wherein n and $R^b$ are as defined for Formula I) is reacted with Intermediate 4 to provide compounds of Formula VII wherein $R^a$ is $—(CH_2)_nR^b$. In a particular example, reaction of 3,3,3-trifluoropropan-1-amine with Intermediate 4 followed by deprotection gave Compound 8.

In further aspects, there are provided compounds of Formula IX and methods of making the same, wherein the compound of Formula IX has the following structure:

Formula IX

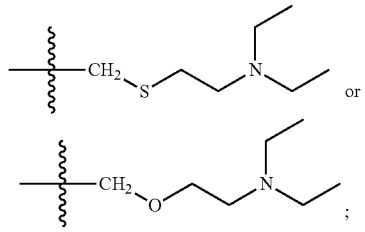

wherein:
each $R^a$ is independently selected from the group consisting of halogen, $—C_{1-6}$ alkyl, $—OC_{1-6}$ alkyl and $—(CH_2)_nR^b$;
wherein each $R^b$ is independently selected from Het[2], $—C_{1-6}$ haloalkyl, $—OH$, $—NH_2$, $—NH(C_{1-6}$ alkyl), $—N(C_{1-6}$ alkyl)$_2$ wherein each $C_{1-6}$ alkyl is the same or different; and
wherein each Het[2] is independently a heterocyclyl optionally substituted with one or more halogen, $—C_{1-6}$ alkyl, $—OC_{1-6}$alkyl, $—(CH_2)_{1-6}OH$, $—(CH_2)_{1-6}NH_2$, $—(CH_2)_{1-6}NH(C_{1-6}$ alkyl), $—(CH_2)_{1-6}N(C_{1-6}$ alkyl)$_2$ or $—C_{1-6}$ haloalkyl;
$R^2$ is $—CH_3$, $—CH_2CH_3$, $—CH(CH_3)_2$, $—CH_2CH_2CH_3$ or $—CH(CH_3)(OH)$;
$R^3$ is $—H$, $—C_{1-6}$alkyl, $—OC_{1-6}$alkyl, $—SC_{1-6}$alkyl, $—CH_2OH$, $—CH_2OCH_3$,

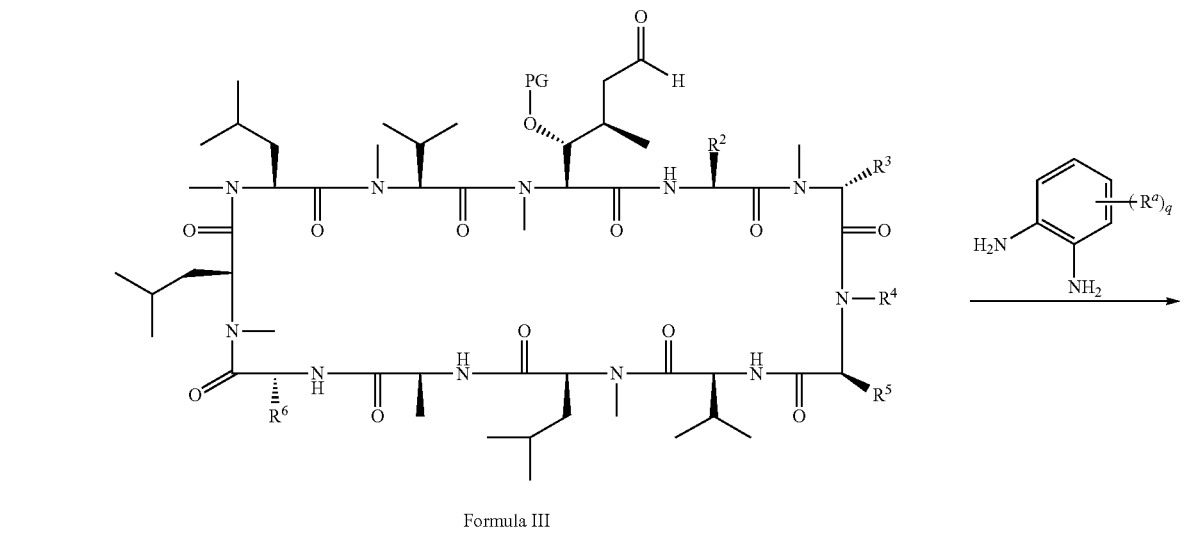

$R^4$ is $—CH_3$ or $—CH_2CH_3$;
$R^5$ is $—CH(CH_3)_2$, $—CH_2CH(CH_3)_2$, $—CH_2C(CH_3)_2(OH)$, $—CH(CH_3)(CH_2CH_3)$ or $—CH_2CH(R^c)(CH_2CH_3)$, wherein $R^c$ is $OC_{1-6}$ alkyl;
$R^6$ is $—CH_3$ or $—CH_2OH$;
n is 1, 2 or 3; and
q is 0, 1, 2, 3 or 4;
or a pharmaceutically acceptable salt thereof.

Compounds of Formula IX can be prepared as shown in Scheme 3. Briefly, the compounds are prepared by reacting a compound of Formula III with diaminobenzene optionally substituted with $R^a$, to provide a compound of Formula VIII, which is subsequently deprotected to provide a compound of Formula IX.

Scheme 3. Route to Benzimidazole Compounds of Formula IX (i.e., compounds of Formula I wherein m is 1, L is absent, and Het[1] is a substituted or unsubstituted benzimidazole) are prepared as shown below; q is 0, 1, 2, 3 or 4.

Formula III

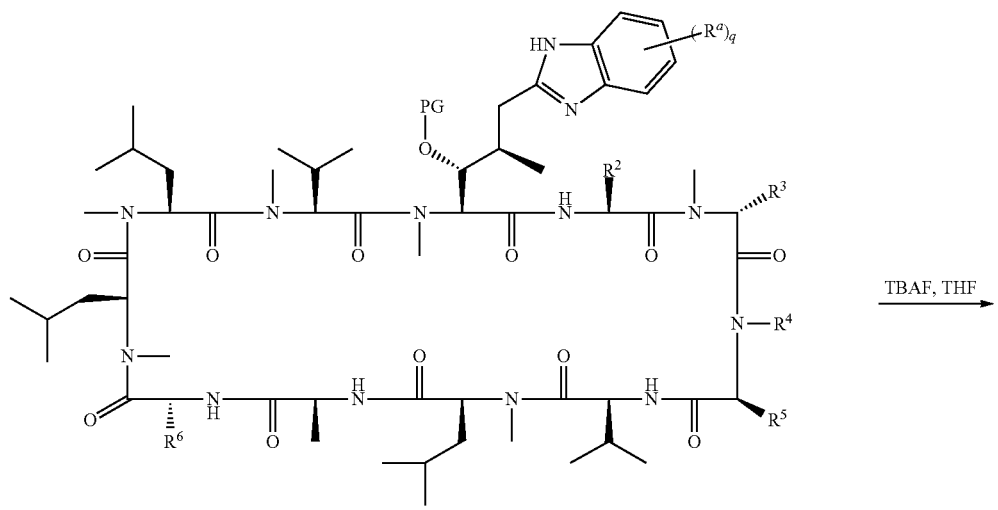

Formula VIII

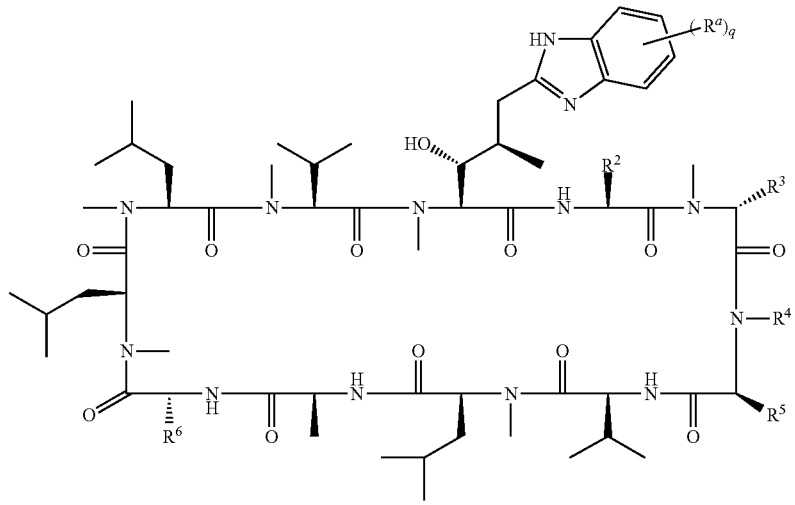

Formula IX

For example, Intermediate 4 was reacted with 1,2-diaminobenzene to provide Intermediate 6, which was subsequently deprotected to give Compound 9; in another example, Intermediate 7 was reacted with 1,2-diaminobenzene, and the product was deprotected to give Compound 10 (see Examples 9 and 10).

Other compounds of the invention can be prepared by using a suitable, optionally substituted diamine in place of diaminobenzene. For example, an optionally substituted 1,2-diaminocyclohexane or 1,2-diaminocyclohexene can be used to provide a compound of Formula V having the following structure:

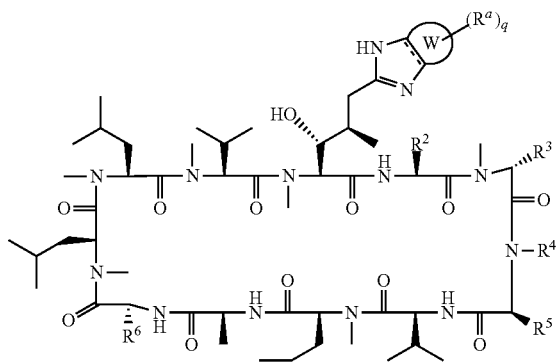

Formula V wherein:
W is a 5- or 6-membered cycloalkyl, cycloalkenyl or heterocyclic ring;
each $R^a$ is independently selected from the group consisting of halogen, —$C_{1-6}$ alkyl, —$OC_{1-6}$ alkyl and —$(CH_2)_nR^b$;
wherein each $R^b$ is independently selected from Het², —$C_{1-6}$ haloalkyl, —OH, —$NH_2$, —$NH(C_{1-6}$ alkyl), —$N(C_{1-6}$ alkyl)$_2$ wherein each $C_{1-6}$ alkyl is the same or different, and
wherein each Het² is independently a heterocyclyl optionally substituted with one or more halogen, —$C_{1-6}$ alkyl, —$OC_{1-6}$alkyl, —$(CH_2)_{1-6}OH$, —$(CH_2)_{1-6}NH_2$, —$(CH_2)_{1-6}NH(C_{1-6}$ alkyl), —$(CH_2)_{1-6}N(C_{1-6}$ alkyl)$_2$ or —$C_{1-6}$ haloalkyl;
$R^2$ is —$CH_3$, —$CH_2CH_3$, —$CH(CH_3)_2$, —$CH_2CH_2CH_3$ or —$CH(CH_3)(OH)$;
$R^3$ is —H, —$C_{1-6}$alkyl, —$OC_{1-6}$alkyl, —$SC_{1-6}$alkyl, —$CH_2OH$, —$CH_2OCH_3$,

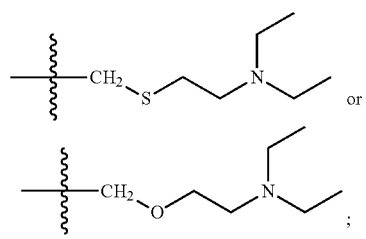

or

;

$R^4$ is —$CH_3$ or —$CH_2CH_3$;
$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
$R^6$ is —$CH_3$ or —$CH_2OH$;
n is 1, 2 or 3;
q is 0, 1, 2, 3 or 4; and
wherein the dashed line is a double or single bond;
or a pharmaceutically acceptable salt thereof.

In further aspects, there are provided compounds of Formula XII and methods of making the same, wherein the compound of Formula XII has the following structure:

Formula XII

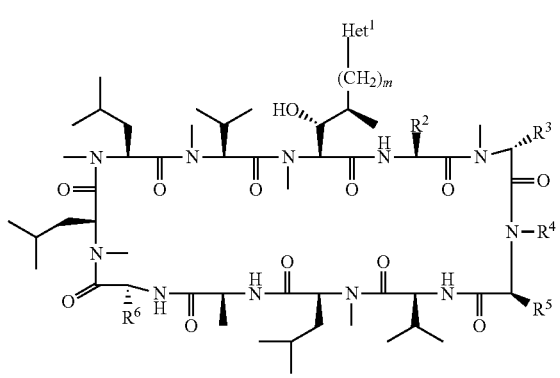

wherein:

Het¹ is a heterocyclyl optionally substituted with one or more $R^a$;
wherein each $R^a$ is independently selected from the group consisting of halogen, —$C_{1-6}$ alkyl, —$OC_{1-6}$ alkyl and —$(CH_2)_nR^b$;
wherein each $R^b$ is independently selected from Het², —$C_{1-6}$ haloalkyl, —OH, —$NH_2$, —$NH(C_{1-6}$ alkyl), —$N(C_{1-6}$ alkyl)$_2$ wherein each $C_{1-6}$ alkyl is the same or different, and
wherein each Het² is independently a heterocyclyl optionally substituted with one or more halogen, —$C_{1-6}$ alkyl, —$OC_{1-6}$alkyl, —$(CH_2)_{1-6}OH$, —$(CH_2)_{1-6}NH_2$, —$(CH_2)_{1-6}NH(C_{1-6}$ alkyl), —$(CH_2)_{1-6}N(C_{1-6}$ alkyl)$_2$ or —$C_{1-6}$ haloalkyl;
$R^2$ is —$CH_3$, —$CH_2CH_3$, —$CH(CH_3)_2$, —$CH_2CH_2CH_3$ or —$CH(CH_3)(OH)$;
$R^3$ is —H, —$C_{1-6}$alkyl, —$OC_{1-6}$alkyl, —$SC_{1-6}$alkyl, —$CH_2OH$, —$CH_2OCH_3$,

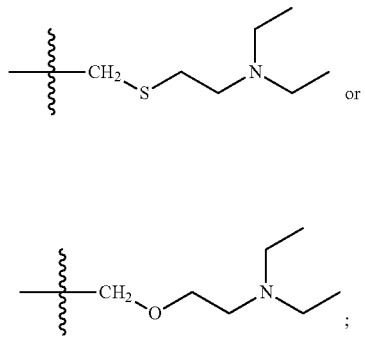

or

;

$R^4$ is —$CH_3$ or —$CH_2CH_3$;
$R^5$ is —$CH(CH_3)_2$, —$CH_2CH(CH_3)_2$, —$CH_2C(CH_3)_2(OH)$, —$CH(CH_3)(CH_2CH_3)$ or —$CH_2CH(R^c)(CH_2CH_3)$, wherein $R^c$ is $OC_{1-6}$ alkyl;
$R^6$ is —$CH_3$ or —$CH_2OH$;
m is 1, 2, 3 or 4 (preferably 3 or 4); and
n is 1, 2 or 3;
or a pharmaceutically acceptable salt thereof.

Compounds of Formula XII can be prepared as shown in Scheme 4.

Scheme 4. The Wittig Route to Compounds of Formula XII (i.e., compounds of Formula I wherein m is 3 or 4, and L is absent) are prepared as shown below.
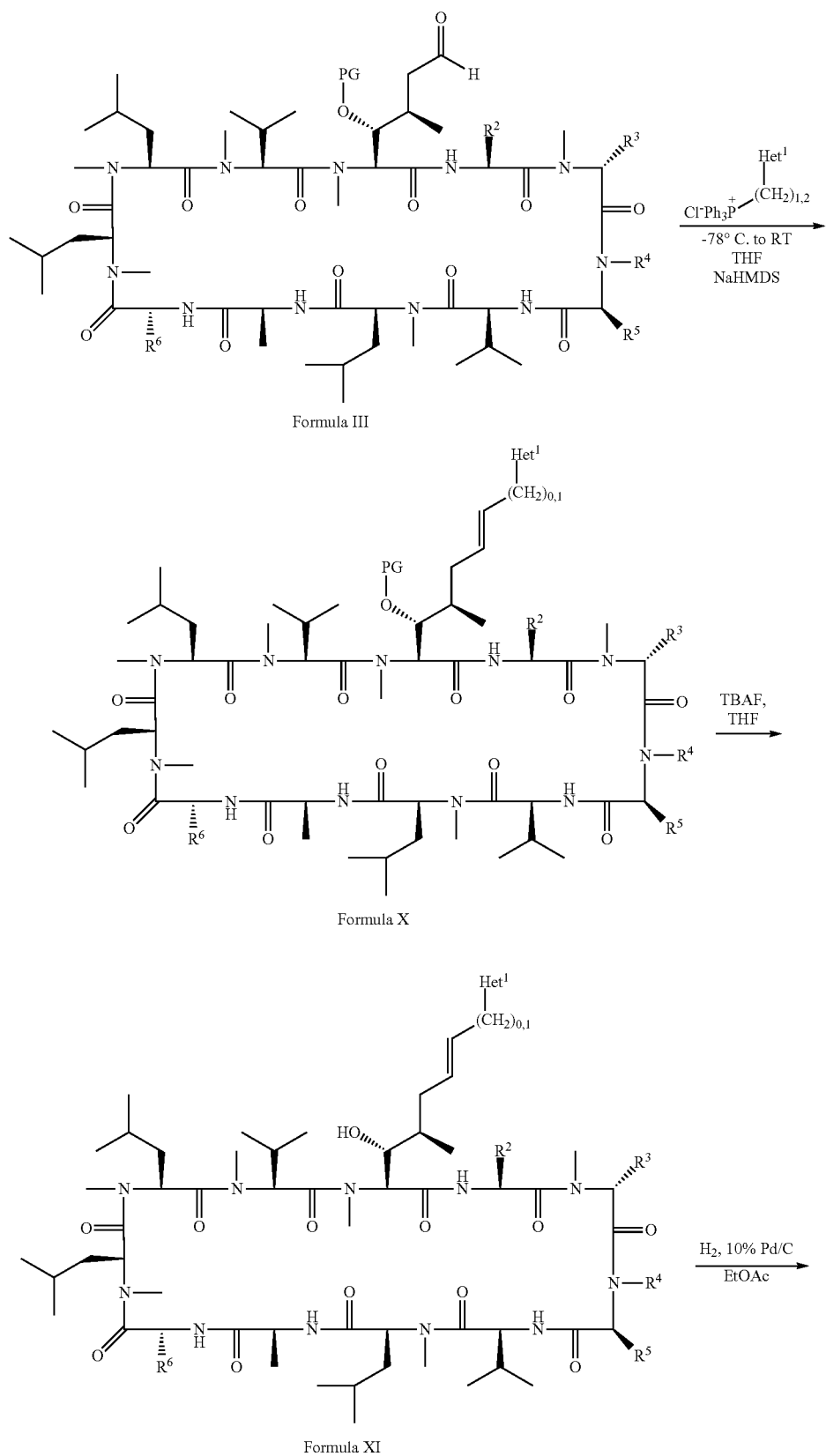

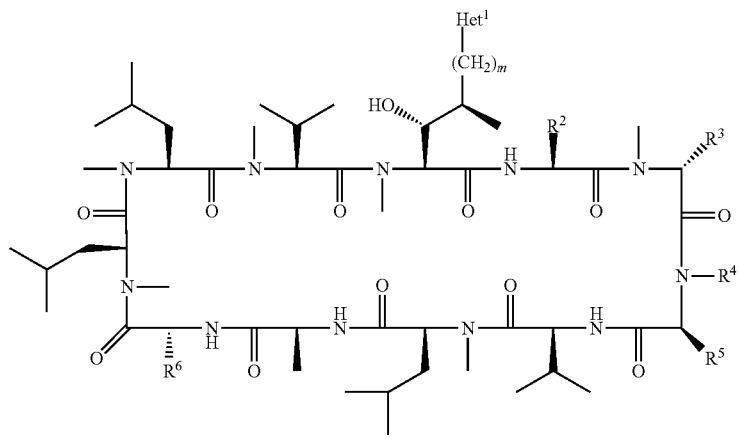

Formula XII

In further aspects, there are provided compounds of Formula XV and methods of making the same, wherein the compound of Formula XV has the following structure:

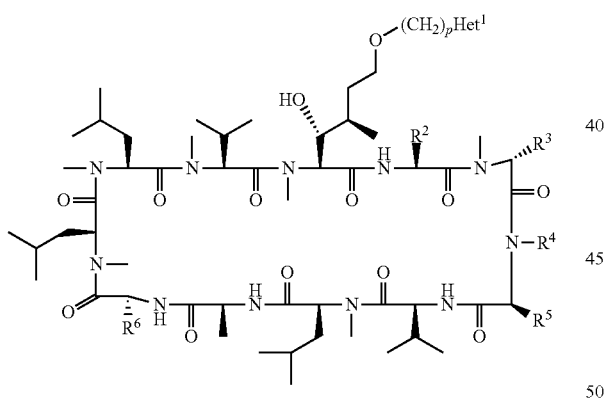

Formula XV wherein:

Het$^1$ is a heterocyclyl optionally substituted with one or more R$^a$;

wherein each R$^a$ is independently selected from the group consisting of halogen, —C$_{1-6}$ alkyl, —OC$_{1-6}$ alkyl and —(CH$_2$)$_n$R$^b$;

wherein each R$^b$ is independently selected from Het$^2$, —C$_{1-6}$ haloalkyl, —OH, —NH$_2$, —NH(C$_{1-6}$ alkyl), —N(C$_{1-6}$ alkyl)$_2$ wherein each C$_{1-6}$ alkyl is the same or different, and wherein Het$^2$ is a heterocyclyl optionally substituted with one or more halogen, —C$_{1-6}$ alkyl, —OC$_{1-6}$alkyl, —(CH$_2$)$_{1-6}$OH, —(CH$_2$)$_{1-6}$NH$_2$, —(CH$_2$)$_{1-6}$NH(C$_{1-6}$ alkyl), —(CH$_2$)$_{1-6}$N(C$_{1-6}$ alkyl)$_2$ or —C$_{1-6}$ haloalkyl;

R$^2$ is —CH$_3$, —CH$_2$CH$_3$, —CH(CH$_3$)$_2$, —CH$_2$CH$_2$CH$_3$ or —CH(CH$_3$)(OH);

R$^3$ is —H, —C$_{1-6}$alkyl, —OC$_{1-6}$alkyl, —SC$_{1-6}$alkyl, —CH$_2$OH, —CH$_2$OCH$_3$,

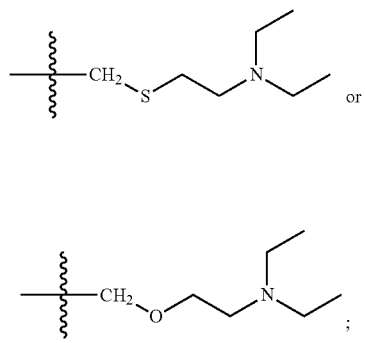

R$^4$ is —CH$_3$ or —CH$_2$CH$_3$;

R$^5$ is —CH(CH$_3$)$_2$, —CH$_2$CH(CH$_3$)$_2$, —CH$_2$C(CH$_3$)$_2$(OH), —CH(CH$_3$)(CH$_2$CH$_3$) or —CH$_2$CH(R$^c$)(CH$_2$CH$_3$), wherein R$^c$ is OC$_{1-6}$ alkyl;

R$^6$ is —CH$_3$ or —CH$_2$OH;

n is 1, 2 or 3; and p is 0 or 1;

or a pharmaceutically acceptable salt thereof.

Compounds of Formula XV can be prepared as shown in Scheme 5.

Scheme 5. The O-Aklylation Route; method to prepare compounds of Formula XV
(i.e., compounds of Formula I wherein m is 2, and L is —O—(CH$_2$)$_p$—).
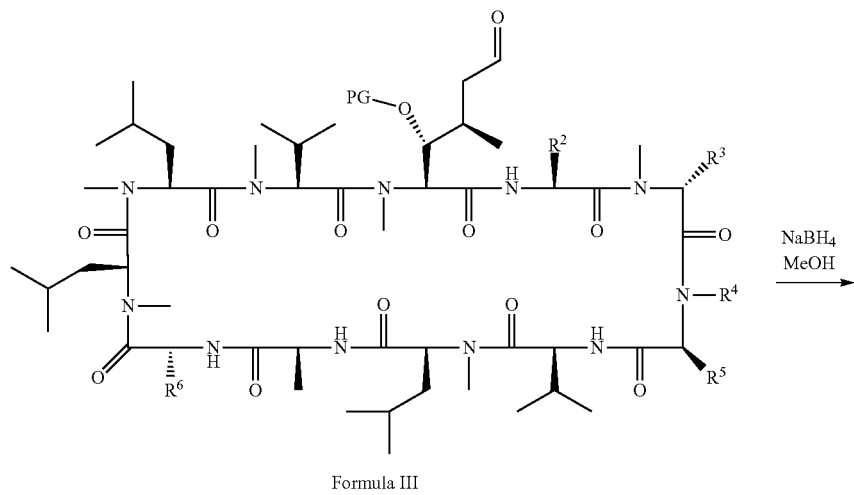
Formula III
NaBH$_4$
MeOH
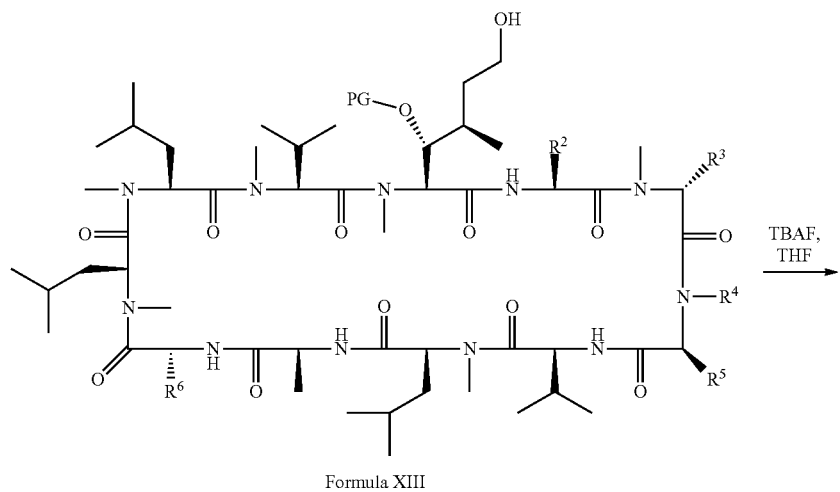
Formula XIII
TBAF,
THF
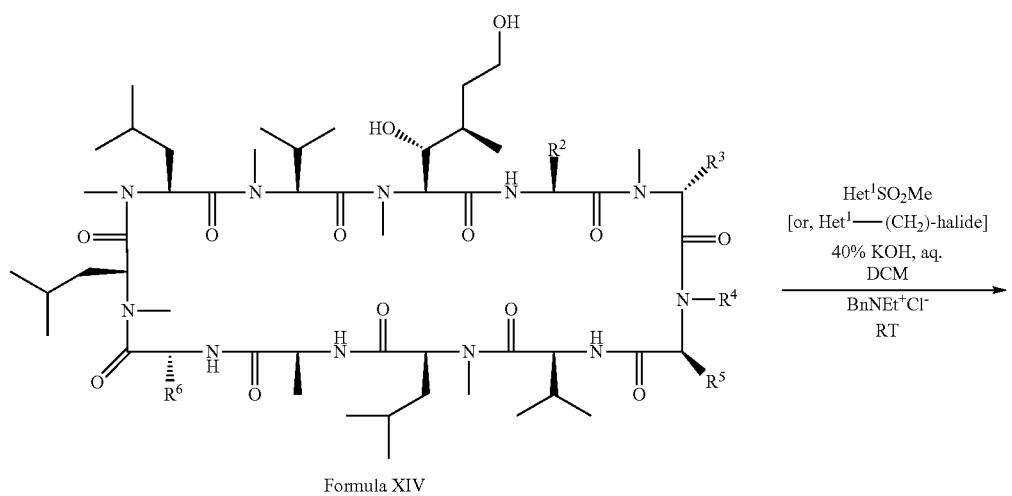
Formula XIV
Het$^1$SO$_2$Me
[or, Het$^1$—(CH$_2$)-halide]
40% KOH, aq.
DCM
BnNEt$^+$Cl$^-$
RT

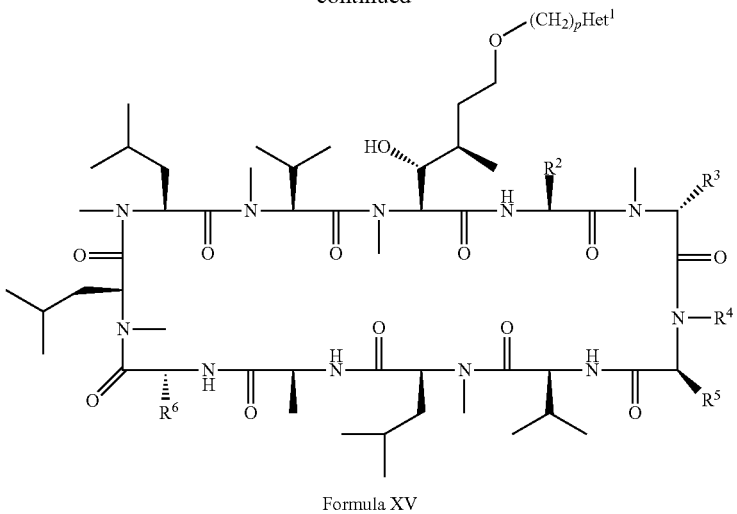

Formula XV

Example A—Synthesis of Intermediates

Intermediate 1: [Methylene-Sar]$^3$ cyclosporin A

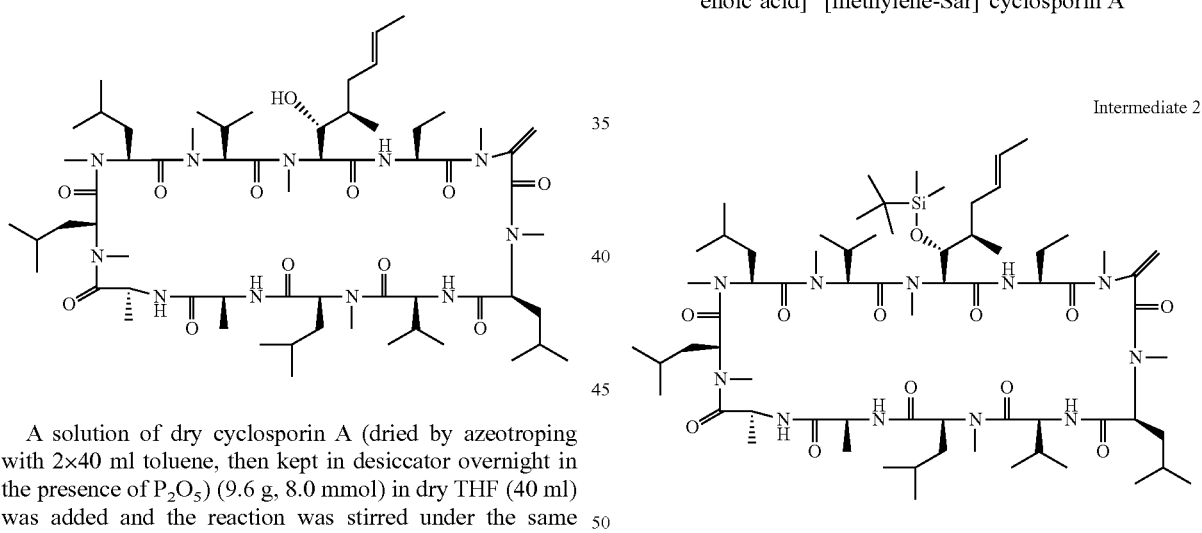

Intermediate 1

A solution of dry cyclosporin A (dried by azeotroping with 2×40 ml toluene, then kept in desiccator overnight in the presence of $P_2O_5$) (9.6 g, 8.0 mmol) in dry THF (40 ml) was added and the reaction was stirred under the same conditions for 2 h. A flow of carbon dioxide was bubbled through the reaction mixture for 30 minutes with temperature increasing to −50° C. The resulting mixture was allowed to warm to 15° C. over a period of 2 hours, then cooled back down to −50° C. before the addition of chloromethylchloroformate (7.1 ml, 80 mmol). The reaction mixture was allowed to warm to room temperature overnight, then cooled to 0° C., and acetic acid (5 ml, 88 mmol) was added.

The mixture was allowed to warm to room temperature, the solvent evaporated and the resultant mixture was partitioned between ethyl acetate and brine. The organic phase was separated, dried ($Na_2SO_4$) and concentrated to give a yellow oil. The crude product was purified by MPLC chromatography using a solvent gradient of 100% diethyl ether→96% diethyl ether/4% methanol to give Intermediate 1. ESMS MH$^+$ 1214.8, MNa$^+$ 1236.8; $^1$H NMR (CDCl$_3$, ppm) δ 4.98 (d, 1H, olefin CH$_2$), 5.25 (d, 1H, olefin CH$_2$), 7.17 (d, 1H, amide NH), 7.52 (d, 1H, amide NH), 7.59 (d, 1H, amide NH), 7.85 (d, 1H, amide NH); $^{13}$C NMR (CDCl$_3$, ppm) δ 143.96 (olefin C), 108.09 (olefin CH$_2$).

Intermediate 2: [(E,2S,3R,4R)-3-(t-Butyldimethylsilanyloxy)-4-methyl-2-1.5 (methylamino)-oct-6-enoic acid]$^1$ [methylene-Sar]$^3$cyclosporin A Intermediate 2

To a solution of Intermediate 1 (5 g, 4.12 mmol) in DMF (50 ml) at 0° C. under an atmosphere of nitrogen was added triethylamine (10 eq., 5.75 ml, 41.2 mmol) followed by a drop-wise addition of TBDMSOTf (5 eq, 4.5 ml, 20.6 mmol) (over 5 minutes) and the reaction mixture warmed to room temperature over 2 h. The reaction mixture was diluted with t-butyl methyl ether (200 ml), then washed with 2N HCl (100 ml), followed by H$_2$O (100 ml). The aqueous extracts were extracted with t-butyl methyl ether (100 ml), and the combined organic extracts washed with H$_2$O (2×100 ml), brine (100 ml), then dried (MgSO$_4$), filtered and evaporated under reduced pressure to yield Intermediate 2 as a viscous oil. The crude product was used in a subsequent step without further purification. $^1$H NMR (CDCl$_3$, ppm) δ 7.40 (d, 1H, amide NH), 7.79 (d, 1H, amide NH), 7.90 (d, 1H, amide NH), 8.28 (d, 1H, amide NH).

Intermediate 3: [(2S,3R,4R)-3-(t-butyldimethylsilanyloxy)-4-methyl-2-(methylamino)-6-oxo-hexanoic acid]¹[methylene-Sar]³ cyclosporin A

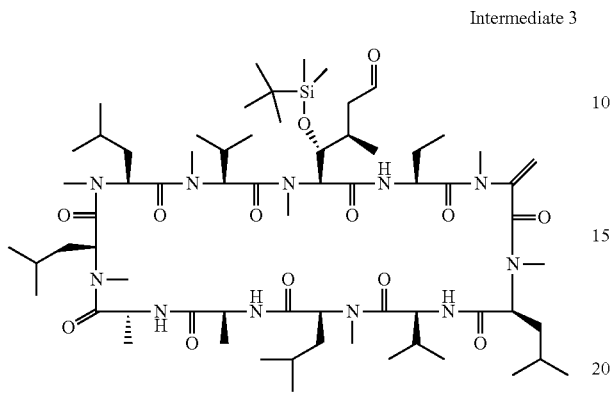

Intermediate 3

A solution of Intermediate 2 (9 g, approximately 4 mmol) was dissolved in $CH_2Cl_2$ (200 ml) and added to a 3-neck flask equipped with inlet (for nitrogen/ozone addition) and outlet connected to a Drechsel bottle containing 2M KI solution. The reaction mixture was cooled to −78° C. over a solid $CO_2$/acetone bath, under a nitrogen atmosphere. When the temperature of the reaction vessel had stabilized, the nitrogen was removed and ozone bubbled through the reaction mixture until it became a pale blue color (approx. 20 minutes). The ozone supply was removed and nitrogen bubbled through the reaction mixture until the blue color had gone, then dimethylsulphide (0.8 ml) was added, and the reaction mixture warmed to room temperature over 2 hours. After this time, the reaction mixture was washed with $H_2O$ (3×200 ml), then dried ($MgSO_4$), filtered and evaporated under reduced pressure to yield the crude product as a clear, viscous oil. The crude product was purified by MPLC chromatography using a solvent gradient of 100% hexane→40% ethyl acetate/60% hexane to give Intermediate 3 as a white solid. ESMS MH⁺ 1316.67; ¹H NMR ($CDCl_3$, ppm) δ 7.53 (d, 1H, amide NH), 7.75 (d, 1H, amide NH), 7.84 (d, 1H, amide NH), 8.33 (d, 1H, amide NH), 9.63 (s, 1H, aldehyde H).

Intermediate 4: [(2S,3R,4R)-3-(t-Butyldimethylsilanyloxy)-4-methyl-2-(methylamino)-6-oxo-hexanoic acid]¹ [(R)-methyl-Sar]³ cyclosporin A

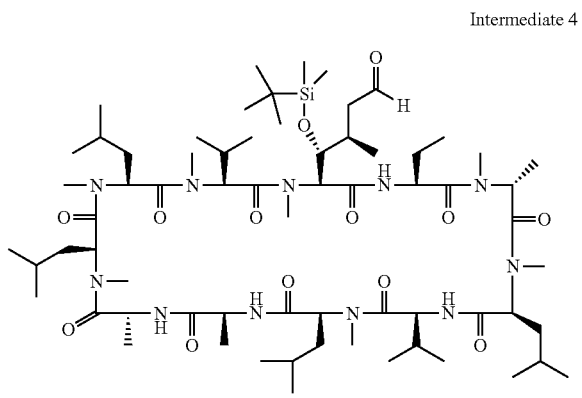 [SMILES: CC[C@H]1NC(=O)[C@@H]([C@H](O[Si](C)(C)C(C)(C)C)[C@H](C)CC=O)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Intermediate 4

To a solution of Intermediate 3 (1 g) in ethanol was added 10% palladium on carbon (0.5 g), and the reaction stirred under a hydrogen atmosphere for 18 h. After this time, the reaction mixture was filtered through a pad of Celite and washed with ethyl acetate. The solvent was evaporated to leave the Intermediate 4 as a fluffy white solid, obtained as a mixture of (R) and (S) isomers at the C3(α) position, approx>7:1 (R):(S). The crude product was used in a subsequent step without further purification.

ESMS MH⁺ 1318.77; ¹H NMR ($CDCl_3$, ppm) δ 7.57 (d, 1H, amide NH), 7.65 (d, 1H, amide NH), 7.89 (d, 1H, amide NH), 8.47 (d, 1H, amide NH), 9.63 (s, 1H, aldehyde H).

Intermediate 5: [(2S,3R,4R)-5-(1-Methyl-1H-imidazol-2-yl)-3-(t-butyldimethylsilanyloxy)-4-methyl-2-(methylamino)pentanoic acid]¹ [(R)-methyl-Sar]³ cyclosporin A

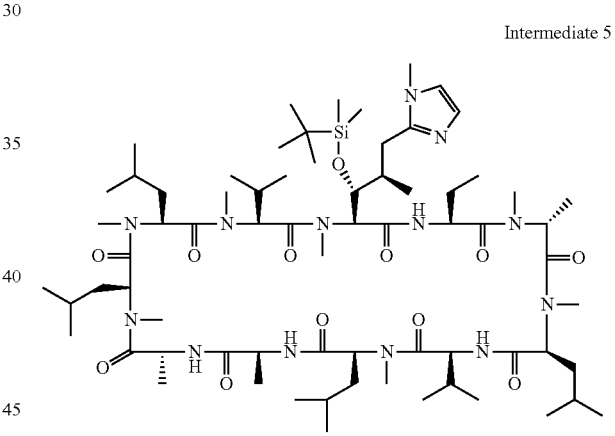

Intermediate 5

Intermediate 4 (150 mg, 0.11 mmol) was dissolved in methanol (2 mL). Methylamine in methanol (2M, 0.284 mL, 0.57 mmol) was added and the solution was stirred at room temperature for 2 hours. The reaction mixture was concentrated and the residue re-dissolved in DMSO (2 mL). Potassium carbonate (79 mg, 0.57 mmol) and TosMIC (67 mg, 0.34 mmol) were added and the reaction mixture was left to stir for 18 hours. The reaction mixture was diluted with water (5 mL) and dichloromethane (10 mL). The layers were separated and the aqueous layer re-extracted with dichloromethane (2×10 mL). The combined organic extracts were dried over magnesium sulfate and purified on a SCX column eluting with methanol and then ammonia in methanol (0.35M) to give Intermediate 5 which was used as such in a subsequent reaction.

ES/MS: 1371.0 MH⁺.

Intermediate 6: [(2S,3R,4R)-5-(1H-Benzimidazol-2-yl)-3-(t-butyldimethylsilanyloxy)-4-methyl-2-(methylamino) pentanoic acid][1] [(R)-methyl-Sar][3] cyclosporin A

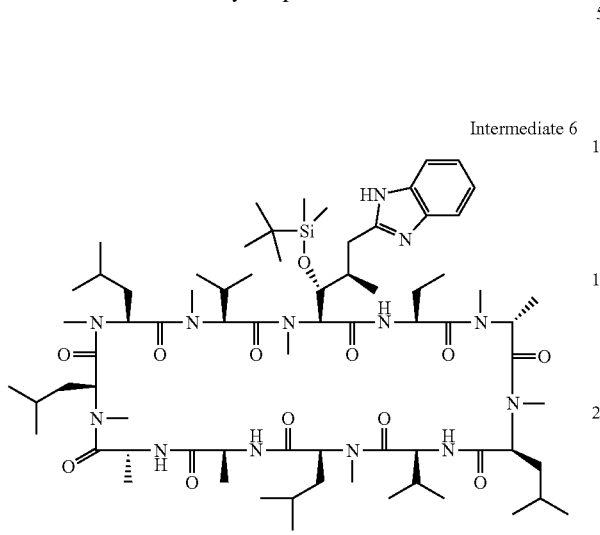

Intermediate 6

Intermediate 4 (198 mg, 0.15 mmol) was dissolved in methanol (1 mL). 1,2-Diaminobenzene (243 mg, 2.25 mmol) was added and the solution was stirred at room temperature for six days. The reaction mixture was concentrated then the residue was partitioned between dichloromethane and 1N aqueous hydrochloric acid. The organic phase was washed with saturated aqueous sodium bicarbonate, dried over sodium sulfate, then concentrated to give crude Intermediate 6, which was used as such in a subsequent deprotection step. ES/MS: 1406.9 MH+.

Intermediate 7: [(2S,3R,4R)-3-(t-Butyldimethylsilanyloxy)-4-methyl-2-(methylamino)-6-oxo-hexanoic acid][1] cyclosporin A

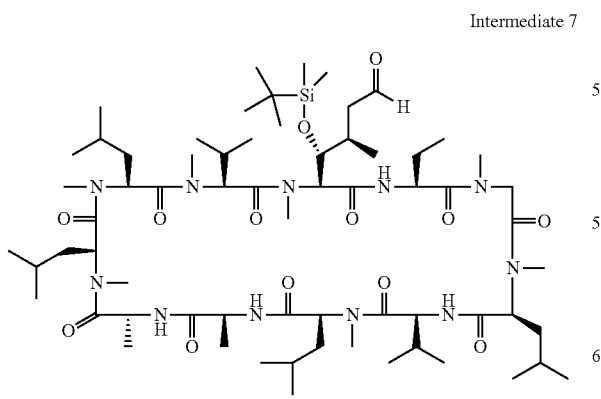

Intermediate 7

Intermediate 7 was prepared from Cyclosporin A in a similar manner as described in the synthesis of Intermediate 2 (reaction with TBDMSOTf) and in the synthesis of Intermediate 3 (reaction with $O_3$).

Intermediate 8: [(2S,3R,4R)-3-(t-Butyldimethylsilanyloxy)-4-methyl-2-(methylamino)-7-(pyridin-3-yl) hept-6-enoic acid][1] [(R)-methyl-Sar][3] cyclosporin A

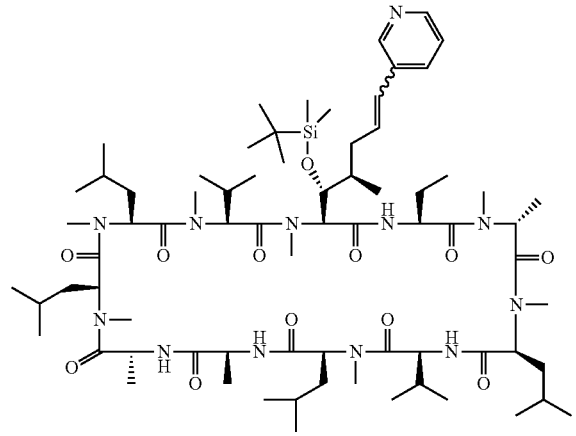

Intermediate 8

A 100 mL three neck flask dried overnight in the oven was equipped with a low temperature thermometer, gas inlet and a septum. Triphenyl (pyridin-3-ylmethyl) phosphonium chloride (650 mg, 1.67 mmol) and dry tetrahydrofuran (9 mL) were introduced in the flask and the suspension was cooled down to −78° C. After drop-wise addition of a 2M solution of sodium bis(trimethylsilyl)amide (730 uL, 1.46 mmol), the cooling bath was replaced with an ice bath. After 30 minutes, a solution of Intermediate 4 (276 mg, 0.208 mmol) in dry tetrahydrofuran (3 mL) was added drop-wise, then the temperature was allowed to increase to room temperature slowly and the suspension was stirred overnight. The reaction mixture was quenched with a saturated aqueous solution of ammonium chloride, then concentrated. The residue was partitioned between ethyl acetate and water. The organic phase was dried over sodium sulfate, then concentrated to give crude Intermediate 8, which was used as such in a subsequent reaction. $^1$H NMR (CDCl$_3$, ppm) δ 6.33 (m, olefin CH).

Intermediate 9: [(2S,3R,4R)-3-Hydroxy-4-methyl-2-(methylamino)-7-(pyridin-3-yl)-hept-6-enoic acid][1] [(R)-methyl-Sar][3] cyclosporin A

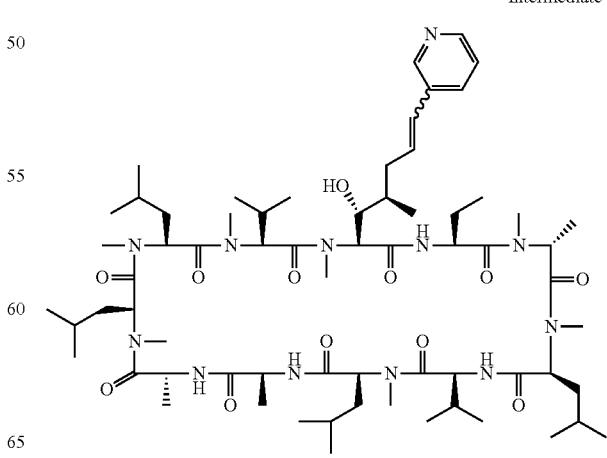

Intermediate 9

Crude Intermediate 8 was dissolved in dry tetrahydrofuran (10 mL) then treated with a 1M solution of tetrabutylammonium fluoride (1.05 mL, 1.05 mmol). The solution was left to stand for four hours. The reaction mixture was concentrated, diluted with dichloromethane, then washed with a saturated aqueous solution of ammonium chloride. The organic phase was dried over sodium sulfate then concentrated. Purification using SCX column eluting with methanol then ammonia in methanol provided Intermediate 9 as a mixture of olefins which was used as such in a subsequent hydrogenation step. ES/MS: 1279.5 MH$^+$; $^1$H NMR (CDCl$_3$, ppm) δ 6.35 (m, olefin CH).

Intermediate 10: [(2S,3R,4R)-3-(t-Butyldimethylsilanyloxy)-6-hydroxy-4-methyl-2-(methylamino)-hexanoic acid]$^1$ [(R)-methyl-Sar]$^3$ cyclosporin A Intermediate 10

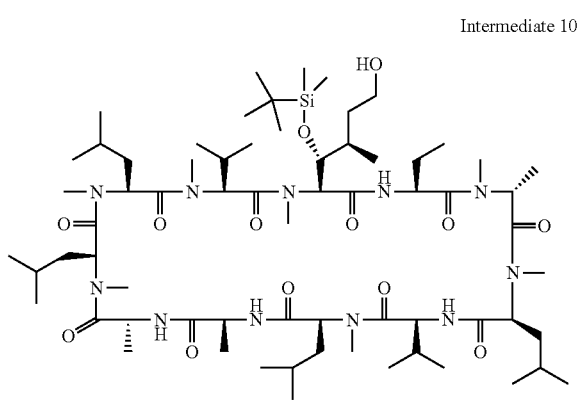 [SMILES: CC[C@H]1NC(=O)[C@@H]([C@H](O[Si](C)(C)C(C)(C)C)[C@H](C)CCO)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

To a suspension of Intermediate 4 (198 mg, 0.15 mmol) in methanol (6 mL) was added sodium borohydride (17 mg, 0.45 mmol) at room temperature. The reaction mixture was stirred for 4 hours, then concentrated. The residue was partitioned between ethyl acetate and water. The organic phase was dried over sodium sulfate, then concentrated to give crude Intermediate 10, which was used as such in a subsequent reaction. $^1$H NMR (CDCl$_3$, ppm) δ 7.60 (d, 1H, amide NH), 7.72 (d, 1H, amide NH), 7.96 (d, 1H, amide NH), 8.41 (d, 1H, amide NH).

Intermediate 11: [(2S,3R,4R)-3,6-Dihydroxy-4-methyl-2-(methylamino)-hexanoic acid]$^1$ [(R)-methyl-Sar]$^3$ cyclosporin A Intermediate 11

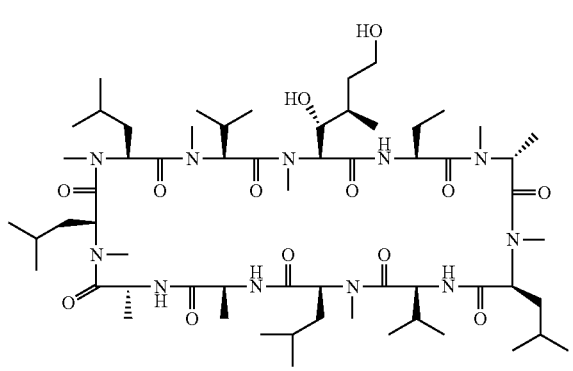

Crude Intermediate 10 was dissolved in dry tetrahydrofuran (7 mL), then treated with a 1M solution of tetrabutylammonium fluoride (0.75 mL, 0.75 mmol). The solution was left to stand for seventeen hours. The reaction mixture was concentrated, then purified using an SCX column eluting with methanol to provide Intermediate 11, which was used as such in a subsequent step. ES/MS: 1206.8 MH$^+$; $^1$H NMR (CDCl$_3$, ppm) δ 7.32 (d, 1H, amide NH), 7.53 (d, 1H, amide NH), 7.88 (d, 1H, amide NH), 8.18 (d, 1H, amide NH).

Intermediate 12: [(R)-methoxy-Sar]$^3$ cyclosporin A

Intermediate 12 is a structural variant of cyclosporin A having an —OCH$_3$ at the position 3 α-carbon (i.e., Formula I, wherein R$^3$ is OCH$_3$). Intermediate 12 was prepared as described in US 2010/0167996.

Intermediate 12 can be used in place of cyclosporin A according to any of the schemes shown herein to produce particular compounds of Formula I wherein R$^3$ is —OCH$_3$.

Intermediate 12

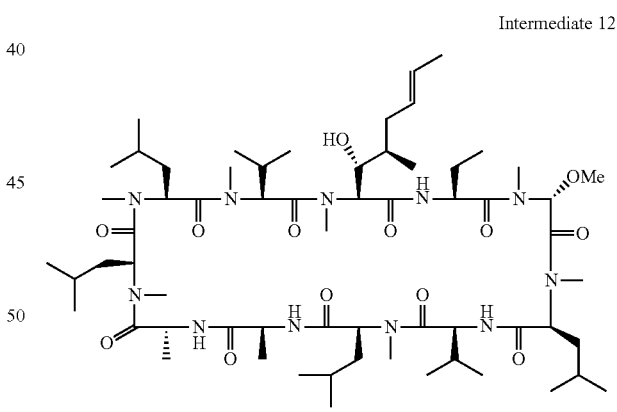

Intermediate 13: [(R)-methoxymethyl-Sar]$^3$ cyclosporin A

Intermediate 13 is a structural variant of cyclosporin A having a —CH$_2$OCH$_3$ at the position 3 α-carbon (i.e., Formula I wherein R$^3$ is OCH$_3$).

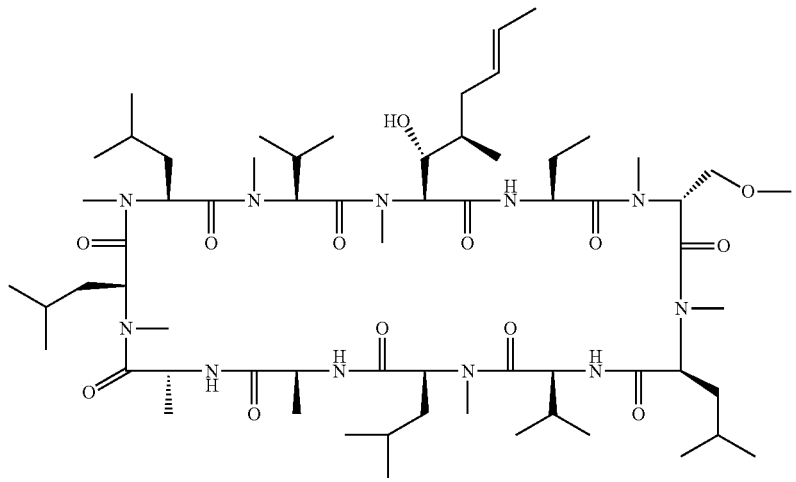

Intermediate 13

[(D)-Serine]³ cyclosporin A was prepared as described by D. Seebach et al. (1993) Helvetica Chimica Acta 73(4): 1564-1590. To [(D)-Serine]³ cyclosporin A (350 mg, 0.28 mmol) dissolved in dichloromethane (3 mL) was added benzyltriethylammonium chloride (65 mg, 0.28 mmol) and aqueous KOH solution (31%, 5.1 mL). Iodomethane (18 µL, 0.28 mmol) was added and the mixture stirred rapidly for 18 hours at room temperature. The reaction mixture was diluted with water (5 mL) and dichloromethane (5 mL) and the layers separated. The aqueous layer was further extracted with dichloromethane (3×10 mL), and the combined organic layers dried (MgSO₄) and evaporated in vacuo. The residue was purified by silica gel chromatography using 6% methanol in dichloromethane to provide Intermediate 13 as an off-white solid.

Intermediate 13 can be used in place of Cyclosporin A according to any of the schemes shown herein to produce particular compounds of Formula I in which $R^3$ is —CH$_2$OCH$_3$. ESMS MH⁺ 1246.87; ¹H NMR (CDCl$_3$, ppm) δ 7.17 (d, 1H, amide NH), 7.44 (d, 1H, amide NH), 7.65 (d, 1H, amide NH), 8.03 (d, 1H, amide NH).

Intermediate 14: [(2S,3R,4R)-3-(Acetoxy)-4-methyl-2(methylamino)-6-oxo-hexanoic acid]¹ [(R)-acetoxymethyl-Sar]³ cyclosporin A

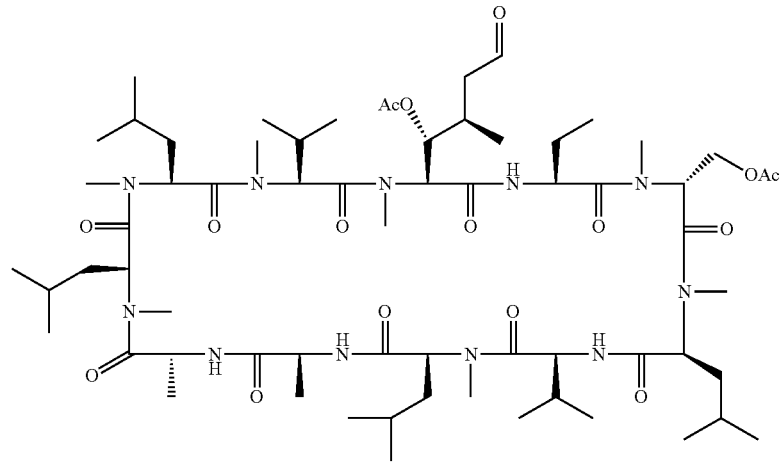

Intermediate 14

Intermediate 14 was prepared from [D-Serine]³ Cyclosporin A as described in U.S. Patent Application Publication US 2006/0069015 A1.

Intermediate 15: [(2S,3R,4R)-3-(Acetoxy)-4-methyl-2-(methylamino)-7-(pyridin-2-yl) hept-6-enoic acid]¹ [(R)-acetoxymethyl-Sar]³ cyclosporin A Intermediate 15

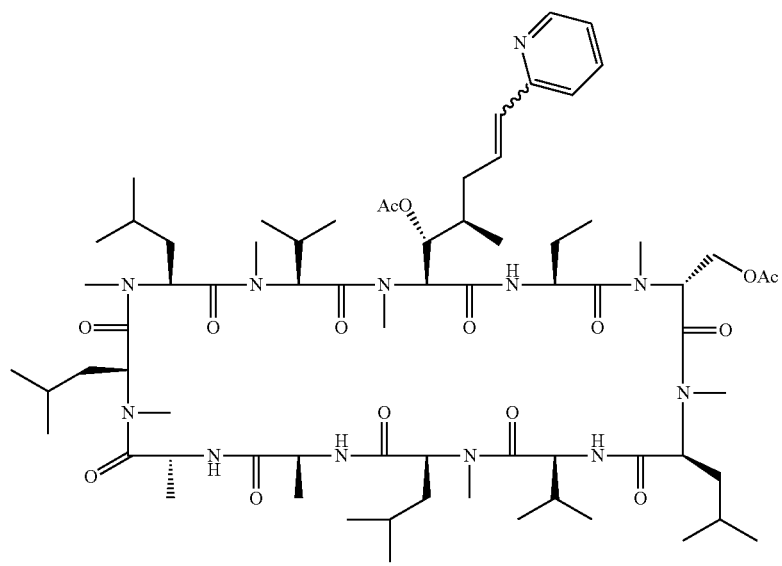

Intermediate 15 was prepared from Intermediate 14 essentially as described for the synthesis for Intermediate 8.

Intermediate 16: [(2S,3R,4R)-3-(Acetoxy)-4-methyl-2-(methylamino)-7-(pyridin-2-yl) heptanoic acid]¹ [(R)-acetoxymethyl-Sar]³ cyclosporin A The crude olefin mixture Intermediate 15 (0.25 mmol) was dissolved in ethyl acetate (25 mL). Under an atmosphere of nitrogen, 10% palladium on carbon (300 mg) was added; then the reaction mixture was hydrogenated. Reaction progress was monitored by NMR (olefin region), and additional catalyst was added until the reaction was complete. The reaction mixture was filtered off through a pad of diatomaceous earth (Celite®) and sodium sulfate under an atmosphere of nitrogen, then concentrated to give the crude product. SCX column chromatography eluting with 100% methanol followed by 0.4M ammonia in methanol provided Intermediate 16. ES/MS: 1381.66 MH⁺; ¹H NMR (CDCl₃, ppm) δ 7.08 (dd, 1H, pyridine CH), 7.22 (d, 1H, amide NH), 7.39 (d, 1H, amide NH), 7.58 (m, 2H, pyridine CH), 8.12 (d, 1H, amide NH), 8.49 (d, 1H, pyridine CH), 8.6 (d, 1H, amide NH).

Intermediate 16

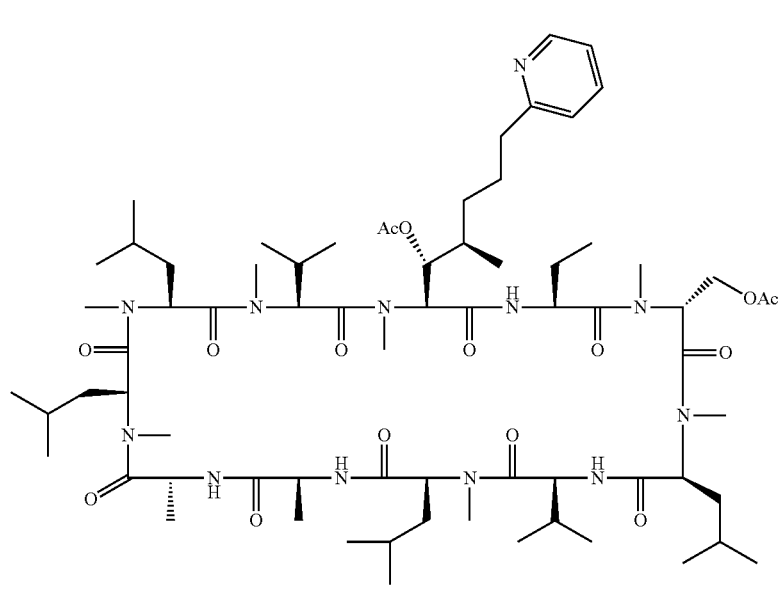

Example Ia—Compounds of the Invention Prepared Via the Imidazole Route

Example 1

Compound 1: [(2S,3R,4R)-3-Hydroxy-4-methyl-2-(methylamino)-5-(1-methyl-1H-imidazol-2-yl)-pentanoic acid]¹ [(R)-methyl-Sar]³ cyclosporin A Compound 1

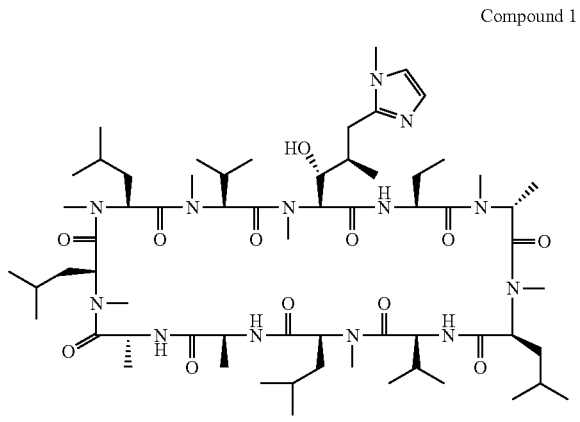 [SMILES: CC[C@H]1NC(=O)[C@@H]([C@H](O)[C@H](C)Cc2nccn2C)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Crude Intermediate 5 (101 mg) was dissolved in dry tetrahydrofuran (1 mL), then treated with a 1M solution of tetrabutylammonium fluoride (0.74 mL, 0.74 mmol). The reaction mixture was allowed to stir at room temperature for 18 hours. The reaction mixture was diluted with water (5 mL) and dichloromethane (5 mL). The layers were separated and the aqueous layer re-extracted with dichloromethane (2×5 mL). The combined organic extracts were dried over magnesium sulfate. Chromatography on silica gel eluting with 0.35M ammonia in methanol:dichloromethane (2:98) provided Compound 1. ES/MS: 1257.0 MH$^+$; $^1$H NMR (CDCl$_3$, ppm) δ 6.77 (m, 1H, imidazole CH), 7.06 (d, 1H, amide NH), 7.39 (m, 1H, imidazole CH), 7.56 (d, 2H, 2 amide NH), 7.94 (d, 1H, amide NH).

Example 2

Compound 2: [(2S,3R,4R)-3-Hydroxy-4-methyl-2-(methylamino)-5-(1-(N-morpholino-ethyl)-1H-imidazol-2-yl)-pentanoic acid]¹ [(R)-methyl-Sar]³ cyclosporin A Compound 2

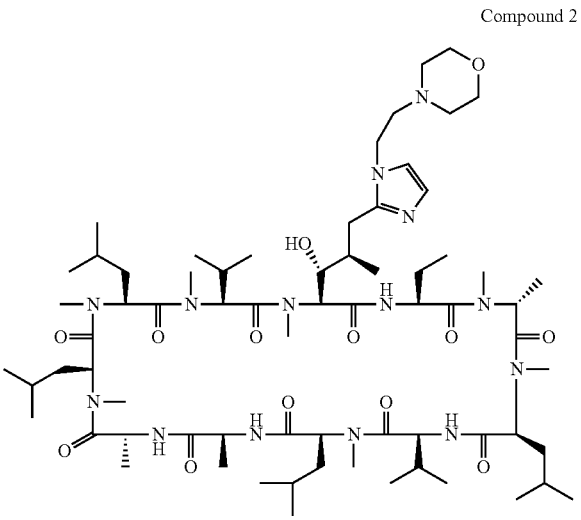 [SMILES: CC[C@H]1NC(=O)[C@@H]([C@H](O)[C@H](C)Cc2nccn2CCN2CCOCC2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 2 was prepared essentially as described for the synthesis of Compound 1. Briefly, Intermediate 4 was reacted with 2-morpholinoethanamine, and the product was deprotected to provide Compound 2. ES/MS: 1355.8 MH$^+$; $^1$H NMR (CDCl$_3$, ppm) δ 6.77 (m, 1H, imidazole CH), 7.06 (d, 1H, amide NH), 7.51-7.64 (m, 3H, imidazole CH and 2 amide NH), 7.96 (d, 1H, amide NH).

Example 3

Compound 3: [(2S,3R,4R)-3-Hydroxy-4-methyl-2-(methylamino)-5-(1-(N-pyrrolidinyl-ethyl)-1H-imidazol-2-yl) pentanoic acid]¹ [(R)-methyl-Sar]³ cyclosporin A Compound 3

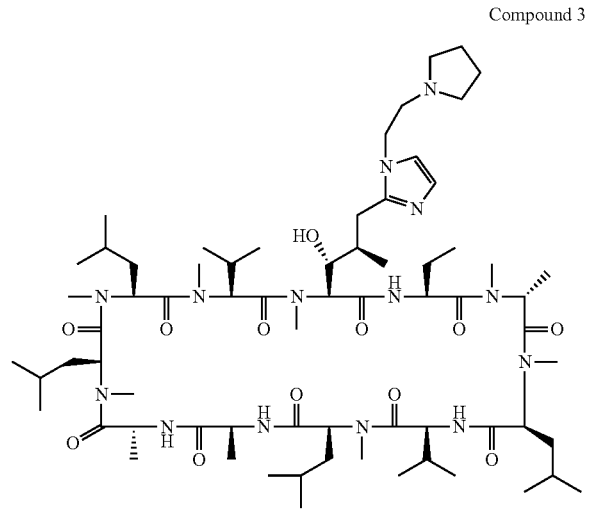 [SMILES: CC[C@H]1NC(=O)[C@@H]([C@H](O)[C@H](C)Cc2nccn2CCN2CCCC2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 3 was prepared essentially as described for the synthesis of Compound 1. Briefly, Intermediate 4 was reacted with 2-pyrrolidin-1-ylethanamine, and the product was deprotected to provide Compound 3. ES/MS: 1339.9 MH$^+$; $^1$H NMR (CDCl$_3$, ppm) δ 6.77 (m, 1H, imidazole CH), 7.06 (d, 1H, amide NH), 7.51-7.57 (m, 2H, imidazole CH and amide NH), 7.59 (d, 1H, amide NH), 7.96 (d, 1H, amide NH).

Example 4

Compound 4: [(2S,3R,4R)-5-(1-(N,N-Dimethyl-ethyl)-1H-imidazol-2-yl)-3-hydroxy-4-methyl-2-(methylamino) pentanoic acid]¹ [(R)-methyl-Sar]³ cyclosporin A Compound 4

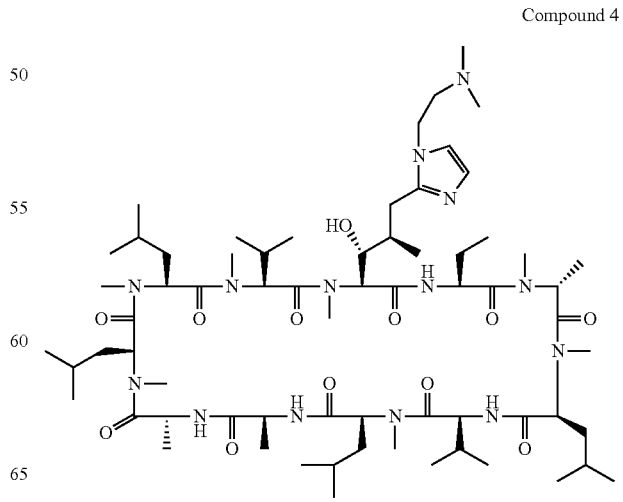

Compound 4 was prepared essentially as described for the synthesis of Compound 1. Briefly, Intermediate 4 was reacted with N',N'-dimethylethane-1,2-diamine, and the product was deprotected to provide Compound 4. ES/MS: 1313.8 MH$^+$; $^1$H NMR (CDCl$_3$, ppm) δ 6.78 (m, 1H, imidazole CH), 7.07 (d, 1H, amide NH), 7.52-7.57 (m, 2H, imidazole CH and amide NH), 7.60 (d, 1H, amide NH), 7.96 (d, 1H, amide NH).

Example 5

Compound 5: [(2S,3R,4R)-3-Hydroxy-4-methyl-2-(methylamino)-5-(1-(pyridin-2-yl-methyl)-1H-imidazol-2-yl)-pentanoic acid]$^1$ [(R)-methyl-Sar]$^3$cyclosporin A

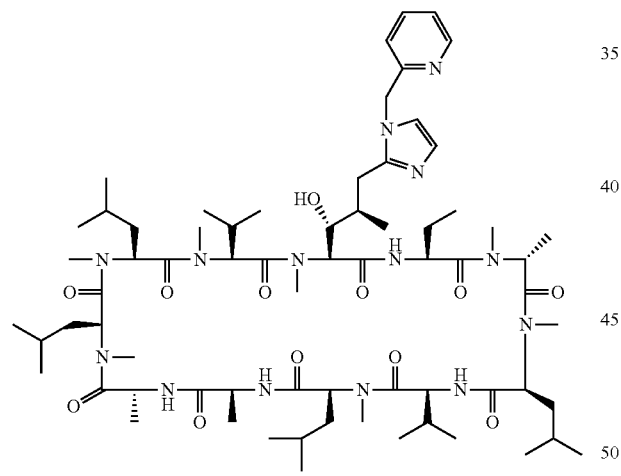

Compound 5

Compound 5 was prepared essentially as described for the synthesis of Compound 1. Briefly, Intermediate 4 was reacted with 2-pyridylmethanamine, and the product was deprotected to provide Compound 5. ES/MS: 1333.7 MH$^+$; $^1$H NMR (CDCl$_3$, ppm) δ 6.81 (d, 1H, pyridyl CH), 6.88 (s, 1H, imidazole CH), 7.07 (d, 1H, amide NH), 7.23 (dd, 1H, pyridyl CH), 7.50-7.53 (m, 2H, imidazole CH and amide NH), 7.61 (d, 1H, amide NH), 7.68 (td, 1H, pyridyl CH), 7.91 (d, 1H, amide NH), 8.58 (d, 1H, pyridyl CH).

Example 6

Compound 6: [(2S,3R,4R)-3-Hydroxy-5-(1-(3-hydroxypropyl)-1H-imidazol-2-yl)-4-methyl-2-(methylamino) pentanoic acid]$^1$ [(R)-methyl-Sar]$^3$ cyclosporin A

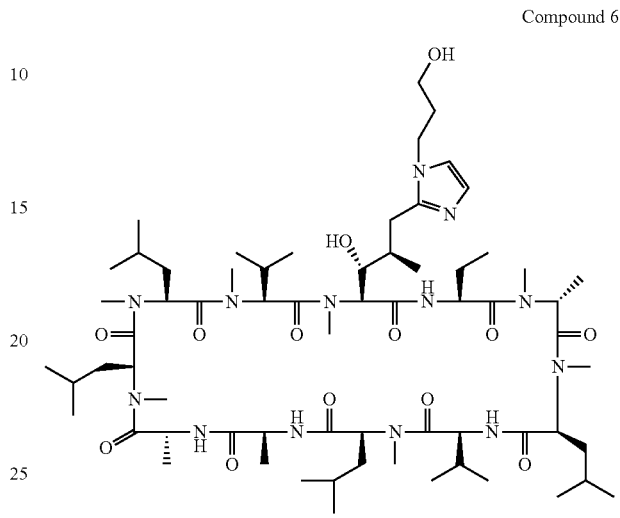

Compound 6

Compound 6 was prepared essentially as described for the synthesis of Compound 1. Briefly, Intermediate 4 was reacted with 3-aminopropan-1-ol, and the product was deprotected to provide Compound 6. ES/MS: 1300.7 MH$^+$; $^1$H NMR (CDCl$_3$, ppm) δ 6.76 (s, 1H, imidazole CH), 7.05 (d, 1H, amide NH), 7.46 (s, 1H, imidazole CH), 7.56 (d, 1H, amide NH), 7.61 (d, 1H, amide NH), 7.96 (d, 1H, amide NH).

Example 7

Compound 7: [(2S,3R,4R)-3-Hydroxy-4-methyl-2-(methylamino) 5-(1-(pyridin-3-yl-ethyl)-1H-imidazol-2-yl) pentanoic acid]$^1$ [(R)-methyl-Sar]$^3$ cyclosporin A

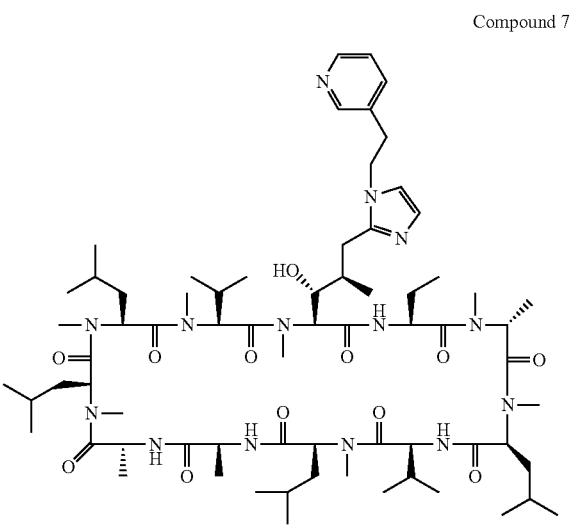 [SMILES: CC[C@H]1NC(=O)[C@@H]([C@H](O)[C@H](C)Cc2nccn2CCc2cccnc2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 7

Compound 7 was prepared essentially as described for the synthesis of Compound 1. Briefly, Intermediate 4 was reacted with 2-(3-pyridyl)ethanamine, and the product was deprotected to provide Compound 7. ES/MS: 1347.6 MH+; $^1$H NMR (CDCl$_3$, ppm) δ 6.77 (s, 1H, imidazole CH), 6.81 (s, 1H, pyridyl CH), 7.06 (d, 1H, amide NH), 7.17-725 (m, 2H, imidazole CH and pyridyl CH), 7.53-7.64 (m, 2H, 2 amide NH), 7.95 (d, 1H, amide NH), 8.46 (d, 1H, pyridyl CH), 8.50 (dd, 1H, pyridyl CH).

Example 8

Compound 8: [(2S,3R,4R)-3-Hydroxy-4-methyl-2-(methylamino)-5-[3-(3,3,3-trifluoro-propyl)-3H-imidazol-2-yl]-pentanoic acid]$^1$ [(R)-methyl-Sar]$^3$ cyclosporin A Compound 8

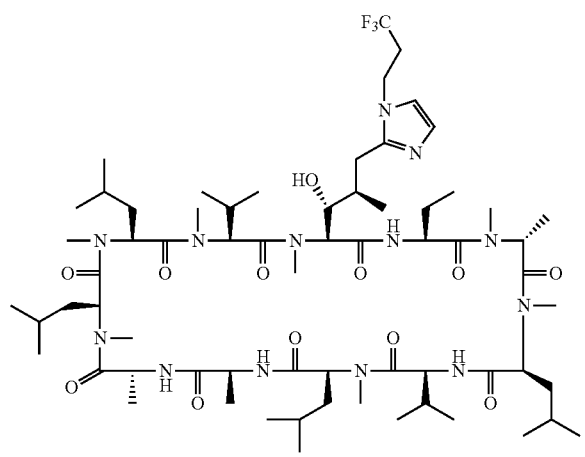

Intermediate 4 was reacted with 3,3,3-trifluoropropan-1-amine, and the product was deprotected to provide Compound 8. ES/MS: 1338.3 MH+; $^1$H NMR (C$_6$D$_6$, ppm) δ 6.81 (s, 1H, imidazole CH), 7.06 (d, 1H, amide NH), 7.47 (s, 1H, imidazole CH), 7.58 (d, 2H, amide NH), 7.92 (d, 1H, amide NH).

Example Ib—Compounds of the Invention Prepared Via the Benzimidazole Route

Example 9

Compound 9: [(2S,3R,4R)-1-(1H-Benzimidazol-2-yl)-3-hydroxy-4-methyl-2-(methylamino)pentanoic acid]$^1$ [(R)-methyl-Sar]$^3$ cyclosporin A Compound 9

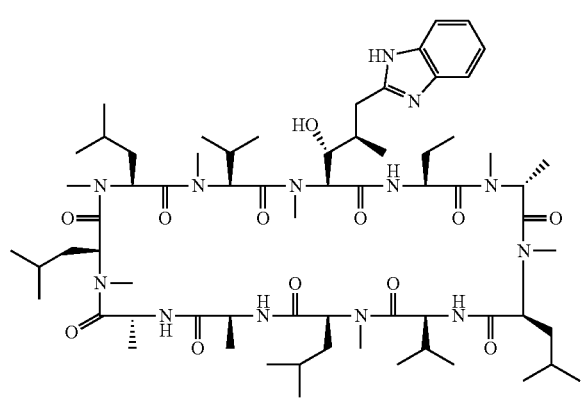

Crude Intermediate 6 (prepared from Intermediate 4) was dissolved in dry tetrahydrofuran (6 mL), then treated with a 1M solution of tetrabutylammonium fluoride (0.75 mL, 0.75 mmol). The solution was left to stand for eighteen hours. The reaction mixture was concentrated, diluted with dichloromethane, then washed with a saturated aqueous solution of ammonium chloride. The organic phase was dried over sodium sulfate, then concentrated. Purification using SCX column chromatography, eluting with methanol then ammonia in methanol, followed by silica gel chromatography using a gradient from 100% dichloromethane to 5% methanol in dichloromethane provided Compound 9. ES/MS: 1292.3 MH+; $^1$H NMR (CDCl$_3$, ppm) δ 7.23 (m, 3H, benzimidazole 2CH and amide NH), 7.44 (m, 1H, benzimidazole CH), 7.62 (m, 1H, benzimidazole CH), 8.04 (d, 1H, amide NH), 8.18 (d, 1H, amide NH), 8.53 (d, 1H, amide NH), 10.1 (s, 1H, benzimidazole NH).

Example 10

Compound 10: [(2S,3R,4R)-1-(1H-Benzimidazol-2-yl)-3-hydroxy-4-methyl-2-(methylamino) pentanoic acid]$^1$ cyclosporin A Compound 10

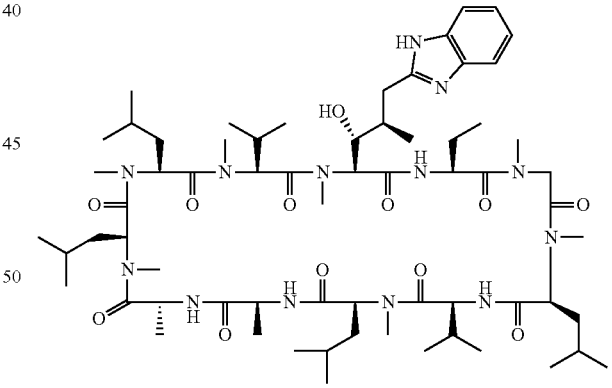

Compound 10 was prepared essentially as described for Compound 9, except that Intermediate 7 was used instead of Intermediate 4. ES/MS: 1278.9 MH+; $^1$H NMR (C$_6$D$_6$, ppm) δ 7.00 (m, 2H, benzimidazole 2CH), 7.27 (d, 1H, benzimidazole CH), 7.61 (d, 1H, benzimidazole CH), 7.76 (d, 1H, amide NH), 8.19 (d, 1H, amide NH), 8.42 (d, 1H, amide NH), 8.78 (d, 1H, amide NH), 10.4 (s, 1H, benzimidazole NH).

Example II—Compounds of the Invention Prepared Via the Wittig Route

Example 11

Compound 11: [(2S,3R,4S)-3-Hydroxy-4-methyl-2-(methylamino)-7-(pyridin-3-yl)-heptanoic acid][1] [(R)-methyl-Sar][3] cyclosporin A

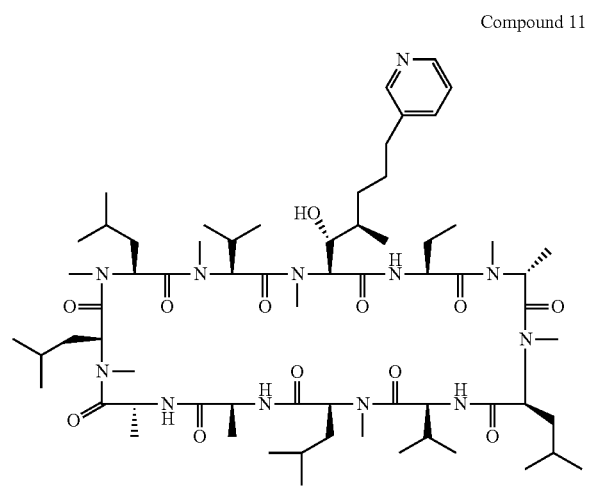 [SMILES: CC[C@H]1NC(=O)[C@@H]([C@H](O)[C@H](C)CCCc2cccnc2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 11

Compound 11 was prepared as outlined in the following scheme. Briefly, crude olefin mixture Intermediate 9 was dissolved in ethyl acetate (40 mL). Under an atmosphere of nitrogen, 10% palladium on carbon (100 mg) was added; then the reaction mixture was hydrogenated. Reaction progress was monitored by NMR (olefin region) and additional catalyst was added until the reaction was complete. The reaction mixture was filtered off through a pad of Celite® and sodium sulfate under an atmosphere of nitrogen, then concentrated to give the crude product. Chromatography column on silica gel using a gradient of 100% dichloromethane to 5% methanol in dichloromethane provided Compound 11. ES/MS: 1281.5 MH$^+$; $^1$H NMR (CDCl$_3$, ppm) δ 7.12 (d, 1H, amide NH), 7.22 (m, 1H, pyridine CH), 7.52 (m, 2H, amide NH and pyridine CH), 7.68 (d, 1H, amide NH), 7.95 (d, 1H, amide NH), 8.45 (bs, 2H, pyridine CH).

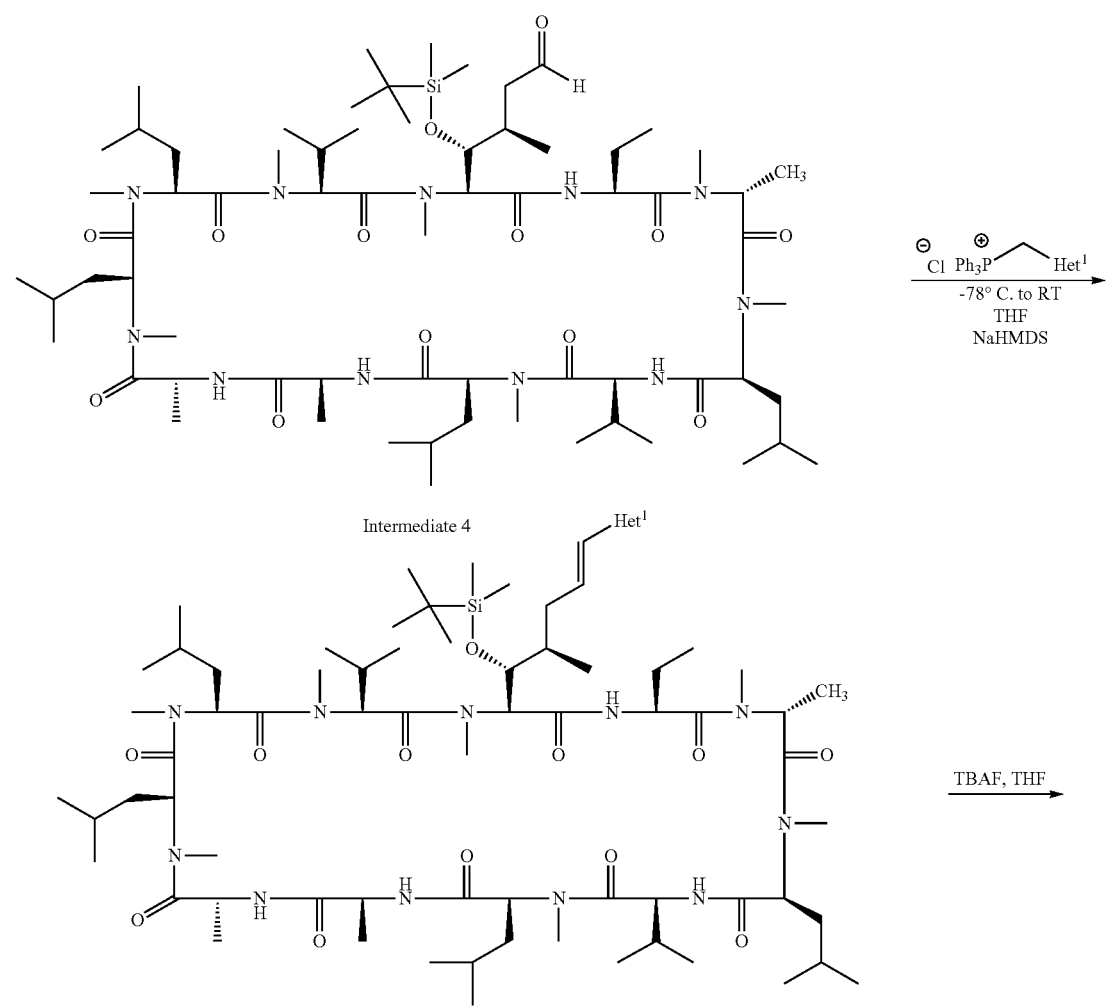

Intermediate 4

Intermediate 8: Het$^1$ is 3-pyridyl

-continued
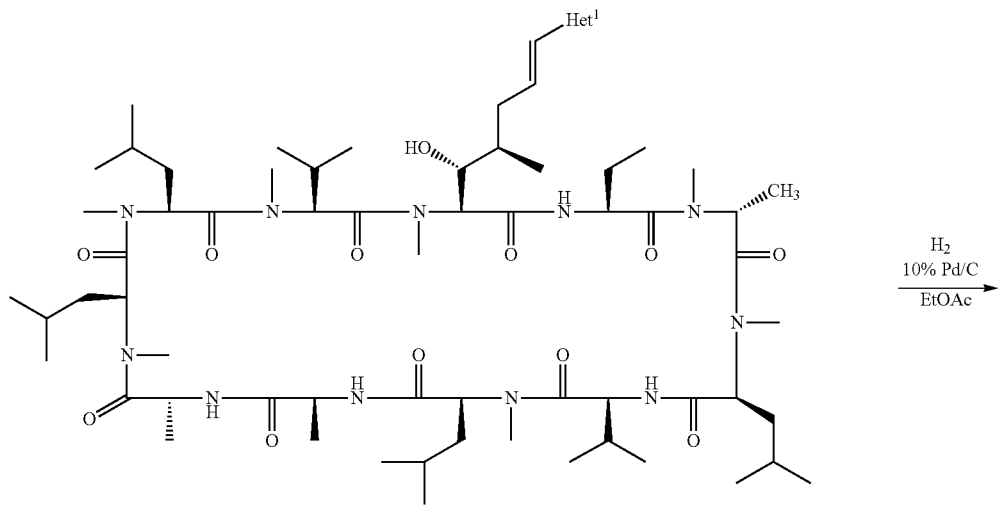
Intermediate 9: Het¹ is 3-pyridyl
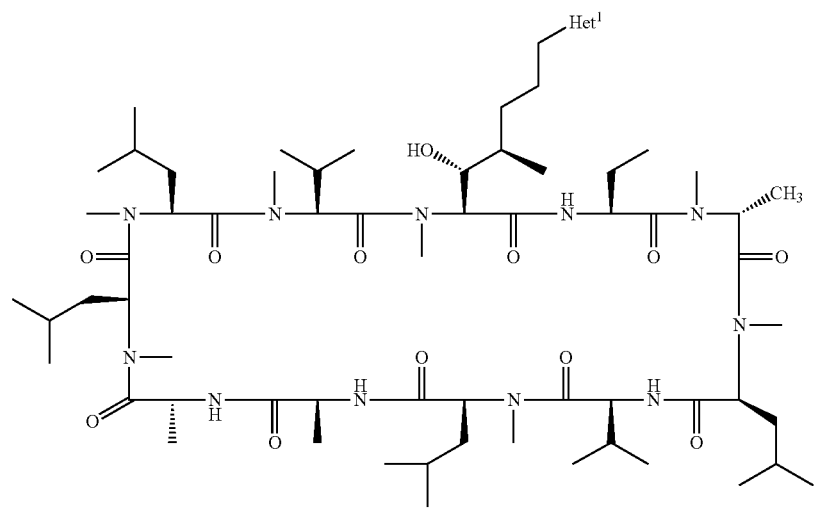
Compound 11 Het¹ is 3-pyridyl

Example 12

Compound 12: [(2S,3R,4R)-3-Hydroxy-4-methyl-2-(methylamino)-7-(pyridin-2-yl)-heptanoic acid][1] [(R)-methyl-Sar][3] cyclosporin A Compound 12

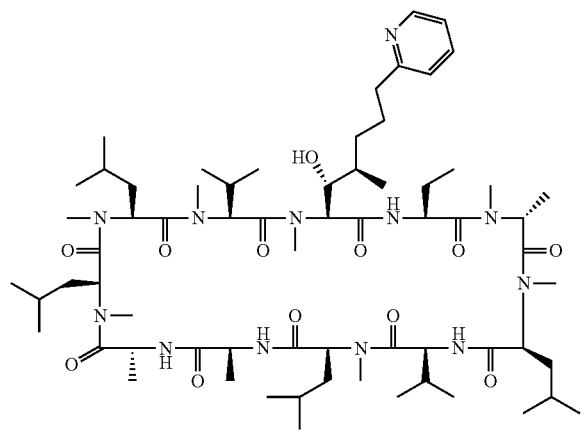

Compound 12 was prepared from Intermediate 4 using (2-pyridinylmethyl)triphenylphosphonium chloride as the Wittig reagent, followed by hydrogenation using 10% palladium on carbon, as described for Compound 11. ES/MS: 1281.7 MH+; $^1$H NMR (CDCl$_3$, ppm) δ 7.12 (m, 3H, amide NH & pyridine 2CH), 7.50 (d, 1H, amide NH), 7.59 (td, 1H, pyridine CH), 7.70 (d, 1H, amide NH), 7.98 (d, 1H, amide NH), 8.52 (d, 1H, pyridine CH).

Example 13

Compound 13: [(2S,3R,4R)-3-Hydroxy-4-methyl-2-(methylamino)-7-(2-methyl-thiazol-4-yl)-heptanoic acid][1] [(R)-methyl-Sar][3] cyclosporin A Compound 13

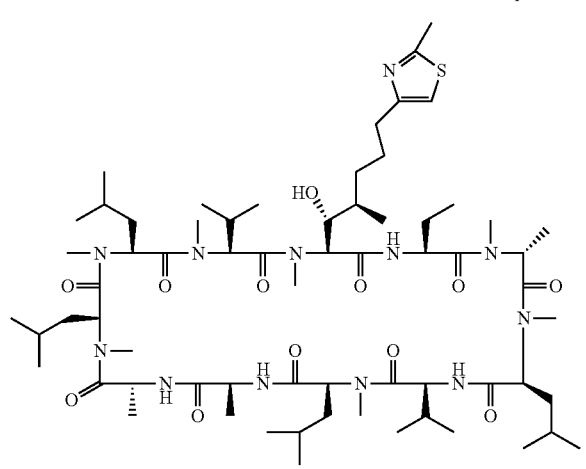

Compound 13 was prepared from Intermediate 4 using (2-methylthiazol-4-yl)methyl triphenylphosphonium chloride as the Wittig reagent, followed by hydrogenation using 10% palladium on carbon as described above. ES/MS: 1301.6 MH+; $^1$H NMR (CDCl$_3$, ppm) δ 6.74 (s, 1H, thiazole CH), 7.13 (d, 1H, amide NH), 7.50 (d, 1H, amide NH), 7.70 (d, 1H, amide NH), 7.99 (d, 1H, amide NH).

Example 14

Compound 14: [(2S,3R,4R)-7-(5-Fluoro-pyridin-2-yl)-3-hydroxy-4-methyl-2-(methylamino)-heptanoic acid][1] [(R)-methyl-Sar][3] cyclosporin A Compound 14

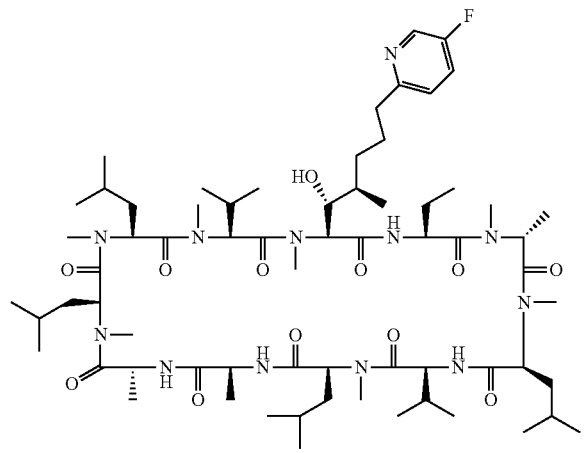

Compound 14 was prepared from Intermediate 4 using (5-fluoro-2-pyridinylmethyl)triphenylphosphonium chloride as the Wittig reagent, followed by hydrogenation using 10% palladium on carbon as described above. ES/MS: 1299.6 MH+; $^1$H NMR (CDCl$_3$, ppm) δ 7.12 (m, 2H, amide NH & pyridine 1CH), 7.30 (m, 1H, pyridine CH), 7.50 (d, 1H, amide NH), 7.69 (d, 1H, amide NH), 7.97 (d, 1H, amide NH), 8.38 (m, 1H, pyridine CH).

Example 15

Compound 15: [(2S,3R,4R)-3-Hydroxy-4-methyl-2-(methylamino)-7-(pyridin-4-yl)-heptanoic acid][1] [(R)-methyl-Sar][3] cyclosporin A Compound 15

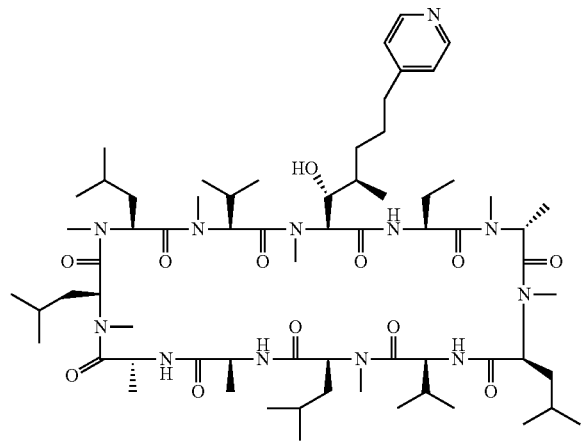

Compound 15 was prepared from Intermediate 4 using (4-pyridinylmethyl)triphenylphosphonium chloride as the Wittig reagent, followed by hydrogenation using 10% palladium on carbon as described above. ES/MS: 1281.6 MH+; $^1$H NMR (CDCl3, ppm) δ 7.11 (m, 3H, amide NH & pyridine 2CH), 7.53 (d, 1H, amide NH), 7.68 (d, 1H, amide NH), 7.96 (d, 1H, amide NH), 8.49 (d, 2H, pyridine CH).

Example 16

Compound 16: [(2S,3R,4R)-3-Hydroxy-4-methyl-2-(methylamino)-7-(5-methoxy-pyridin-2-yl)-heptanoic acid][1] [(R)-methyl-Sar][3] cyclosporin A Compound 16

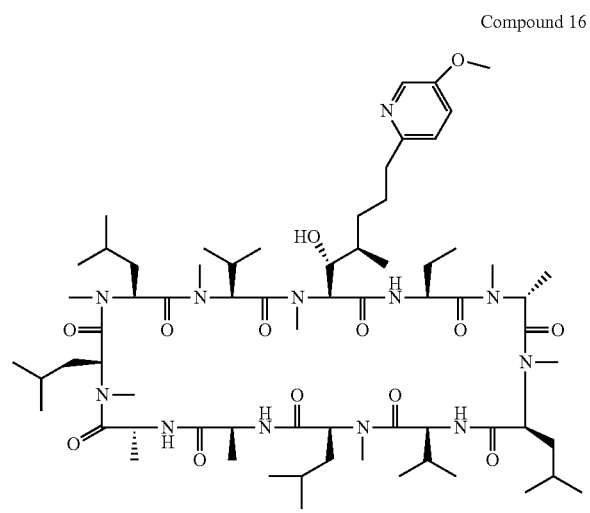 [SMILES: CC[C@H]1NC(=O)[C@@H]([C@H](O)[C@H](C)CCCc2ccc(OC)cn2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 16 was prepared from Intermediate 4 using (5-methoxy-2-pyridinylmethyl)triphenylphosphonium chloride as the Wittig reagent, followed by hydrogenation using 10% palladium on carbon as described above. ES/MS: 1311.2 MH+; $^1$H NMR (CDCl3, ppm) δ 7.10 (m, 3H, amide NH & pyridine 2CH), 7.49 (d, 1H, amide NH), 7.69 (d, 1H, amide NH), 7.98 (d, 1H, amide NH), 8.22 (d, 1H, pyridine CH).

Example 17

Compound 17: [(2S,3R,4R)-3-Hydroxy-4-methyl-2-(methylamino)-7-(2-methyl-pyridin-4-yl)-heptanoic acid][1] [(R)-methyl-Sar][3] cyclosporin A Compound 17

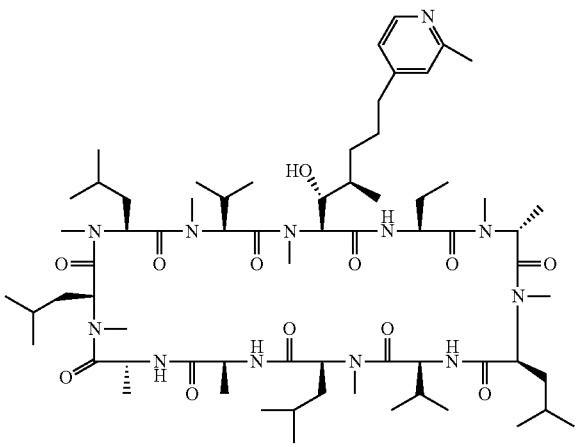

Compound 17 was prepared from Intermediate 4 using (2-methyl-4-pyridinylmethyl)triphenylphosphonium chloride as the Wittig reagent, followed by hydrogenation using 10% palladium on carbon as described above. ES/MS: 1295.9 MH+; $^1$H NMR (CDCl3, ppm) δ 6.91 (d, 1H, pyridine 1CH), 6.98 (s, 1H, pyridine 1CH), 7.13 (d, 1H, amide NH), 7.53 (d, 1H, amide NH), 7.68 (d, 1H, amide NH), 7.95 (d, 1H, amide NH), 8.35 (d, 1H, pyridine CH).

Example 18

Compound 18: [(2S,3R,4R)-3-Hydroxy-4-methyl-2-(methylamino)-7-(pyrazin-2-yl)-heptanoic acid][1] [(R)-methyl-Sar][3] cyclosporin A Compound 18

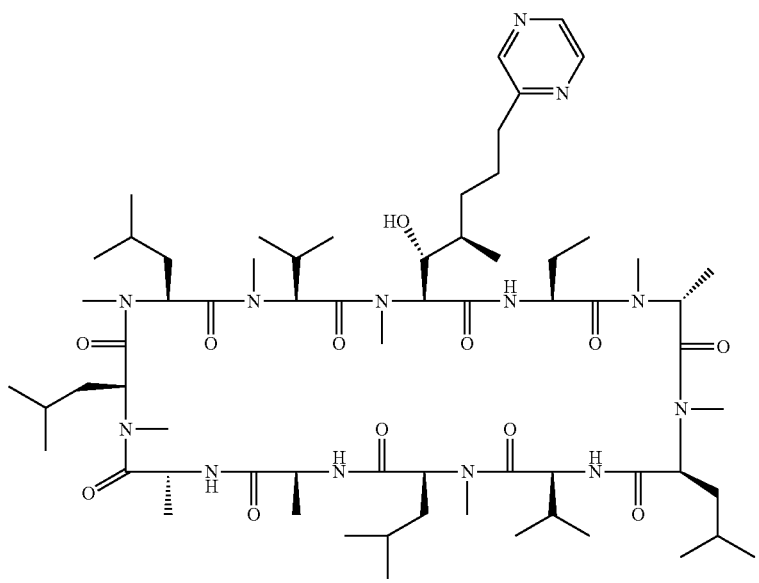

Compound 18 was prepared from Intermediate 4 using (2-pyrazinylmethyl)triphenylphosphonium chloride as the Wittig reagent, followed by hydrogenation using 10% palladium on carbon as described above. ES/MS: 1282.34 MH$^+$; $^1$H NMR (CDCl$_3$, ppm) δ 7.13 (d, 1H, amide NH), 7.50 (d, 1H, amide NH), 7.68 (d, 1H, amide NH), 7.98 (d, 1H, amide NH), 8.38 (m, 1H, pyrazine CH), 8.46 (m, 2H, pyrazine CH).

Example 19

Compound 19: [(2S,3R,4R)-3-Hydroxy-4-methyl-2-(methylamino) tetrahydro-imidazo[1,2-a]pyridin-2-yl)-heptanoic acid]$^1$ [(R)-methyl-Sar]$^3$ cyclosporin A Compound 19 was prepared from Intermediate 4 using 2-((triphenylphosphoranyl)methyl)imidazo[1,2-a]pyridine chloride as the Wittig reagent, followed by hydrogenation using 10% palladium on carbon as described above. ES/MS: 1325.27 MH$^{+1}$H NMR (CDCl$_3$, ppm) δ 6.49 (s, 1H, imidazo CH), 7.13 (d, 1H, amide NH), 7.47 (d, 1H, amide NH), 7.69 (d, 1H, amide NH), 7.97 (d, 1H, amide NH).

Example 20

Compound 20: [(2S,3R,4R)-3-Hydroxy-7-(1-methyl-1H-imidazol-4-yl)-4-methyl-2-(methylamino) heptanoic acid]$^1$ [(R)-methyl-Sar]$^3$ cyclosporin A

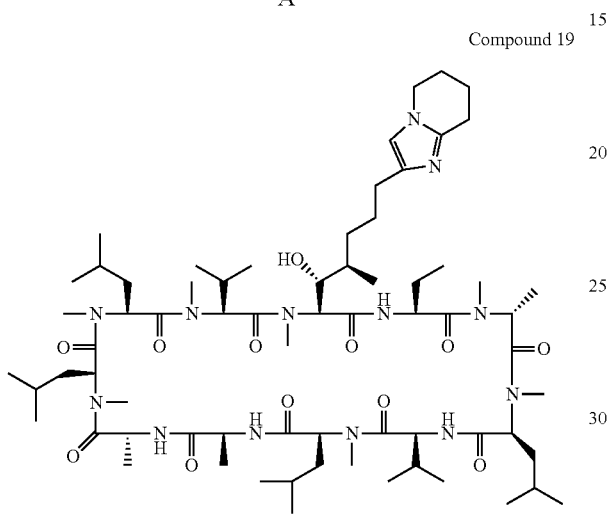

Compound 19

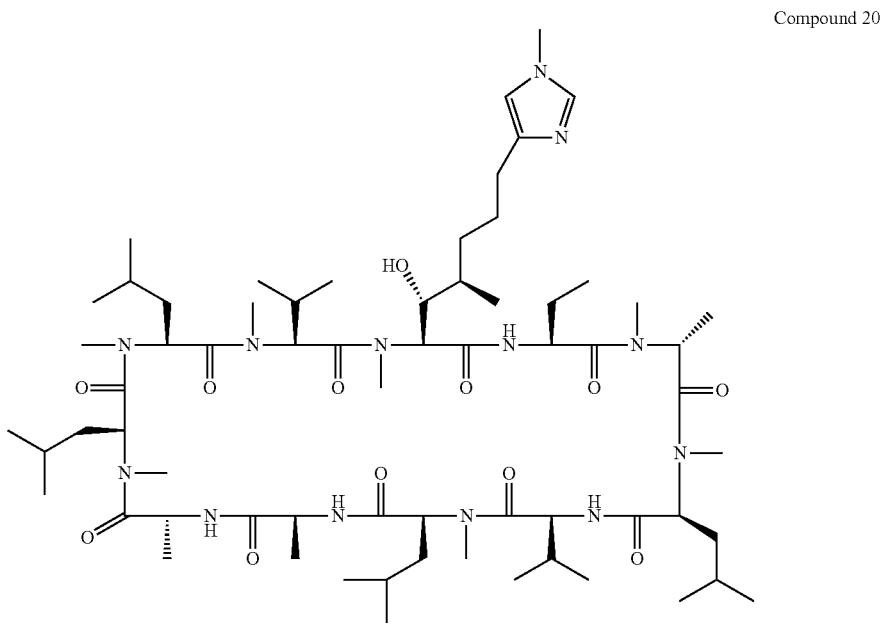 [SMILES: CC[C@H]1NC(=O)[C@@H]([C@H](O)[C@H](C)CCCc2cn(C)cn2)N(C)C(=O)[C@@H](C(C)C)N(C)C(=O)[C@@H](CC(C)C)N(C)C(=O)[C@@H](CC(C)C)N(C)C(=O)[C@H](C)NC(=O)[C@@H](C)NC(=O)[C@@H](CC(C)C)N(C)C(=O)[C@@H](C(C)C)NC(=O)[C@H](CC(C)C)N(C)C(=O)[C@@H](C)N(C)C1=O]

Compound 20

Compound 20 was prepared from Intermediate 4 using (1-methyl-1H-imidazol-4-yl)methyl triphenylphosphonium chloride as the Wittig reagent, followed by hydrogenation using 10% palladium on carbon as described above. ES/MS: 1284.86 MH+; $^1$H NMR (CDCl$_3$, ppm) δ 6.59 (s, 1H, imidazole CH), 7.14 (d, 1H, amide NH), 7.31 (s, 1H, imidazole CH), 7.48 (d, 1H, amide NH), 7.70 (d, 1H, amide NH), 7.98 (d, 1H, amide NH).

Example 21

Compound 21: [(2S,3R,4R)-3-Hydroxy-4-methyl-2-(methylamino)-7-(pyridazin-3-yl)-heptanoic acid][1] [(R)-methyl-Sar][3] cyclosporin A Compound 21

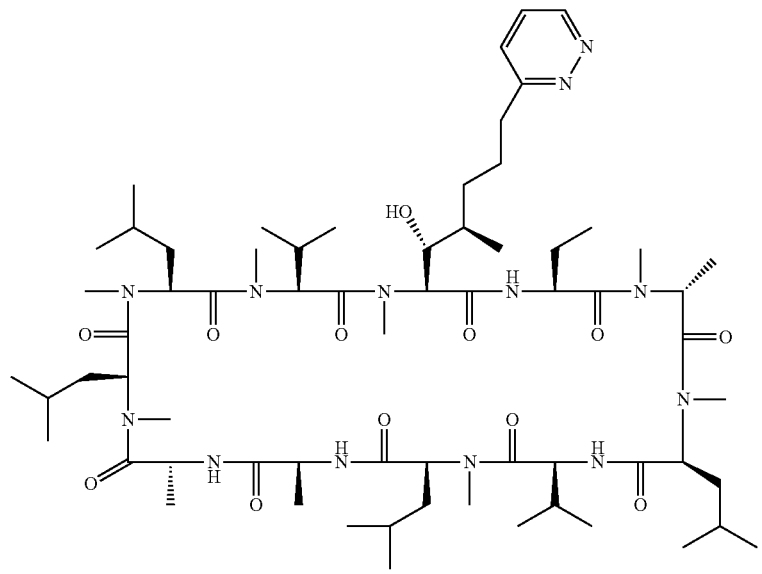

Compound 21 was prepared from Intermediate 4 using (3-pyridazinylmethyl)triphenylphosphonium chloride as the Wittig reagent, followed by hydrogenation using 10% palladium on carbon as described above. ES/MS: 1282.71 MH+; $^1$H NMR (CDCl$_3$, ppm) δ 7.14 (d, 1H, amide NH), 7.36 (m, 2H, pyridazine CH), 7.52 (d, 1H, amide NH), 7.70 (d, 1H, amide NH), 8.00 (d, 1H, amide NH), 9.04 (s, 1H, pyridazine CH).

Example 22

Compound 22: [(2S,3R,4R)-3-Hydroxy-4-methyl-2-(methylamino)-7-(pyrimidin-2-yl)-heptanoic acid][1] [(R)-methyl-Sar][3] cyclosporin A Compound 22

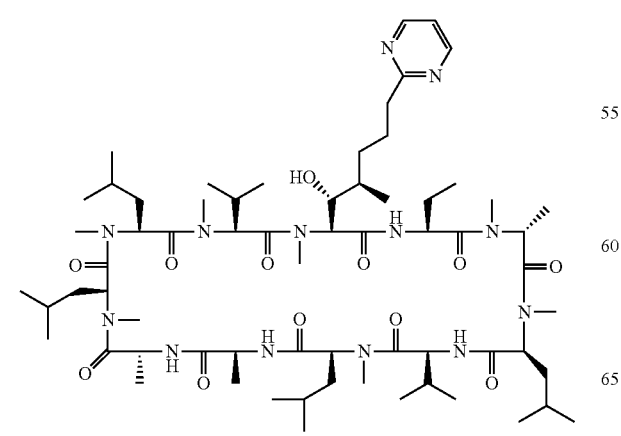

Compound 22 was prepared from Intermediate 4 using (2-pyrimidinylmethyl)triphenylphosphonium chloride as the Wittig reagent, followed by hydrogenation using 10% palladium on carbon as described above. ESMS MH+1282.53; $^1$H NMR (CDCl$_3$, ppm) δ 7.10 (t, 1H, Ar—H), 7.15 (d, 1H, amide NH), 7.45 (d, 1H, amide NH), 7.71 (d, 1H, amide NH), 8.00 (d, 1H, amide NH), 8.66 (d, 2H, Ar—H).

Example 23

Compound 23: [(2S,3R,4R)-3-Hydroxy-4-methyl-2-(methylamino)-7-(2-methylpyrazol-3-yl)-heptanoic acid]$^1$ [(R)-methyl-Sar]$^3$ cyclosporin A Compound 23

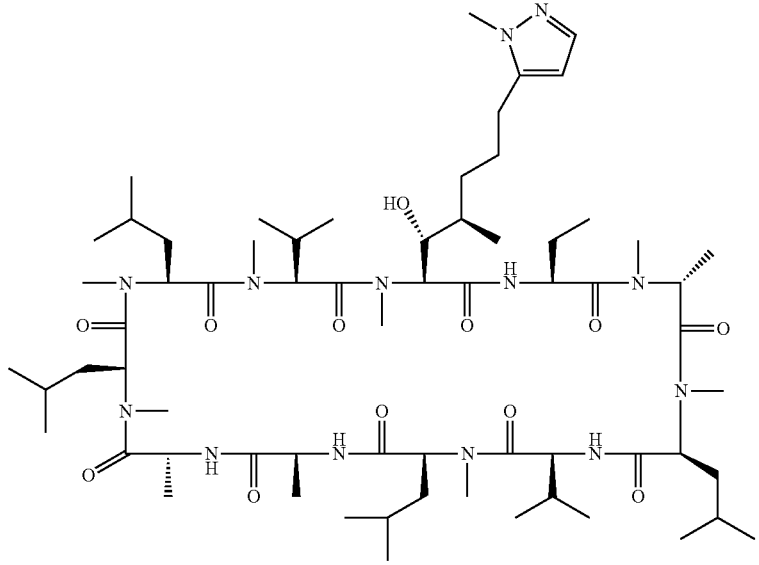

Compound 23 was prepared from Intermediate 4 using (2-methylpyrazol-3-yl)methyl triphenylphosphonium chloride as the Wittig reagent, followed by hydrogenation using 10% palladium on carbon as described above. ES/MS: 1284.66 MH+; $^1$H NMR (CDCl$_3$, ppm) δ 6.01 (d, 1H, pyrazole CH), 7.13 (d, 1H, amide NH), 7.36 (d, 1H, pyrazole CH), 7.54 (d, 1H, amide NH), 7.68 (d, 1H, amide NH), 7.98 (d, 1H, amide NH).

Example 24

Compound 24: [(2S,3R,4R)-3-Hydroxy-4-methyl-2-(methylamino)-7-(oxazolin-2-yl)-heptanoic acid]$^1$ cyclosporin A Compound 24

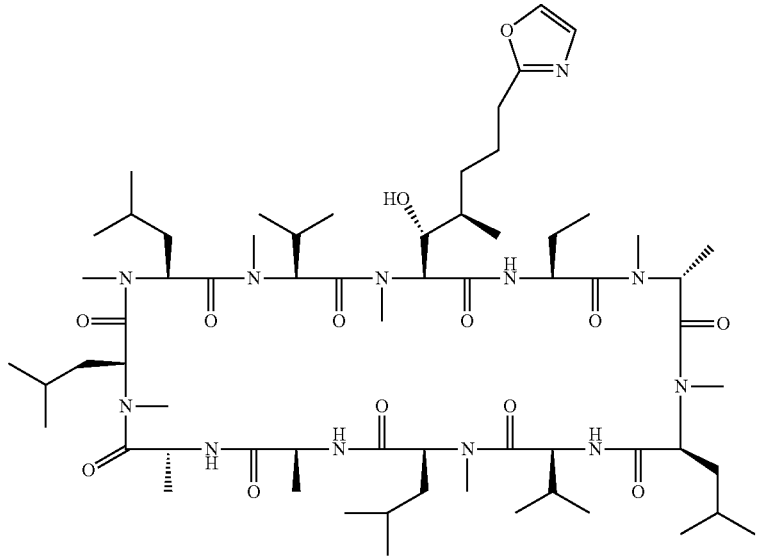

Compound 24 was prepared from Intermediate 4 using (2-oxazolinylmethyl)triphenylphosphonium chloride as the Wittig reagent, followed by hydrogenation using 10% palladium on carbon as described above. ESMS MH+ 1271.75; $^1$H NMR (CDCl$_3$, ppm) δ 7.01 (s, 1H, oxazole CH), 7.16 (d, 1H, amide NH), 7.49 (d, 1H, amide NH), 7.56 (s, 1H, oxazole CH), 7.72 (d, 1H, amide NH), 8.00 (d, 1H, amide NH).

Example 25

Compound 25: [(2S,3R,4R)-3-Hydroxy-4-methyl-2-(methylamino)-7-(1-methylpyrazol-3-yl) heptanoic acid]$^1$ [(R)-methyl-Sar]$^3$ cyclosporin A Compound 25

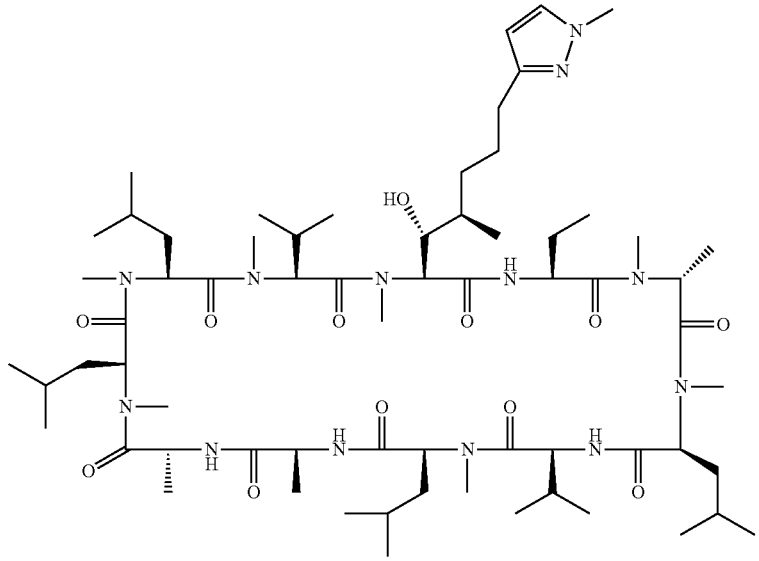

Compound 25 was prepared from Intermediate 4 using (1-methylpyrazol-3-yl)methyl triphenylphosphonium chloride as the Wittig reagent, followed by hydrogenation using 10% palladium on carbon as described above. ES/MS: 1284.72 MH+; $^1$H NMR (CDCl$_3$, ppm) δ 6.01 (d, 1H, pyrazole CH), 7.12 (d, 1H, amide NH), 7.21 (d, 1H, pyrazole CH), 7.48 (d, 1H, amide NH), 7.70 (d, 1H, amide NH), 7.97 (d, 1H, amide NH).

Example 26

Compound 26: [(2S,3R,4R)-3-Hydroxy-7-(1-methyl-1H-imidazol-2-yl)-4-methyl-2-(methylamino) heptanoic acid]$^1$ [(R)-methyl-Sar]$^3$ cyclosporin A Compound 26

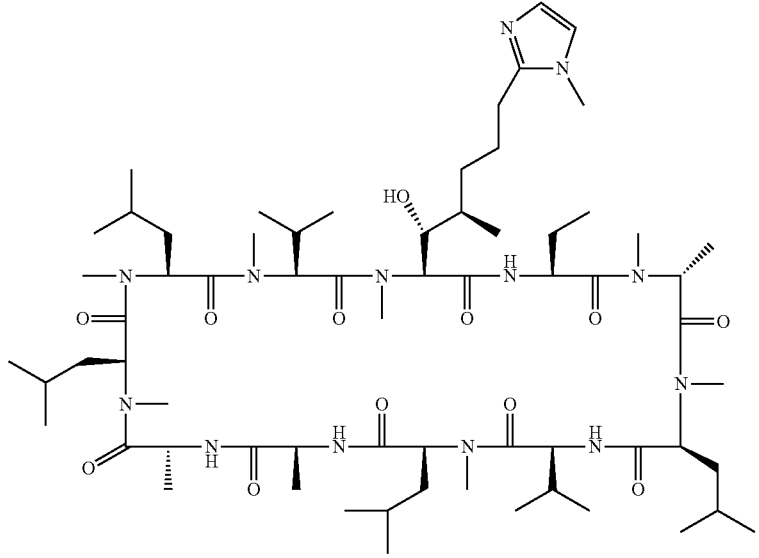

Compound 26 was prepared from Intermediate 4 using (1-methyl-1H-imidazol-2-yl)methyl triphenylphosphonium chloride as the Wittig reagent, followed by hydrogenation using 10% palladium on carbon as described above. ES/MS: 1284.4 MH$^+$; $^1$H NMR (CDCl$_3$, ppm) δ 6.71 (d, 1H, imidazole CH), 6.84 (d, 1H, imidazole CH), 7.10 (s, 1H, amide NH), 7.45 (d, 1H, amide NH), 7.71 (d, 1H, amide NH), 7.96 (d, 1H, amide NH).

Example 27

Compound 27: [(2S,3R,4R)-3-Hydroxy-4-methyl-2-(methylamino)-7-(1-methylpyrazol-4-yl)-heptanoic acid]$^1$ [(R)-methyl-Sar]$^3$ cyclosporin A Compound 27

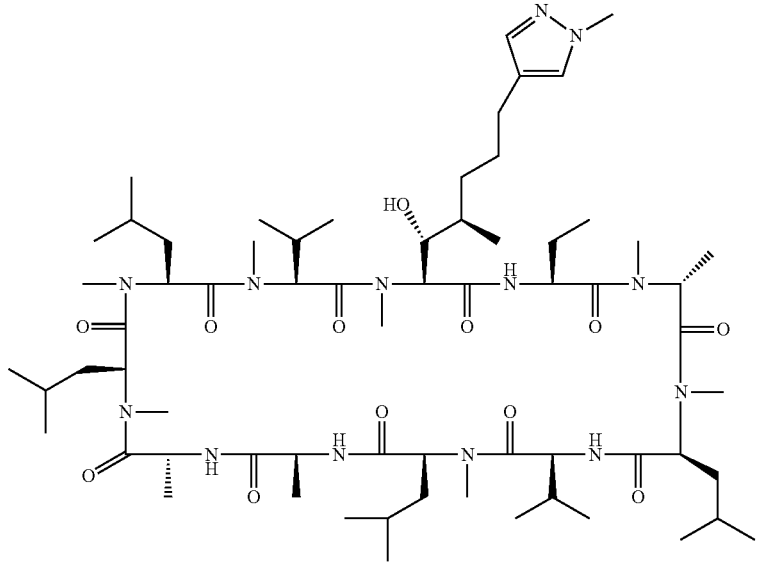

Compound 27 was prepared from Intermediate 4 using (1-methylpyrazol-4-yl)methyl triphenylphosphonium chloride as the Wittig reagent, followed by hydrogenation using 10% palladium on carbon as described above. ES/MS: 1284.5 MH$^+$; $^1$HNMR (CDCl$_3$, ppm) δ 7.14 (m, 2H, amide NH and pyrazole CH), 7.26 (m, 1H, pyrazole CH), 7.50 (d, 1H, amide NH), 7.68 (d, 1H, amide NH), 7.95 (d, 1H, amide NH).

Example 28

Compound 28: [(2S,3R,4R)-3-Hydroxy-4-methyl-2-(methylamino)-8-(pyridin-2-yl)-octanoic acid]$^1$ [(R)-methyl-Sar]$^3$ cyclosporin A Compound 28

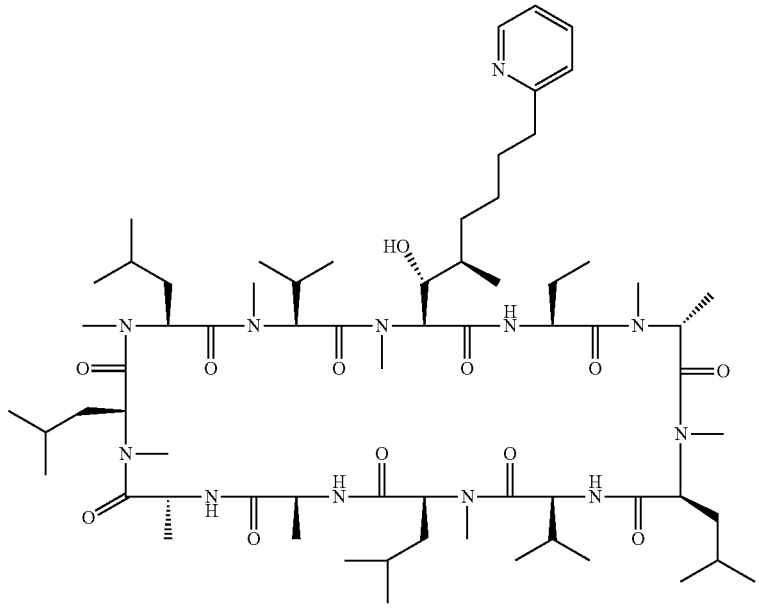

Compound 28 was prepared from Intermediate 4 using 2-(pyridin-2-yl)ethyltriphenylphosphonium iodide as the Wittig reagent, followed by hydrogenation using 10% palladium on carbon as described above. ES/MS: 1295.7 MH+; ¹HNMR (CDCl₃, ppm) δ 7.13 (m, 3H, amide NH & pyridine 2CH), 7.50 (d, 1H, amide NH), 7.60 (td, 1H, pyridine CH), 7.66 (d, 1H, amide NH), 7.93 (d, 1H, amide NH), 8.52 (d, 1H, pyridine CH).

Example 29

Compound 29: [(2S,3R,4R)-3-Hydroxy-4-methyl-2-(methylamino)-7-(pyridine-2-yl)-heptanoic acid]¹ cyclosporin A Compound 29

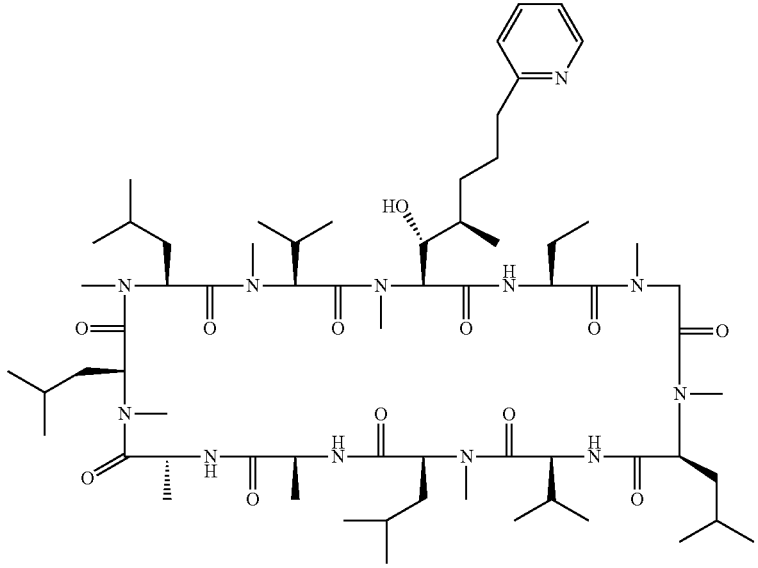

Compound 29 was prepared from Intermediate 7 using (2-pyridinylmethyl)triphenylphosphonium chloride as the Wittig reagent, followed by hydrogenation using 10% palladium on carbon as described above. ES/MS: 1267.5 MH+; ¹H NMR (CDCl₃, ppm) δ 7.12 (m, 3H, amide NH & pyridine 2CH), 7.48 (d, 1H, amide NH), 7.58 (td, 1H, pyridine CH), 7.69 (d, 1H, amide NH), 8.01 (d, 1H, amide NH), 8.51 (d, 1H, pyridine CH).

Example 30

Compound 30: [(2S,3R,4R)-3-Hydroxy-4-methyl-2-(methylamino)-7-(pyridin-4-yl)-heptanoic acid]¹ cyclosporin A Compound 30

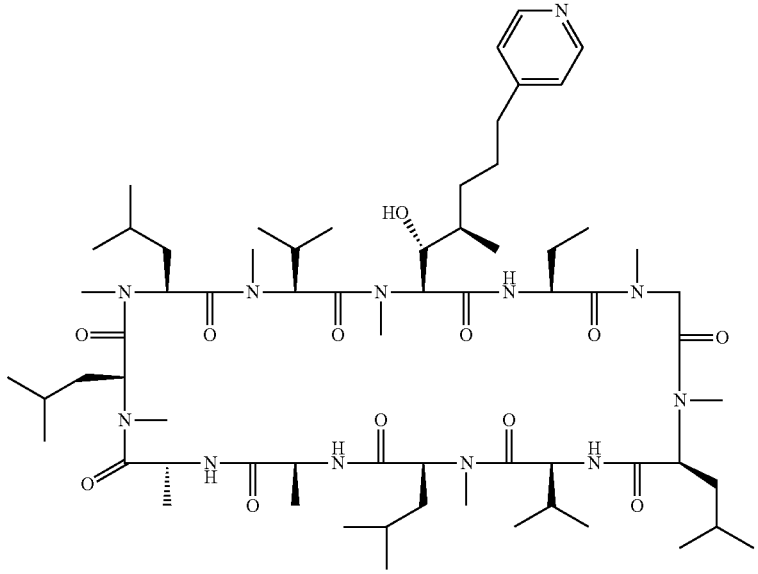

Compound 30 was prepared from Intermediate 7 using (4-pyridinylmethyl)triphenylphosphonium chloride as the Wittig reagent, followed by hydrogenation using 10% palladium on carbon as described above. ES/MS: 1267.5 MH+; ¹H NMR (CDCl₃, ppm) δ 7.13 (m, 3H, amide NH & pyridine 2CH), 7.53 (d, 1H, amide NH), 7.68 (d, 1H, amide NH), 8.00 (d, 1H, amide NH), 8.48 (bs, 2H, pyridine 2CH).

Example 31

Compound 31: [(2S,3R,4R)-3-Hydroxy-4-methyl-2-(methylamino)-7-(pyridin-3-yl)-heptanoic acid]¹ cyclosporin A

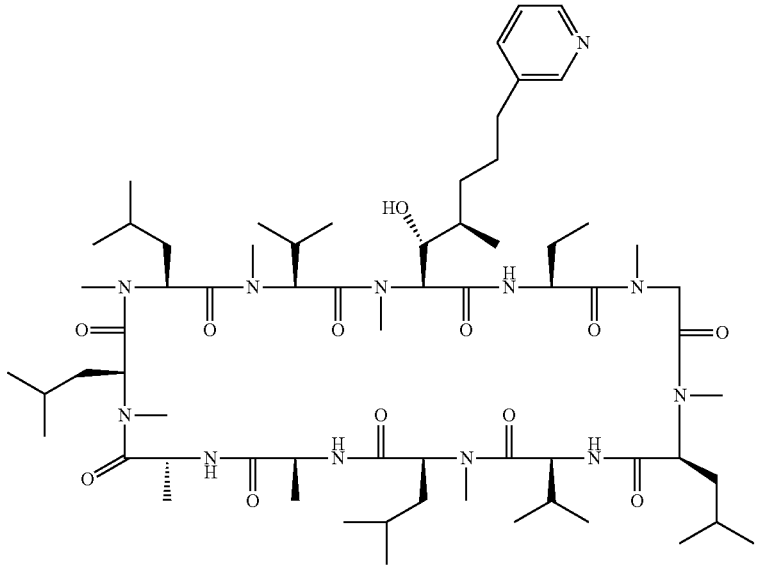

Compound 31

Compound 31 was prepared from Intermediate 7 using (3-pyridinylmethyl)triphenylphosphonium chloride as the Wittig reagent, followed by hydrogenation using 10% palladium on carbon as described above. ES/MS: 1267.4 MH+; ¹H NMR (CDCl₃, ppm) δ 7.13 (d, 1H, amide NH), 7.20 (m, 1H, pyridine CH). 7.51 (m, 2H, amide NH & pyridine CH), 7.69 (d, 1H, amide NH), 7.98 (d, 1H, amide NH), 8.43 (m, 2H, pyridine 2CH).

Example 32

Compound 32: [(2S,3R,4R)-3-Hydroxy-4-methyl-2-(methylamino)-7-(pyrimidin-2-yl)-heptanoic acid]¹ cyclosporin A

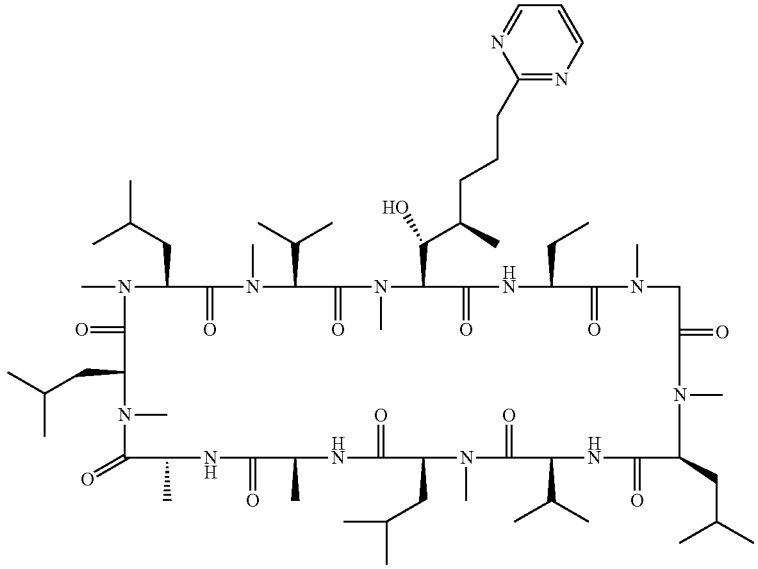

Compound 32

Compound 32 was prepared from Intermediate 7 using (2-pyrimidinylmethyl)triphenylphosphonium chloride as the Wittig reagent, followed by hydrogenation using 10% palladium on carbon as described above. ESMS MH$^+$1268.47; $^1$H NMR (CDCl$_3$, ppm) δ 7.11 (t, 1H, Ar—H), 7.15 (d, 1H, amide NH), 7.46 (d, 1H, amide NH), 7.73 (d, 1H, amide NH), 7.97 (d, 1H, amide NH), 8.66 (d, 2H, Ar—H).

Example 33

Compound 33: [2S,3R,4R)-3-Hydroxy-4-methyl-2-(methylamino)-7-(pyrid-4-yl) heptanoic acid]$^1$[(R)-methoxymethyl Sar]$^3$ cyclosporin A Compound 33

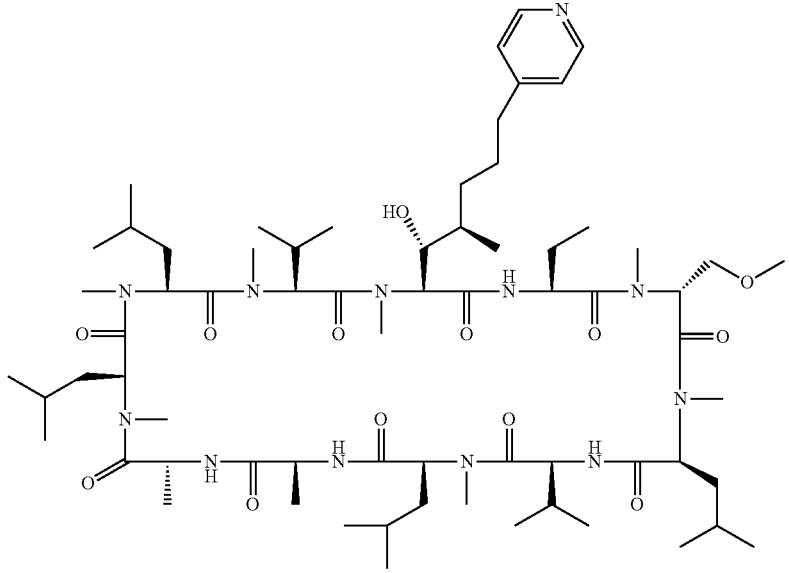

Compound 33 was prepared from Intermediate 13, which was converted to the aldehyde and protected at the MeBmt OH group essentially as described in Scheme 1a. The resulting intermediate was reacted with triphenyl pyrid-4-ylmethylphosphonium bromide as the Wittig reagent, and subsequently hydrogenated using 10% palladium on carbon as described above. ES/MS: 1311.4 MH$^+$; $^1$H NMR (CDCl$_3$, ppm) δ 7.12 (m, 3H, amide NH & pyridine 2CH), 7.49 (d, 1H, amide NH), 7.70 (d, 1H, amide NH), 8.03 (d, 1H, amide NH), 8.49 (d, 2H, pyridine 2CH).

Example 34

Compound 34: [2S,3R,4R)-3-Hydroxy-4-methyl-2-(methylamino)-7-(pyrid-2-yl)heptanoic acid]$^1$[(R)-hydroxymethyl Sar]$^3$ cyclosporin A Compound 34

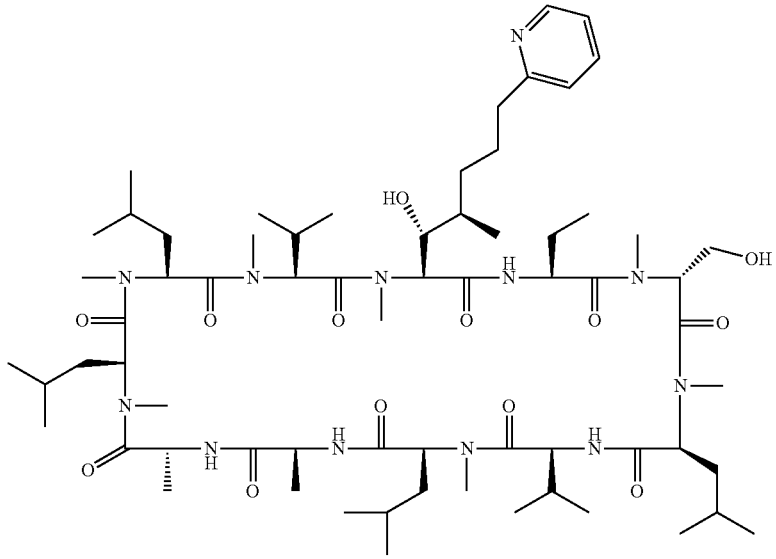

Intermediate 16 (175 mg, 0.127 mmol) dissolved in methanol (4.4 mL) was treated with an aqueous solution (1.86 mL) containing potassium carbonate (140 mg, 1.015 mmol). The colourless solution was stirred for 17 hours then partitioned between ethyl acetate and water. The organic phase was dried over sodium sulfate then concentrated. Preparative TLC using as eluents 60% acetone and 40% isohexane provided Compound 34 as a white solid. ESMS 1297.78 MH+; $^1$H NMR (CDCl$_3$, ppm) δ 7.11 (m, 2H, pyridine 2CH), 7.16 (d, 1H, amide NH), 7.51 (d, 1H, amide NH), 7.59 (td, 1H, pyridine CH), 7.72 (d, 1H, amide NH), 8.08 (d, 1H, amide NH), 8.50 (d, 1H, pyridine CH).

Example 35

Compound 35: [2S,3R,4R)-3-Hydroxy-4-methyl-2-(methylamino)-7-(pyrid-2-yl)heptanoic acid]$^1$[(R)-thiomethyl Sar]$^3$ cyclosporin A

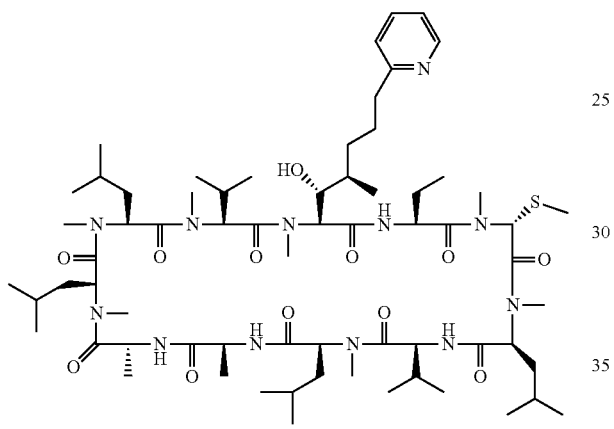

Compound 35

To a solution of diisopropylamine (0.17 ml, 1.2 mmol) in dry THF (6 ml) at −78° C. under an atmosphere of nitrogen was added dropwise n-butyl lithium (1.6 M in hexane, 0.76 ml, 1.2 mmol) and the resulting mixture was stirred at −78° C. for 60 minutes.

A solution of dry Compound 29 (dried by azeotroping with toluene then kept in desiccator overnight in the presence of P$_2$O$_5$) (127 mg, 0.1 mmol) in dry THF (5 ml) was added and the reaction was stirred for 1 h. The resulting mixture was allowed to warm to −60° C. over a period of 1 hour then cool back down to −78° C. before the addition of methylsulfonylsulfanylmethane (0.13 ml, 1.2 mmol). After 30 minutes the reaction mixture was allowed to warm to room temperature; then after 2 hours acetic acid (80 μL, 1.4 mmol) was added. The mixture was partitioned between ethyl acetate and a saturated solution of ammonium chloride. The organic phase was separated, dried (Na$_2$SO$_4$) and concentrated. The crude product was purified by SCX using a solvent gradient from 100% methanol→0.4M ammonia in methanol followed by MPLC chromatography using a solvent gradient of 100% dichloromethane→5% methanol in dichloromethane to give Compound 35. ES/MS: 1313.9 MH+; $^1$H NMR (CDCl$_3$, ppm) δ 2.18 (s, 3H, SMe), 5.80 (s, 1H, sarcosine H), 7.15 (m, 3H, amide NH & pyridine 2CH), 7.36 (d, 1H, amide NH), 7.60 (td, 1H, pyridine CH), 7.73 (d, 1H, amide NH), 7.95 (d, 1H, amide NH), 8.53 (d, 1H, pyridine CH).

Example III—Compounds of the Invention Prepared Via the O-Alkylation Route

Example 36

Compound 36: [(2S,3R,4R)-3-Hydroxy-4-methyl-2-(methylamino)-6-(pyrimidin-2-yloxy)-hexanoic acid]$^1$ cyclosporin A

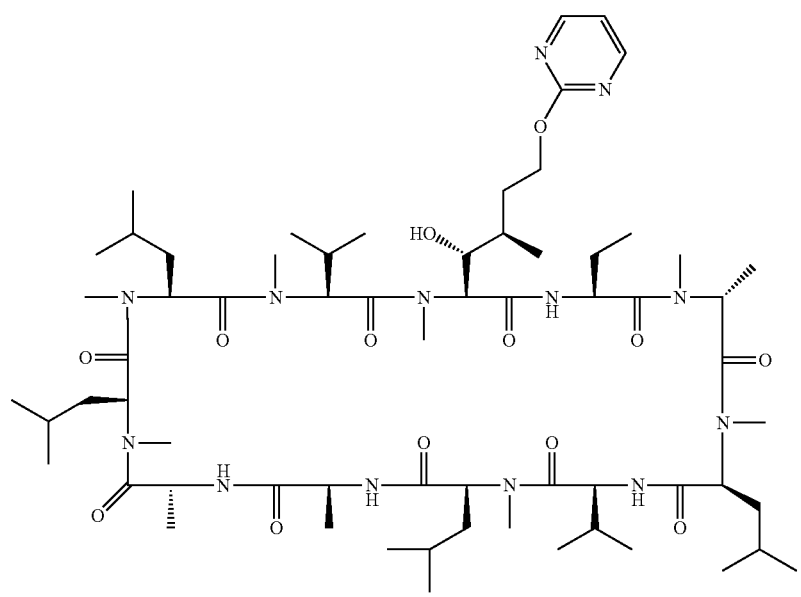

Compound 36

Compound 36 was synthesized as shown in below. Briefly, to (155 mg, 0.128 mmol) of Intermediate 11 dissolved in dichloromethane (1.5 mL) was added benzyltriethylammonium chloride (29 mg, 0.128 mmol) and aqueous KOH solution (40%, 2.1 mL). 2-Methylsulfonyl pyrimidine (20.2 mg, 0.128 mmol) was added and the mixture stirred rapidly for 18 hours at room temperature. The reaction mixture was partitioned between water and ethyl acetate. The aqueous layer was further extracted with ethyl acetate and the combined organic layers dried (NaSO$_4$) and evaporated in vacuo. The residue was purified by silica gel chromatography using a gradient of 100% dichloromethane to 5% methanol in dichloromethane to provide Compound 36 as a white solid. ESMS MH$^+$1284.3; $^1$H NMR (CDCl$_3$, ppm) δ 6.90 (t, 1H, Ar—H), 7.25 (d, 1H, amide NH), 7.38 (d, 1H, amide NH), 7.77 (d, 1H, amide NH), 8.12 (d, 1H, amide NH), 8.50 (d, 2H, Ar—H).

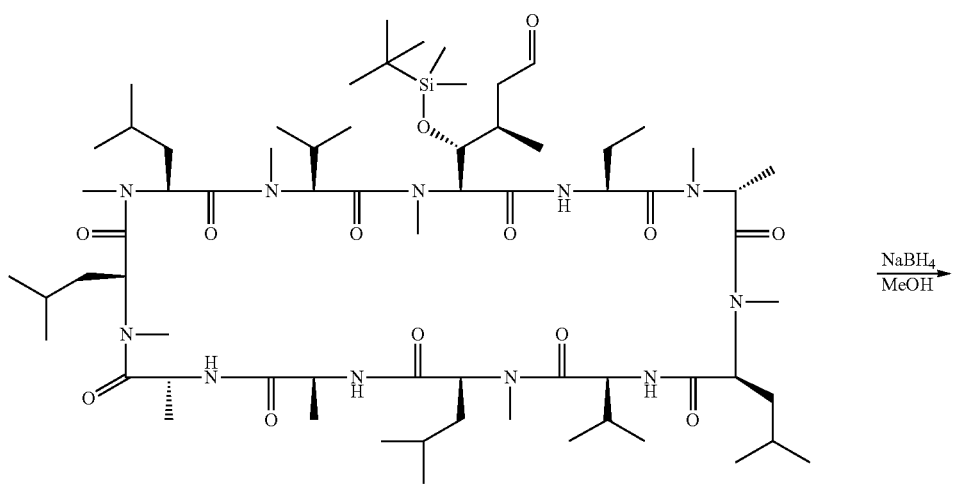

Intermediate 4

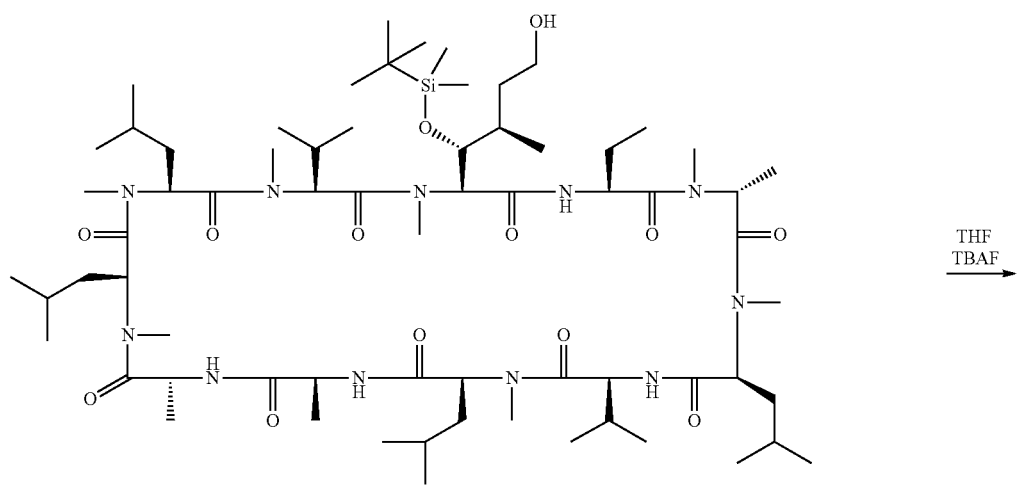

Intermediate 10

-continued
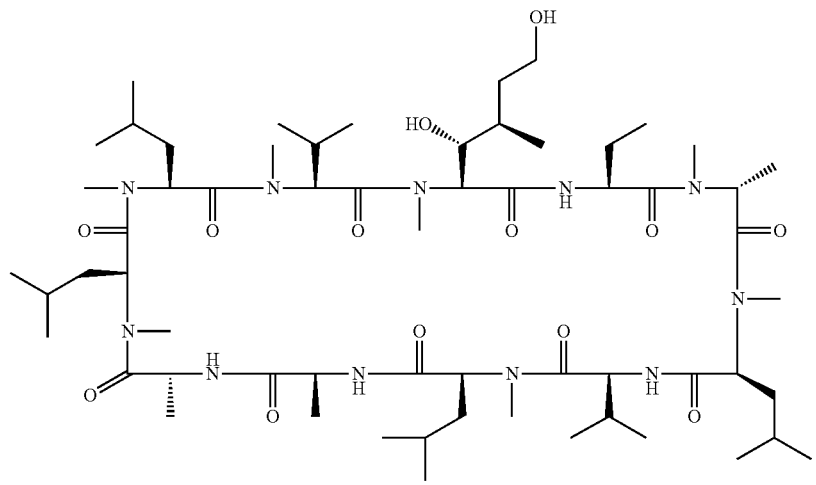 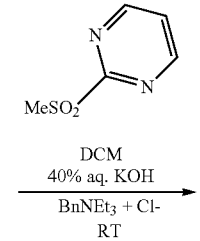
Intermediate 11
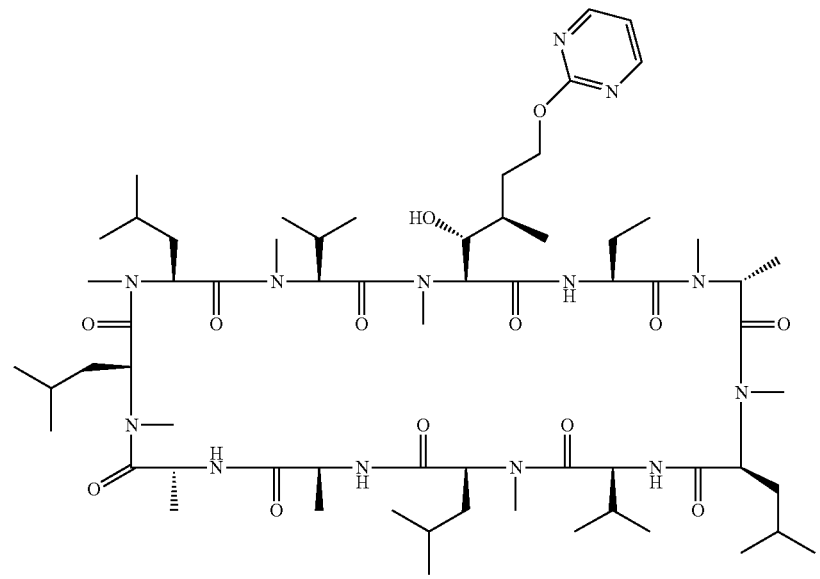
Compound 36

One of ordinary skill in the art may replace the 2-methylsulfonyl pyrimidine with an alternative 2-methylsulfonyl heterocycle (2-methylsulfonyl Het[1]) to provide compounds with the alternative heterocycles.

Example 37

Compound 37: [(2S,3R,4R)-3-Hydroxy-4-methyl-2-(methylamino)-6-(pyridin-4-ylmethoxy)-hexanoic acid][1] cyclosporin A Compound 37

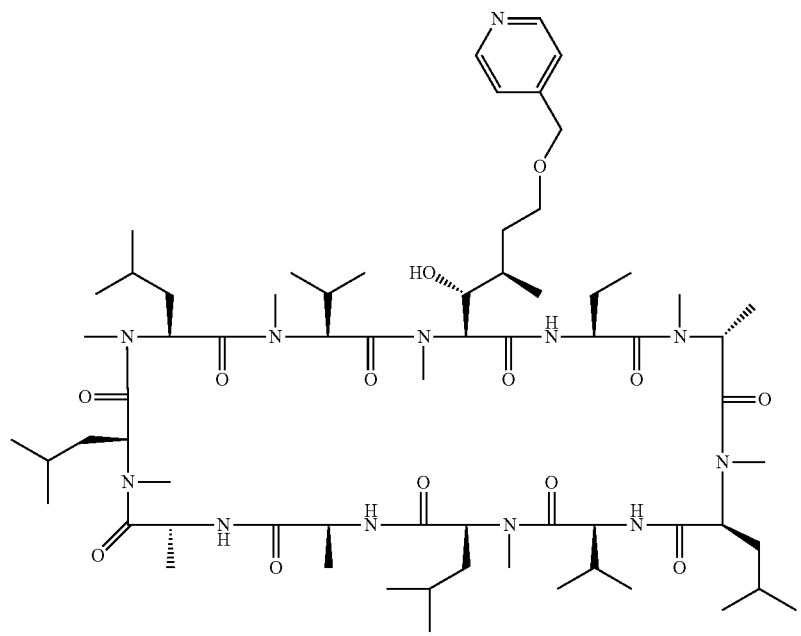

Compound 37 was prepared essentially as described for Compound 36, except that 4-bromomethyl pyridine was used as the alkylating reagent. ES/MS: 1297.9 MH+; $^1$H NMR (CDCl$_3$, ppm) δ 7.28 (m, 3H, amide NH & pyridine 2CH), 7.55 (d, 1H, amide NH), 7.80 (d, 1H, amide NH), 8.18 (d, 1H, amide NH), 8.58 (d, 2H, pyridine 2CH).

Example 38

Preparation of compounds of Formula I wherein $R^2$ is n-propyl may be prepared from Cyclosporin G by adapting one or more of the schemes disclosed herein.

Example 39

Preparation of compounds of Formula I wherein $R^2$ is methyl may be prepared from Cyclosporin B by adapting one or more of the schemes disclosed herein.

Example 40

Preparation of compounds of Formula I wherein $R^2$ is —CH(CH$_3$)OH may be prepared from Cyclosporin C by adapting one or more of the schemes disclosed herein.

Example 41

Preparation of compounds of Formula I wherein $R^2$ is isopropyl may be prepared from Cyclosporin D by adapting one or more of the schemes disclosed herein.

Example 42

Preparation of compounds of Formula I wherein $R^3$ is —CH$_2$OH or —CH$_2$OCH$_3$. Compounds of Formula I wherein $R^3$ is —CH$_2$OH may be prepared essentially as described by D. Seebach et al. (1993) Helvetica Chimica Acta 73(4): 1564-1590. The compound may be subsequently methylated to provide a compound wherein $R^3$ is —CH$_2$OCH$_3$ (e.g., as described in the synthesis of Intermediate 13).

Example 43

Preparation of compounds of Formula I wherein $R^3$ is —OC$_{1-6}$alkyl or —SC$_{1-6}$alkyl may be prepared essentially as described in US 2010/0167996 (for example, see the synthesis of Intermediate 12; also see the synthesis of Compound 35.

Example 44

Preparation of compounds of Formula I wherein is $R^4$ ethyl may be prepared essentially as described in *J. Med. Chem.* 2014, 57(17) 7145-7159, and *Org. Process Res. Dev.* 2014, 18, 1763-1770.

Example 45

Preparation of compounds of Formula I wherein $R^5$ is isopropyl may be prepared essentially as described in *J. Med. Chem.* 2014, 57(17) 7145-7159, and *Org. Process Res. Dev.* 2014, 18, 1763-1770.

Example 46

Preparation of compounds of Formula I wherein $R^5$ is —CH$_2$C(CH$_3$)$_2$(OH), —CH(CH$_3$)(CH$_2$CH$_3$) or —CH$_2$CH(R$^b$)(CH$_2$CH$_3$) may be prepared essentially as described in *J. Med. Chem.* 2014, 57, 8503-8516 and WO2014049540.

Example 47

Preparation of compounds of Formula I wherein $R^6$ is —$CH_2OH$ may be prepared, for example, by biotransformation, essentially as described in *The Journal of Antibiotics*, 1989, 42 (4), 591-597.

Example 48

Preparation of compounds of Formula I wherein $R^3$ is either

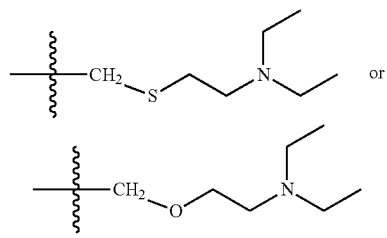

may be prepared essentially as described in WO2012/051194 or WO2013/181339.

Example 49

General Procedures and Biological Assays
Protease-Free PPIase Assay

The protease-free PPIase assay measures the rate of cis to trans conversion of a peptide substrate catalyzed by the enzyme cyclophilin A. Addition of a cyclophilin A inhibitor (e.g., a test compound) slows the catalyzed rate and a $K_i$ value is obtained. A $K_i$ value of less than 10 nM demonstrates that the test compound is a potent inhibitor of cyclophilin A.

Materials
Assay Buffer:
35 mM HEPES pH 7.8, filtered through a 0.2 μm filter. 50 μM DTT was added prior to use each day and then the buffer was stored on ice.

Enzyme:
Human recombinant cyclophilin A (Cyp A) (Sigma C3805) enzyme was diluted to 1 μM with enzyme dilution buffer (20 mM HEPES pH 7.8, 40% glycerol, 50 μM DTT and 1 μM BSA) and stored at −20° C.

Substrate:
Succinimide-Ala-Ala-Pro-Phe-p-nitroanilide (SUC-AAPF-pNA) (from Bachem AG, L-1400), 20 mg/ml prepared in 0.5 M LiCl in trifluoroethanol.

Method
All readings were taken with an Agilent 8453 Spectrophotometer which includes of a cuvette holder, stirrer and chiller to maintain a stirred cuvette temperature of 10.0±0.1° C. The temperature is monitored by the use of a temperature probe. To prevent UV degradation of test compounds, the light below 290 nm was blocked using a glass slide in the light path. 1.5 ml of the assay buffer was put into a 3 ml quartz cuvette and cooled to 10.0±0.1° C. while stirring (vigorous but not so fast as to produce cavitation). The inhibitor was diluted in 100% DMSO, and then added to the assay to a maximum final concentration of 0.5% DMSO in the assay. A blank spectrum was obtained, then 3 μL of enzyme was added (2 nM final concentration) and then 3 μL substrate (60 μM final concentration) added. The absorbance was measured at 330 nm for 300 s or 500 s for blank runs (NOTE: the substrate must be added in one quick injection and the measurements started immediately to minimize mixing errors).

A first order rate equation was fitted to the absorbance data, for each concentration of inhibitor, to obtain the rate constant (the first 10 to 15 seconds were excluded as mixing causes errors in this portion of curve). The catalytic rate was calculated from the enzymatic rate constant minus the background rate constant. An exponential curve was generated using the catalytic rate constants versus the inhibitor concentration to obtain the $K_i$ value for the inhibitor. The $K_i$ value is indicative of the binding affinity between the test compound and cyclophilin A.

Calcineurin Phosphatase (CaN) Assay

The calcineurin phosphatase assay is a means for estimating the immunosuppressive potential of a test compound. Calcineurin is a serine-threonine protein phosphatase that on activation dephosphorylates members of the nuclear factor of activated T cells (NFAT), which are important in T lymphocyte activation. Cyclosporin A bound to cyclophilin A (Cyp A) inhibits calcineurin activity, thus resulting in immunosuppressive effects. Although Cyclosporin A only inhibits calcineurin when bound to Cyp A, some Cyclosporin A analogs will also bind calcineurin in the absence of Cyp A. Alternatively, some Cyclosporin A analogs bind cyclophilin A but do not inhibit calcineurin activity.

To investigate the immunosuppressive potential of exemplary compounds of Formula I, which are cyclosporin analogs, their ability to inhibit calcineurin activity was measured in the presence and absence of Cyp A.

The CaN assay kit used is based on a colorimetric assay for measuring calcineurin phosphatase activity, and it is commercially available (Enzo Life Sciences and Calbiochem). Calmodulin is also required for calcineurin activity and RII phosphopeptide is used as an efficient peptide substrate for calcineurin. We have modified the method to enable measurement of Cyp A-dependent and Cyp A-independent inhibition of calcineurin through the addition of Cyp A in a 1:1 complex with the inhibitor. The detection of free phosphate released is based on the classic Malachite green assay.

Materials
Enzo Life Sciences CaN Assay Kit: BML-AK804
2× assay buffer: 100 mM Tris, pH7.5, 200 mM NaCl, 12 mM $MgCl_2$, 1 mM DTT, 0.05% NP-40, 1 mM $CaCl_2$
Malachite Green: BIOMOL Green™ reagent
Calmodulin (Human, recombinant): was thawed on ice, diluted 1:50 with 2× assay buffer, and then stored on ice.
Calcineurin: was thawed quickly, stored on ice immediately, diluted 1:12.5 with 1× assay buffer, and then stored on ice.
R-II Substrate: 915 μL ultrapure water (UPW) was added to the 1.5 mg vial substrate to give a final concentration of 0.75 mM.
Inhibitors: 2.5 mM inhibitor in 100% DMSO.
Cyp A: recombinant human CypA (Sigma C3805), 1 mg/ml; Recombinant 6-His tagged CypA prepared by the University of Edinburgh was also used. Comparison of the results showed that both enzymes gave identical results.

Method
Inhibitor dilutions: inhibitor compounds were diluted in UPW in polypropylene low-binding 96 well plates at 5× the final assay concentration. For samples 'without Cyp A', a 4-point dilution series of the inhibitor was prepared in duplicate to obtain a final assay concentration of 10, 1, 0.1 and 0.01 μM. For samples 'with Cyp A', a 7-point dilution series was prepared to obtain a 1:1 complex of the inhibitor with CypA; the inhibitor and Cyp A final assay concentrations of 10, 3.33, 1.11, 0.37, 0.12, 0.04, 0.014 µM were prepared. Cyclosporin A inhibitor controls were also prepared to obtain a final concentration of 10 µM Cyclosporin A with and without 10 µM Cyp A.

Assay Setup: using the half area 96 well plates supplied with the kit, 10 µl UPW was added to duplicate wells to provide the non-inhibited control. 10 µl of the inhibitor or the inhibitor/Cyp A complex was added to the appropriate sample wells. 25 µl of the 2× assay buffer with CaM was added to all wells, then 5 µl of CaN was added to all wells (40 U per well final concentration) except duplicate 'no calcineurin blank' wells to which 5 µL 1× assay buffer was added. The assay plate was placed in an oven at 30° C. for 15 minutes to equilibrate to the reaction temperature. The reaction was started by the addition of 10 µl RII-peptide (0.15 mM final concentration). The reaction was allowed to proceed at 30° C. for a time period in which the reaction is linear for about 60 minutes. The reaction was then terminated by adding 100 µl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no Calcineurin blank' from all the absorbance readings and plotting the background corrected absorbances against $Log_{10}$ inhibitor concentration. A sigmoidal-dose response curve was fitted to the data using GraphPad Prism Software.

Cyclosporin A is a potent inhibitor of calcineurin activity and therefore a potent immunosuppressive. It exerts its immunosuppressive activity by binding to cyclophilin A to form a complex, which then binds to calcineurin and thereby inhibits calcineurin activity. As shown in the Tables, Cyclosporin A has a $IC_{50}$ value of 210 nM in the calcineurin/cyclophilin A assay. Thus, compounds with values higher than 210 nM in this assay will be predictably less immunosuppressive than cyclosporin A. As can be seen from Tables 1-3, compounds of Formula I produce much higher values than 210 nM in this assay and so would be expected to be much less immunosuppressive than cyclosporin A.

Mixed Lymphocyte Reaction ("MLR") Assay

The MLR assay is widely used in the field of immunology to measure T cell proliferation, and therefore is another means of estimating the immunosuppressive potential of test compounds. In the MLR assay, splenocytes isolated from two different strains of mice, termed Stimulator (e.g. BALB/c mice) and Responder (e.g. C57BL/6 mice), are mixed in cell culture, in turn eliciting an alloimmune response (immunity against antigens between individuals of the same species). Alloimmunity results in robust proliferation of T cells contained within the splenocyte cell population from both strains of mice. To ensure that T cell proliferation is restricted to only the Responder population (C57BL/6), the Stimulator cells (BALB/c) are first inactivated via x-irradiation before co-culture with Responder cells in the absence or presence of different concentrations of test compound. If the test compound present in the culture medium is immunosuppressive the proliferation of the responder cells is reduced. Total proliferation is quantified by the cellular uptake of [$^3$H]-thymidine, which occurs during cell division. Therefore, compounds that are less immunosuppressive than Cyclosporin A will require a higher concentration to reduce T cell proliferation; and compounds that are not immunosuppressive will not affect T cell proliferation even at the highest concentrations tested.

Female C57BL/6 and BALB/c mice, 6-8 weeks of age, were obtained from the Frederick Cancer Research and Development Center of the National Cancer Institute (Frederick, Md.). Spleens were harvested aseptically from all mice and single cell suspensions were prepared by disaggregating the cells with frosted glass slides, allowing the debris to settle, and washing the cells twice with complete medium. Complete medium consists of RPMI 1640 medium containing 25 mM HEPES buffer (HyClone, Logan, Utah) supplemented with 10% heat-inactivated fetal bovine serum (FBS; Atlanta Biologicals, Lawrenceville, Ga.), 100 µg/mL streptomycin, 100 U/mL penicillin G, 0.25 µg/mL amphotericin B (HyClone), 2 mM L-glutamine dipeptide (HyClone), and $2\times10^{-5}$ M 2-mercaptoethanol (Sigma). Cells were washed twice and resuspended in complete medium. Cell counts were performed using a Beckman Coulter Z-1 particle counter (Fullerton, Calif.). Cell viability was determined by propidium iodide (PI) staining using an Accuri C6 flow cytometer (Ann Arbor, Mich.).

Spleen cells from C57BL/6 ($H-2^b$) and BALB/c ($H-2^d$) were used as responder (R) and stimulator (S) cells, respectively. Cells were plated in triplicate in 96-well flat microtiter plates (Costar, Cambridge, Mass.) such that each well contained $2\times10^5$ R and $8\times10^5$ S cells. Cultures were incubated in the absence or presence of various concentrations of Cyclosporin A, test compounds (e.g., a compound of Formula I), or medium at 37° C. in humidified 5% $CO_2$ for five days, pulsed with $^3$H-thymidine ($^3$H-TdR) for the final 16 hours of incubation, and harvested using a Brandel 96-well cell harvester (Gaithersburg, Md.). Proliferation was measured by counting the radioactivity on filter mats in a Wallac 1450 Microbeta TriLux scintillation counter (Turku, Finland). Controls to demonstrate effective inactivation by the x-irradiation were performed by incubating the S cells with 5 µg/mL of PHA at $2\times10^5$ cells/well. These control cultures were incubated for 3 days under the same conditions as those described for the MLR; lymphoproliferation was determined in the same manner as described above.

Water Solubility Assay (Measured in pH 7.8 Buffer)

The aqueous solubility of a compound of Formula I in buffer (pH 7.8) was measured by recording the onset of precipitation of the compound as a function of increasing concentration. The onset of precipitation, if it occurred, was detected by an increase in absorbance at 650 nm.

Materials

Assay Buffer: 35 mM HEPES pH 7.8
Stock solutions of Control and Test Compounds: 10 mM in 100% DMSO.

Method 10 mM stock solutions of control and test compounds were prepared in 100% DMSO. A series of dilutions were prepared from the stock in DMSO so that the final concentrations in the assay were 0, 3.33, 10, 25, 50, 75 and 100 µM and DMSO was limited to 1%.

Assay buffer (247.5 µl) was placed into flat bottomed transparent 96-well plate. For blank samples DMSO (2.5 µl) was added. For test and control samples 2.5 µl of the appropriate DMSO dilution stocks were added to the appropriate well. All test and control compounds were performed in triplicate.

The plates were sealed with adhesive plate seal and shaken at 250 rpm at 25° C. for 18 h on a plate shaker. After incubation the plate seals were taken off and any bubbles observed in wells removed. The plates were read on a SpectraMaxM5 with a 5 s pre-shake at 650 nm. Data files were transferred to the appropriate worksheet and the solubility range of the compounds was calculated from the data.

The values shown in the Tables indicate the concentration in µM (micromolar) at which the compound remains in solution.

Biological and Physico-Chemical Properties of Compounds of the Invention

Example compounds of Formula I are listed and described in Tables 1-3, below. Compounds of the present invention include those listed and described in Tables 1-3, and their pharmaceutically acceptable salts.

Data showing Cyclophilin A (Cyp A) inhibitory activity, immunosuppressive potential, and aqueous solubility for select compounds represented by Formula I are described in Tables 1, 2 and 3. General procedures and assays used to obtain the data were described above.

The data show that compounds represented by Formula I are potent inhibitors of cyclophilin A ($K_i \leq 15$ nM), as measured by the protease-free PPIase assay. Many compounds having Formula I are also non-immunosuppressive, as measured by the MLR and CaN assays; and are more water soluble than unmodified Cyclosporin A, as measured by the Water Solubility Assay.

TABLE 1

Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (µM) |
|---|---|---|---|---|
| Cyclosporin A | 1.5 | 210 | 1 | 10-25 |
| 1 | 15 | 2,700 | 125 | 75-100 |
| 2 | 4.6 | >10,000 | | >100 |
| 3 | 8.6 | >10,000 | | >100 |
| 4 | 5.1 | 6,900 | | >100 |
| 5 | 4.1 | 8,600 | | >100 |
| 6 | 5.1 | 4,750 | | >100 |
| 7 | 5.6 | 7,850 | | >100 |
| 8 | 7.4 | >10,000 | | |
| 9 | 2.3 | >10,000 | | 25-50 |
| 10 | 7.1 | 4,000 | | 25-50 |
| 11 | 5.6 | 2,500 | 25 | 50-75 |
| 12 | 3.8 | 1,400 | 25 | 50-75 |
| 13 | 3.2 | 1,450 | 25 | 25-50 |
| 14 | 1.5 | 8,750 | | |
| 15 | 2.5 | 1,600 | 50 | 50-75 |

TABLE 2

Data Showing Cyclophilin A (Cyp A) Inhibitory Activity, immunosuppressive potential, and aqueous solubility for select Compounds having Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (µM) |
|---|---|---|---|---|
| 16 | 0.72 | >10,000 | | 25-50 |
| 17 | 3.9 | 9,250 | | 25-50 |
| 18 | 2.2 | 5,800 | 90 | 50-75 |
| 19 | 5.4 | >10,000 | | |
| 20 | 5.7 | >10,000 | | >100 |
| 21 | 3.2 | >10,000 | | >100 |
| 22 | 3.2 | 1,160 | 30 | >100 |
| 23 | 2.1 | 3,340 | 50 | >100 |
| 24 | 3.5 | 650 | 10 | >100 |
| 25 | 3.8 | 1,460 | 50 | >100 |
| 26 | 12.2 | >10,000 | | >100 |
| 27 | 6.8 | 1,106 | 10 | >100 |
| 28 | 3.9 | >10,000 | | 50-75 |
| 29 | 11 | 2,650 | 40 | 50-75 |

TABLE 3

Cyclophilin A (Cyp A) inhibitory activity, immunosuppressive potential, and aqueous solubility for select Compounds of Formula I

| Compound | Protease-free PPIase Assay* $K_i$ (nM) | Calcineurin Phosphatase (CaN) Assay (+CypA)** $IC_{50}$ (nM) | Mixed Lymphocyte Reaction (MLR) Assay*** | Water Solubility Assay**** (µM) |
|---|---|---|---|---|
| 30 | 14 | 3,150 | | 50-75 |
| 31 | 9.5 | 3,950 | | 50-75 |
| 32 | 8.3 | 3,450 | 50 | 75-100 |
| 33 | 3.1 | 2,390 | 50 | 75-100 |
| 34 | 3.1 | 4,650 | 150 | >100 |
| 35 | 4.4 | 1,600 | 10 | 75-100 |
| 36 | 7.7 | 1,255 | 50 | >100 |
| 37 | 5.6 | 5,640 | | >100 |

In Tables 1, 2 and 3:

*Data generated using the protease-free PPIase assay.

**Data generated using the Calcineurin Phosphatase (CaN) Assay. No significant inhibition of CaN was observed in the absence or presence of CypA. Data obtained in the presence of Cyp A (+CypA) are reported in the Table.

***Data generated using the Mixed Lymphocyte Reaction ("MLR") Assay. The values shown are expressed as the $IC_{50}$ for the compound relative to the $IC_{50}$ for Cyclosporin A. Thus, a value of 10, for example indicates that the compound is about ten times less immunosuppressive than Cyclosporin A.

****Data generated using the Water Solubility Assay.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A compound having the following structure:

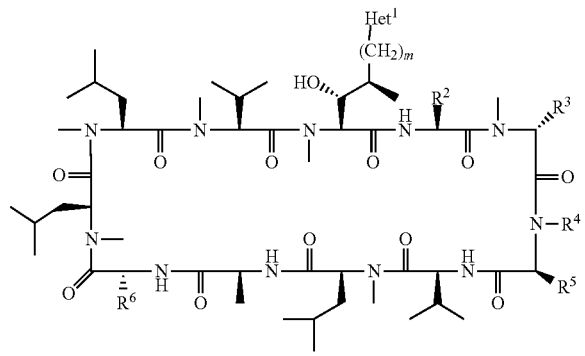

wherein:
Het$^1$ is a monocyclic or polycyclic aromatic heterocyclyl optionally substituted with 1 or more R$^a$;
wherein each R$^a$ is independently selected from the group consisting of halogen, —C$_{1-6}$ alkyl, —OC$_{1-6}$ alkyl and —(CH$_2$)$_n$R$^b$;
wherein each R$^b$ is independently Het$^2$, —C$_{1-6}$ haloalkyl, —OH, —NH$_2$, —NH(C$_{1-6}$ alkyl) or —N(C$_{1-6}$ alkyl)$_2$, wherein each C$_{1-6}$ alkyl is the same or different; and
wherein each Het$^2$ is independently a heterocyclyl optionally substituted with one or more halogen, —C$_{1-6}$ alkyl, —C$_{1-6}$ haloalkyl, —OC$_{1-6}$alkyl, —(CH$_2$)$_{1-6}$OH, —(CH$_2$)$_{1-6}$NH$_2$, —(CH$_2$)$_{1-6}$NH ($C_{1-6}$ alkyl) or —$(CH_2)_{1-6}N(C_{1-6}$ alkyl$)_2$, wherein each $C_{1-6}$ alkyl is the same or different;

$R^2$ is —$CH_3$, —$CH_2CH_3$, —$CH(CH_3)_2$, —$CH_2CH_2CH_3$ or —$CH(CH)_3(OH)$;

$R^3$ is —H, —$C_{1-6}$alkyl, —$OC_{1-6}$alkyl, —$SC_{1-6}$alkyl, —$CH_2OH$, —$CH_2OCH_3$,

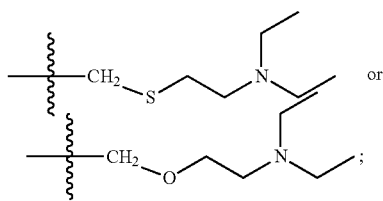

$R^4$ is —$CH_3$ or —$CH_2CH_3$;

$R^5$ is —$CH(CH_3)_2$, —$CH_2CH(CH_3)_2$, —$CH_2C(CH_3)_2$(OH), —$CH(CH_3)(CH_2CH_3)$ or —$CH_2CH(R^c)$($CH_2CH_3$), wherein $R^c$ is $OC_{1-6}$ alkyl;

$R^6$ is —$CH_3$ or —$CH_2OH$;

m is 1; and n is 1, 2 or 3;

or a pharmaceutically acceptable salt thereof.

2. The compound of claim 1, wherein $Het^1$ is a bicyclic aromatic heterocyclyl, said compound having the following structure:

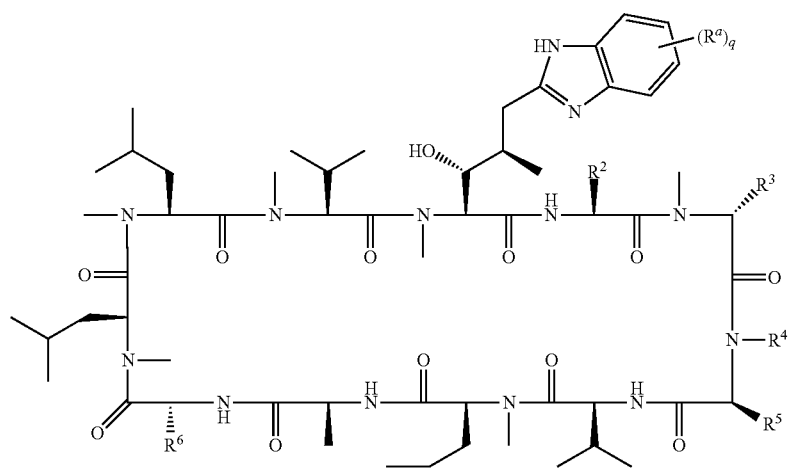

wherein q is 0, 1, 2, 3 or 4;
or a pharmaceutically acceptable salt thereof.

3. The compound of claim 1, wherein $Het^1$ is a monocyclic aromatic heterocyclyl, said compound having the following structure:

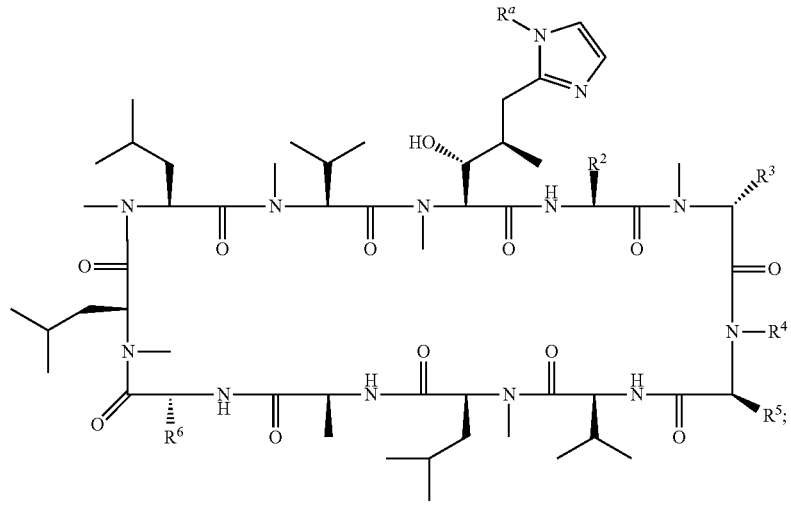

or a pharmaceutically acceptable salt thereof.

4. The compound of claim 1 selected from the group consisting of:
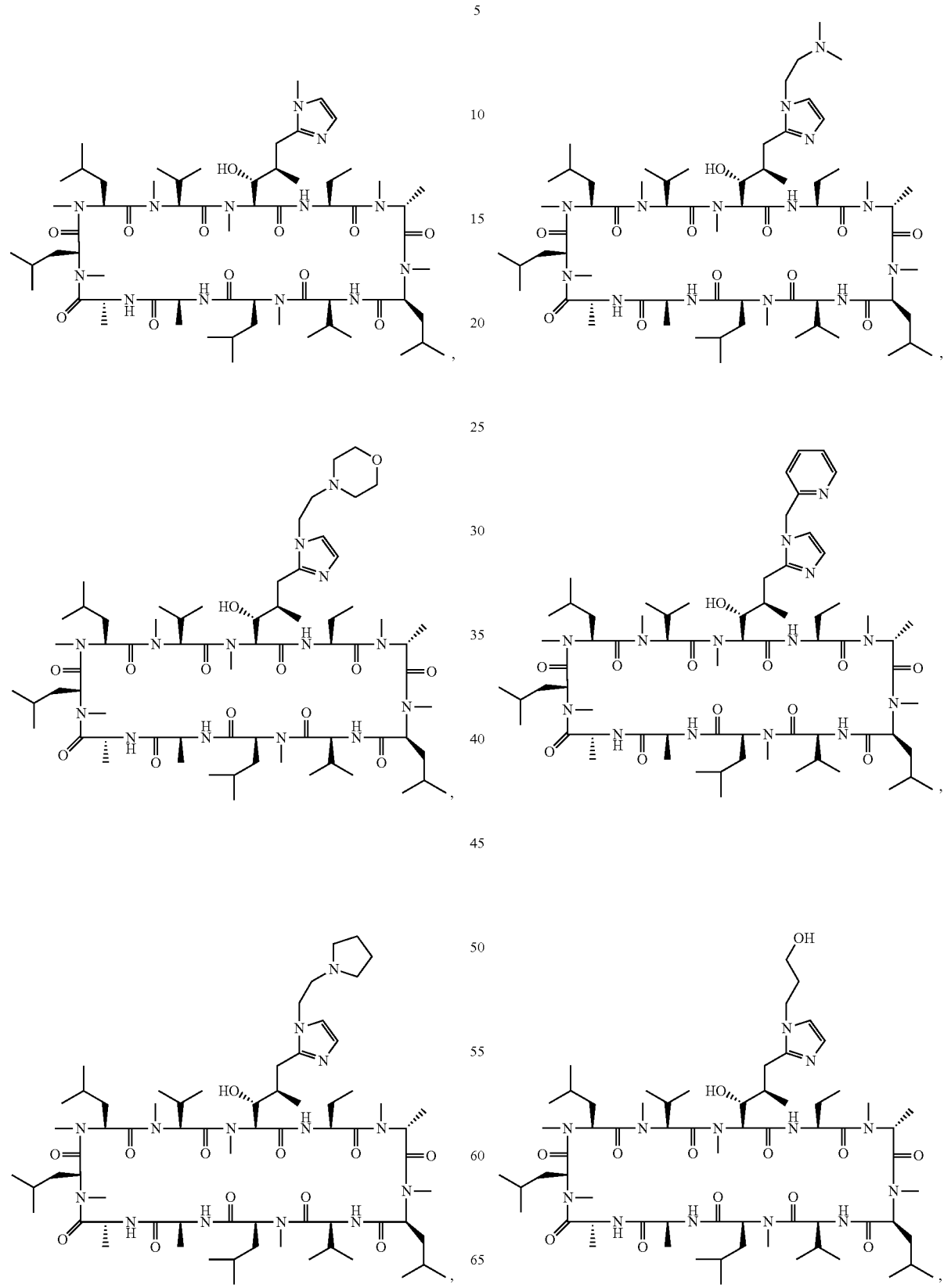

-continued

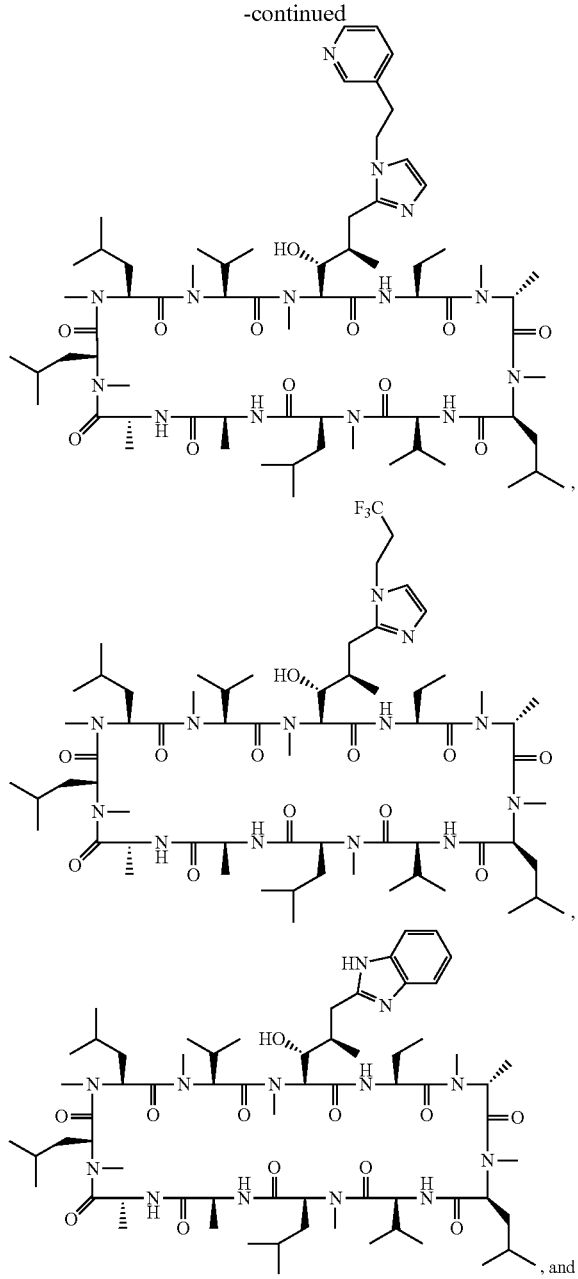

,

, and

-continued

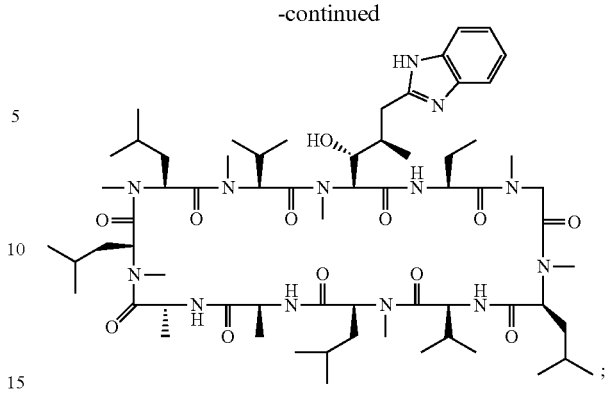

;

and pharmaceutically acceptable salts thereof.

5. A pharmaceutical composition comprising a therapeutically effective amount of a compound of claim 1, or a pharmaceutically acceptable salt thereof, and a pharmaceutically acceptable excipient.

6. A method of treating a medical condition in a subject in need thereof, the method comprising administering to the subject a therapeutically effective amount of a compound of claim 1, or a pharmaceutically acceptable salt thereof, thereby treating the condition;

wherein the medical condition is dry eye, dry eye disease, ocular surface inflammation, blepharitis, meibomian gland disease, allergic conjunctivitis, pterygium, ocular symptoms of graft versus host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, adenoviral keratoconjunctivitis, ocular rosacea, pinguecula, corneal transplant rejection, inflammation in an eye caused by an ocular surgery or suppressed tear production due to ocular inflammation associated with keratoconjunctivitis sicca.

7. The method of claim 6, wherein the subject is a human.

* * * * *